US011717548B2

(12) United States Patent
Irvine et al.

(10) Patent No.: US 11,717,548 B2
(45) Date of Patent: Aug. 8, 2023

(54) SYNTHETIC ONCOLYTIC LNP-REPLICON RNA AND USES FOR CANCER IMMUNOTHERAPY

(71) Applicants: Massachusetts Institute of Technology, Cambridge, MA (US); Ohio State Innovation Foundation, Columbus, OH (US)

(72) Inventors: Darrell J. Irvine, Arlington, MA (US); Karl Dane Wittrup, Chestnut Hill, MA (US); Ron Weiss, Newton, MA (US); Yingzhong Li, Quincy, MA (US); Noor Momin, Cambridge, MA (US); Yizhou Dong, Dublin, OH (US)

(73) Assignees: Massachusetts Institute of Technology, Cambridge, MA (US); Ohio State Innovation Foundation, Columbus, OH (US)

( * ) Notice: Subject to any disclaimer, the term of this patent is extended or adjusted under 35 U.S.C. 154(b) by 708 days.

(21) Appl. No.: 16/739,407

(22) Filed: Jan. 10, 2020

(65) Prior Publication Data
US 2020/0281994 A1 Sep. 10, 2020

Related U.S. Application Data

(60) Provisional application No. 62/815,611, filed on Mar. 8, 2019.

(51) Int. Cl.
| | | |
|---|---|---|
| *A61K 35/768* | (2015.01) | |
| *A61P 35/00* | (2006.01) | |
| *A61K 9/00* | (2006.01) | |
| *C07K 14/54* | (2006.01) | |
| *C12N 7/00* | (2006.01) | |

(52) U.S. Cl.
CPC .......... *A61K 35/768* (2013.01); *A61K 9/0019* (2013.01); *A61P 35/00* (2018.01); *C07K 14/5434* (2013.01); *C12N 7/00* (2013.01); *C12N 2770/36132* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 5,013,556 A | 5/1991 | Woodie et al. |

FOREIGN PATENT DOCUMENTS

| | | |
|---|---|---|
| WO | WO 2012/006376 A2 | 1/2012 |
| WO | WO 2016/037053 A1 | 3/2016 |

OTHER PUBLICATIONS

Li et al., Multifunctional oncolytic nanoparticles deliver self-replicating IL-12 RNA to eliminate established tumors and prime systemic immunity, Nat Cancer 1(9): 882-893 Sep. (Authors manuscript) (Year: 2020).*
Geall et al., "Nonviral delivery of self-amplifying RNA vaccines", PNAS vol. 109, No. 36, pp. 14604-14609 Sep. 2012.*
International Search Report and Written Opinion dated Apr. 17, 2020, in connection with PCT/US2020/013069.
International Preliminary Report on Patentability dated Sep. 23, 2021, in connection with PCT/US2020/013069.
[No Author Listed] Koch Institute Immune Engineering Symposium 2019. Feb. 6, 2019.
Lai et al., Lipid nanoparticles that deliver IL-12 messenger RNA suppress tumorigenesis in MYC oncogene-driven hepatocellular carcinoma. J Immunother Cancer. Nov. 20, 2018;6(1):125. doi: 10.1186/s40425-018-0431-x. PMID: 30458889; PMCID: PMC6247677.
Lundstrom, Alphavirus vectors as tools in neuroscience and gene therapy. Virus Res. May 2, 2016;216:16-25. doi: 10.1016/j.virusres.2015.08.015. Epub Aug. 22, 2015. PMID: 26307195.
Lundstrom, Alphavirus-based vaccines. Curr Opin Mol Ther. Feb. 2002;4(1):28-34. PMID: 11883692.
Lundstrom, Replicon RNA Viral Vectors as Vaccines. Vaccines (Basel). Nov. 7, 2016;4(4):39. doi: 10.3390/vaccines4040039. PMID: 27827980; PMCID: PMC5192359.
Momin et al., Anchoring of intratumorally administered cytokines to collagen safely potentiates systemic cancer immunotherapy. Sci Transl Med. Jun. 26, 2019;11(498):eaaw2614. doi: 10.1126/scitranslmed.aaw2614. PMID: 31243150; PMCID: PMC7811803.
Ren et al., Immunogene therapy of recurrent glioblastoma multiforme with a liposomally encapsulated replication-incompetent Semliki forest virus vector carrying the human interleukin-12 gene—a phase I/II clinical protocol. J Neurooncol. Aug.-Sep. 2003;64(1-2):147-54. doi: 10.1007/BF02700029. Erratum in: J Neurooncol. Nov. 2003;65(2):191. PMID: 12952295.
Zhao et al., Lipid Polymer Hybrid Nanomaterials for mRNA Delivery. Cell Mol Bioeng. Oct. 2018;11(5):397-406. doi: 10.1007/s12195-018-0536-9. Epub Jun. 19, 2018. PMID: 30555598; PMCID: PMC6291228.
Böttcher et al., NK Cells Stimulate Recruitment of cDC1 into the Tumor Microenvironment Promoting Cancer Immune Control. Cell. Feb. 22, 2018;172(5):1022-1037.e14. doi: 10.1016/j.cell.2018.01.004. Epub Feb. 8, 2018.
Eppstein et al., Biological activity of liposome-encapsulated murine interferon gamma is mediated by a cell membrane receptor. Proc Natl Acad Sci U S A. Jun. 1985;82(11):3688-92.
Haverkamp et al., Myeloid-derived suppressor activity is mediated by monocytic lineages maintained by continuous inhibition of extrinsic and intrinsic death pathways. Immunity. Dec. 18, 2014;41(6):947-59. doi: 10.1016/j.immuni.2014.10.020. Epub Dec. 11, 2014.

(Continued)

*Primary Examiner* — Anand U Desai
(74) *Attorney, Agent, or Firm* — Wolf, Greenfield & Sacks, P.C.

(57) ABSTRACT

The present disclosure relates to synthetic oncolytic viruses comprising a lipid nanoparticle comprising one or more types of lipid and a self-amplifying replicon RNA comprising a sequence that encodes an immunomodulatory molecule.

22 Claims, 5 Drawing Sheets

Specification includes a Sequence Listing.

(56) References Cited

OTHER PUBLICATIONS

Hwang et al., Hepatic uptake and degradation of unilamellar sphingomyelin/cholesterol liposomes: a kinetic study. Proc Natl Acad Sci U S A. Jul. 1980;77(7):4030-4.

Kawai et al., TLR signaling. Cell Death Differ. May 2006;13(5):816-25.

Lasek et al., Interleukin 12: still a promising candidate for tumor immunotherapy? Cancer Immunol Immunother. May 2014;63(5):419-35. doi: 10.1007/s00262-014-1523-1. Epub Feb. 11, 2014.

Li et al., Persistent Antigen and Prolonged AKT-mTORC1 Activation Underlie Memory CD8 T Cell Impairment in the Absence of CD4 T Cells. J Immunol. Aug. 15, 2015;195(4):1591-8. doi: 10.4049/jimmunol.1500451. Epub Jul. 10, 2015.

Li et al., An Orthogonal Array Optimization of Lipid-like Nanoparticles for mRNA Delivery in Vivo. Nano Lett. Dec. 9, 2015;15(12):8099-107. doi: 10.1021/acs.nanolett.5b03528. Epub Nov. 6, 2015.

Magna et al. The role of HMGB1 in the pathogenesis of inflammatory and autoimmune diseases. Mol Med. Mar. 24, 2014;20(1):138-46.

McComb et al., Type-I interferon signaling through ISGF3 complex is required for sustained Rip3 activation and necroptosis in macrophages. Proc Natl Acad Sci U S A. Aug. 5, 2014;111(31):E3206-13. doi: 10.1073/pnas.1407068111. Epub Jul. 21, 2014.

Montoya et al.,. Type I interferons produced by dendritic cells promote their phenotypic and functional activation. Blood. May 1, 2002;99(9):3263-71.

Yun et al., Fibroblast growth factors: biology, function, and application for tissue regeneration. J Tissue Eng. Nov. 7, 2010;2010:218142.

Zha et al., ATP-Induced Inflammasome Activation and Pyroptosis Is Regulated by AMP-Activated Protein Kinase in Macrophages. Front Immunol. Dec. 12, 2016;7:597.

\* cited by examiner

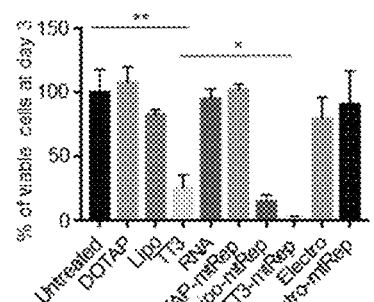
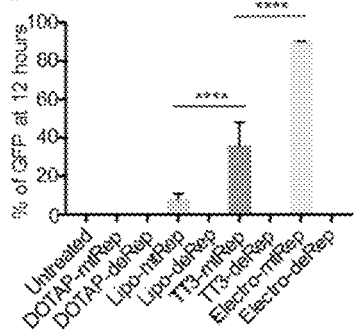
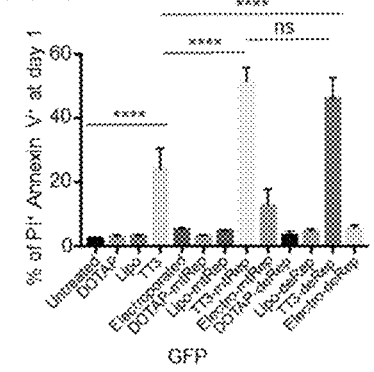
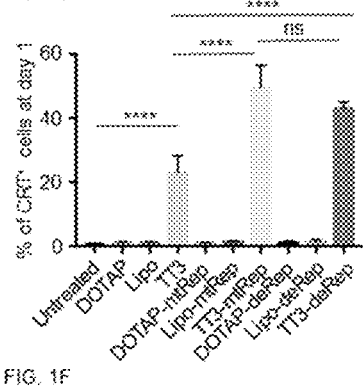
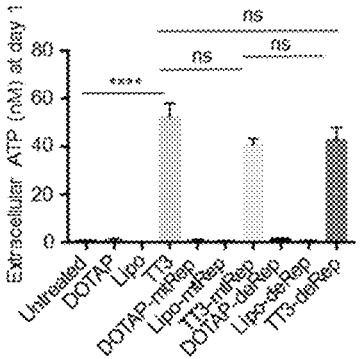
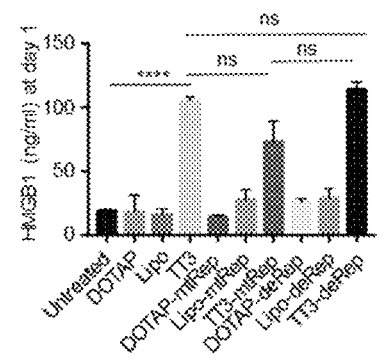
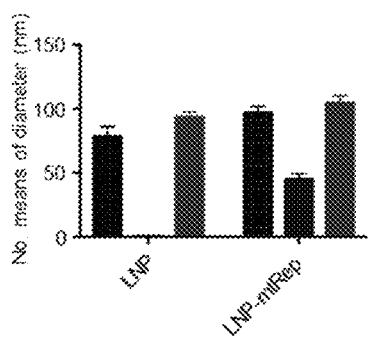
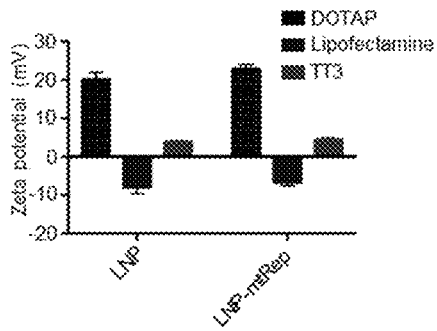

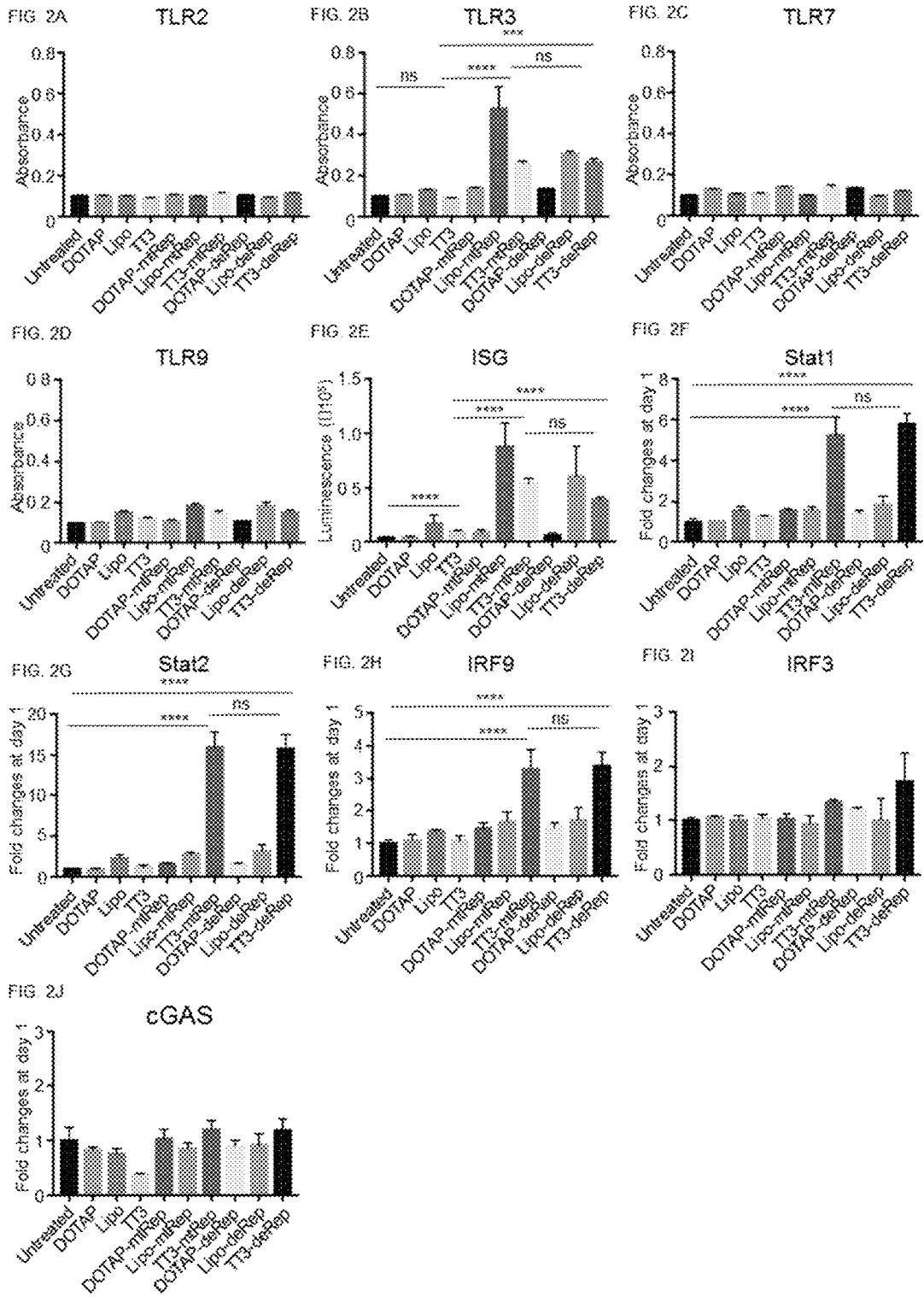

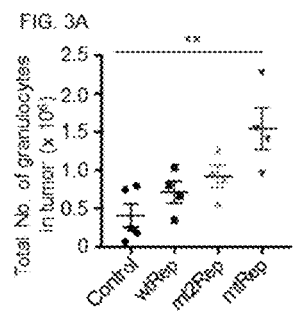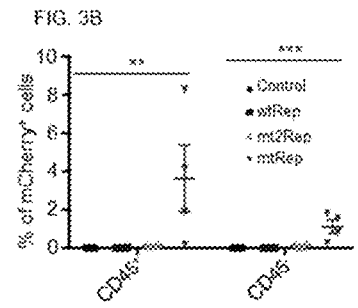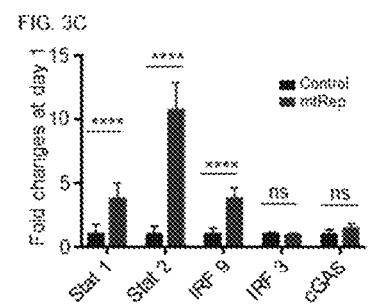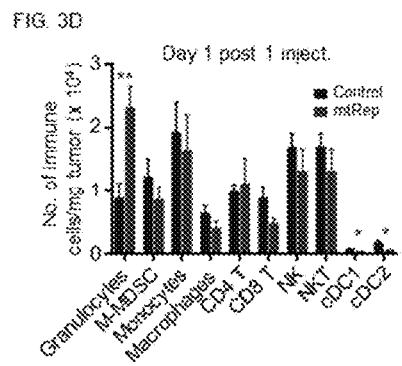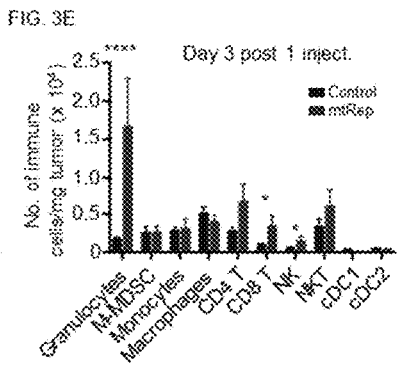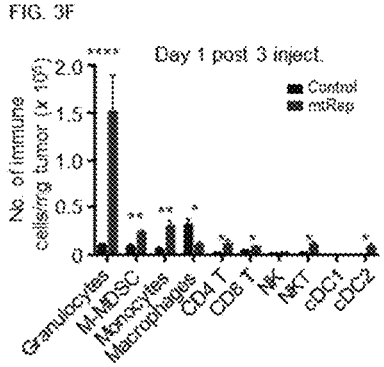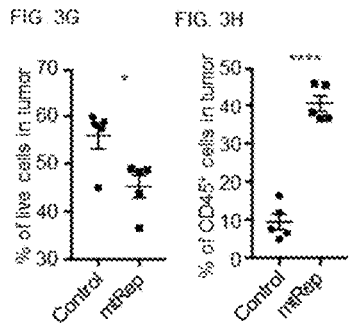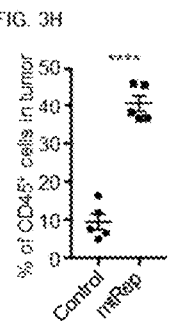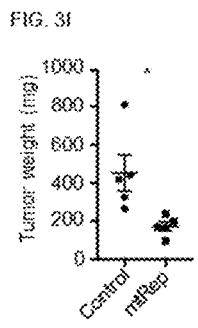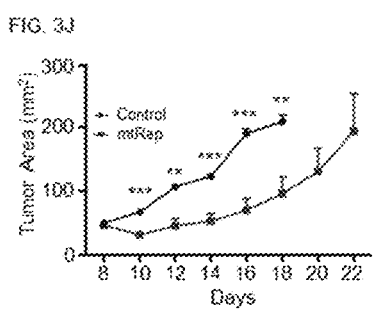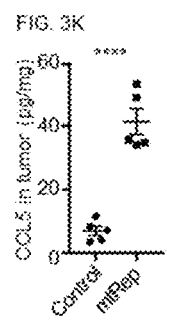

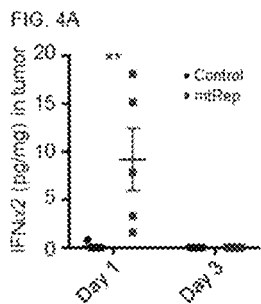
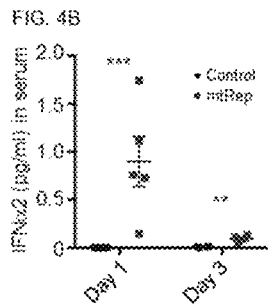
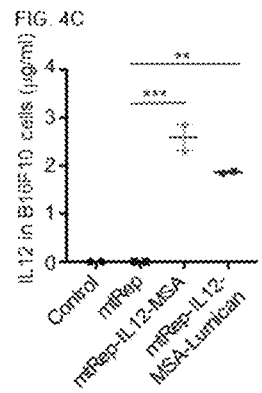
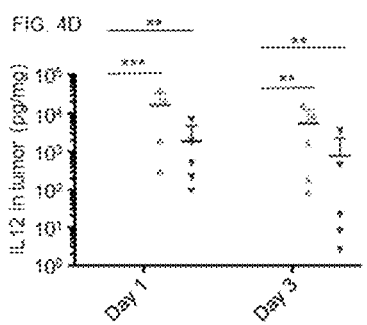
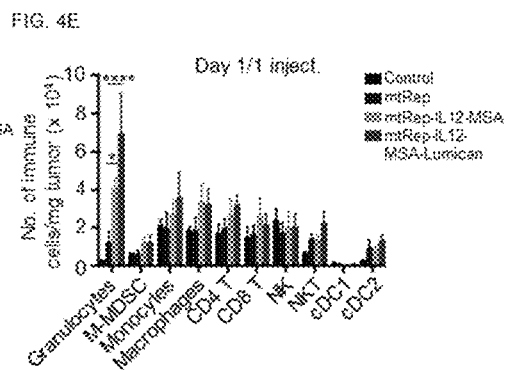
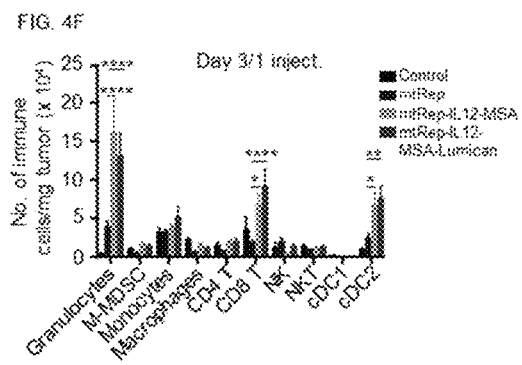
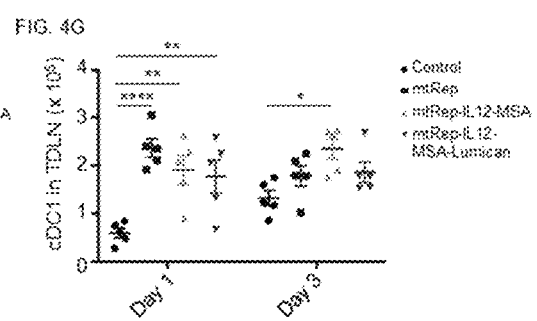

SYNTHETIC ONCOLYTIC LNP-REPLICON RNA AND USES FOR CANCER IMMUNOTHERAPY

RELATED APPLICATION

This application claims priority under 35 U.S.C. § 119(e) to U.S. Provisional Application Ser. No. 62/815,611, filed Mar. 8, 2019, the entire contents of which are incorporated by reference herein.

FEDERALLY SPONSORED RESEARCH

This invention was made with Government support under Grant No. R01 CA206218 awarded by the National Institutes of Health (NIH). The Government has certain rights in the invention.

BACKGROUND

The present disclosure relates to synthetic oncolytic viruses comprising a lipid nanoparticle comprising one or more types of lipid and a self-amplifying replicon RNA comprising a sequence that encodes an immunomodulatory molecule.

SUMMARY

The present disclosure is based, at least in part, on the unexpected discovery that upon injection at a tumor site, a synthetic oncolytic virus successfully triggers anti-cancer immune response of local tumors and enables systemic immunity against distal tumors.

Accordingly, one aspect of the present disclosure provides a synthetic oncolytic virus comprising a lipid nanoparticle comprising one or more types of lipid and a self-amplifying replicon RNA comprising a sequence that encodes an interleukin (IL)-12 molecule. The lipid nanoparticle is capable of triggering immunogenic cell death. The IL-12 molecule is expressed by the self-amplifying replicon RNA.

The synthetic oncolytic virus comprises a lipid nanoparticle. The lipid nanoparticle comprises one or more types of lipids. In some embodiments, the one or more types of lipids comprises a cationic lipid. In some embodiments, the cationic lipid is N1,N3,N5-tris(3-(didodecylamino)propyl)benzene-1,3,5-tricarboxamide (TT3). In some embodiments, the lipid nanoparticle comprises TT3, 1,2-Dioleoyl-sn-glycero-3-phosphoethanolamine (DOPE), cholesterol, and C14-PEG2000.

Further, the synthetic oncolytic virus comprises a self-amplifying replicon RNA. In some embodiments, the self-amplicon RNA is derived from an alphavirus or other Group IV viruses (positive single strand RNA viruses, such as a hepatitis C virus (HCV)). In some embodiments, the alphavirus can be Venezuela Equine Encephalitis virus, Semliki Forest virus, or Sindbis virus.

In some embodiments, the self-amplifying replicon RNA comprises a sequence encoding an IL-12 molecule. In some embodiments, the sequence that encodes the IL-12 molecule is located in a subgenomic region of the self-amplifying replicon RNA.

In some embodiments, the self-amplifying replicon RNA comprises a nucleotide sequence that is at least 90% identical of the wild type (WT) replicon RNA having a sequence of SEQ ID NO: 1. In some embodiments, the self-amplifying replicon RNA is not identical to SEQ ID NO: 1 and is capable of expressing the IL-12 molecule at a higher level compared to the self-amplifying replicon RNA comprising SEQ ID NO: 1. In some embodiments, replicon RNA that is capable of expressing the IL-12 molecule at a higher level comprises a point mutations of G3936C and/or A4758G of SEQ ID NO: 1.

In some embodiments, the self-amplifying replicon RNA further comprises a serum albumin coding sequence. In some embodiments, the self-amplifying replicon RNA further comprises a Lumican coding sequence.

In some aspects, self-amplifying replicon RNA comprises a sequence encoding a IL-12 molecule. In some embodiments, the IL-12 molecule is selected from the group consisting of IL-12, an IL-12 subunit, or a mutant IL-12 molecule that retains the immunomodulatory function. In some further embodiments, the IL-12 molecule comprises IL12α and/or IL12β subunits.

In some embodiments, the lipid nanoparticle has a diameter of about 100-120 nm. In some embodiments, the lipid nanoparticle has a zeta potential of about 3-6 mv.

In some embodiments, the lipid and the self-amplifying replicon RNA have a mass ratio of about 1:2 to 2:1.

The present disclosure, at least in part, relates to a pharmaceutical composition, comprising the synthetic oncolytic virus and a pharmaceutically acceptable carrier.

In some embodiments, pharmaceutical composition is formulated for intratumoral injection.

The present disclosure, at least in part, relates to a method for treating cancer in a subject in need thereof, comprising administering to the subject an effective amount of the synthetic oncolytic virus of any or the synthetic oncolytic virus-containing pharmaceutical composition.

In some embodiments, the subject is a human patient having or suspected of having a cancer. Exemplary target cancers include, but are not limited to melanoma, breast cancer and colon cancer.

In some embodiments, the pharmaceutical composition is administered to the subject in a single dose. In some embodiments, the pharmaceutical composition is administered to the subject by intratumoral injection.

Also within the present disclosure are any of the synthetic oncolytic virus-containing pharmaceutical compositions described herein for use in treating any of the target diseases disclosed herein (e.g., cancer), as well as pharmaceutical compositions comprising the synthetic oncolytic oligonucleotide for use in manufacturing a medicament for cancer treatment.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIGS. 1A-1H are charts showing the effects of B16F10 cells transfected with DOTAP, lipofectamine (Lipo), TT3 nanoparticle (TT3), mutant replicon RNA (RNA), DOTAP, Lipo, and TT3 nanoparticle encapsulate mutant replicon RNA (DOTAP-mtRep, Lipo-mtRep, and TT3-mtRep), electroporation (Electro), and electroporation with mutant replicon RNA (Electro-mtRep). FIG. 1A is a graph showing B16F10 cell viability 3 days post transfection. FIG. 1B is a graph showing GFP expression in B16F10 cells transfected with lipid nanoparticle encapsulated with mutant or dead replicon RNA (deRep). FIG. 1C is a graph showing percentages of PI+ Annexin V+ dead B16F10 cells transfected with lipid nanoparticles or with lipid nanoparticles encapsulated with replicon RNA Immunogenic cell death induced by lipid nanoparticles or with lipid nanoparticles encapsulated with replicon RNA, was shown by percent of calreticulin+(CRT+) cells (FIG. 1D), extracellular ATP (FIG. 1E) and HMGB1 release (FIG. 1F). FIG. 1G shows the diameter of the lipid nanoparticles and lipid nanoparticle loaded with mutant replicon RNAs. FIG. 1H shows the zeta potential of the lipid nanoparticles and lipid nanoparticle loaded with mutant replicon RNAs.

FIGS. 2A-2J are charts showing mtRep and deRep trigger TLR3 signaling and induce ISGF3 complex to necrotic cell death. LNP-replicon RNA trigger TLR3 signaling (FIG. 2B and FIG. 2E) and activates the expression of interferon stimulated genes Stat 1, Stat2, IRF9, IRF3 and cGAS (FIGS. 2F-2J), but does not activate TLR2 (FIG. 2A), TLR7 (FIG. 2C) or TLR9 (FIG. 2D).

FIG. 3A-3K are charts showing TT3-mtRep recruits immune cells and regresses tumor growth. FIG. 3A shows mtRep recruits more Ly6clo Ly6G+ granulocytes 3 days post injection. FIG. 3B shows the percentages of mCherry+ cells in CD45+ and CD45- cells in tumors injected with TT3-mtRep 3 days post injection. FIG. 3C shows the expression of ISGF3 complex (Stat1/Stat2/IRF9) as well as IRF3 and cGAS at 1 day post TT3-mtRep injection. FIGS. 3D-3F show the immune cell infiltration (granulocytes, M-MDSC, monocytes, macrophages, CD4 T, CD8 T, NK, NKT, conventional DC1 (cDC1), and conventional DC2 (cDC2)) into the tumor at day 1 (FIG. 3D), and at day 3 (FIG. 3E) post one injection of TT3-mtRep, and at day 1 post 3 sequential injection (FIG. 3F) of TT3-mtRep. FIGS. 3G-3H show TT3-mtRep induces more cell death (FIG. 3G), more immune cell infiltration (FIG. 3H), reduced tumor weight (FIG. 3I), tumor area (FIG. 3J) and increased expression of CCL5 (FIG. 3K) at one day after 3 sequential injection of TT3-mtRep.

FIGS. 4A-4G are charts showing TT3-mtRep encoding IL12-MSA or IL12-MSA-Lumican effectively modulates tumor microenvironments and immune cell infiltration. FIGS. 4A and 4B show quantification of IFNα2 by ELISA in tumor (FIG. 4A) and in serum (FIG. 4B) one day and three days post TT3-mtRep injection. FIG. 4C shows B16F10 cells transfected with mtRep-IL12-MSA and mtRep-IL12-MSA-Lumican can produce IL-12. FIG. 4D shows IL-12 level in tumor one day and three days post single injection of TT3-mtRep, TT3-mtRep-IL12-MSA, or TT3-mtRep-IL12-MSA-lumican. FIG. 4E-4F shows immune cell infiltration in tumor one day (FIG. 4E) and three days (FIG. 4F) post single injection of TT3-mtRep, TT3-mtRep-IL12-MSA, or TT3-mtRep-IL12-MSA-lumican. FIG. 4G shows numbers of conventional DC1 (cDC1) in tumor draining lymph node one day and three days post single injection of TT3-mtRep, TT3-mtRep-IL12-MSA, or TT3-mtRep-IL12-MSA-lumican.

FIG. 5E shows that TT3-mtRep-IL12 treatment can prevent the recurrence of tumor in cured mice.

DETAILED DESCRIPTION

Figure 5A:
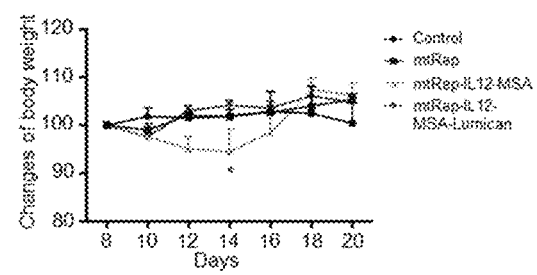
FIGS. 5A-5E are charts showing in vivo synergistic anti-cancer effects of immunomodulatory IL12 and immunogenic cell death induced by TT3-mtRep. The synergistic anti-cancer effects were evaluated by changes of body weight (FIG. 5A), IFNr in serum (FIG. 5B), tumor area (FIG. 5C), and survival curve (FIG. 5D).

The present disclosure is based, at least in part, on the unexpected discovery that upon injection at a tumor site, a synthetic oncolytic virus comprising a lipid nanoparticle comprising one or more types of lipid and a self-amplifying replicon RNA comprising a sequence that encodes an IL-12 molecule successfully triggers anti-cancer immune response of local tumors and enables systemic immunity against distal tumors.

I. Synthetic Oncolytic Virus

The present disclosure, at least in part, relates to a synthetic oncolytic virus. As used herein, the term "synthetic" refers to a non-natural or engineered oncolytic virus as disclosed herein, which includes a lipid nanoparticle and a self-amplifying replicon RNA comprising a sequence that encodes an IL-12 molecule.

In some aspects, the present disclosure relates to utilizing lipid nanoparticles (LNPs), which are capable of inducing immunogenic cell death by themselves, to facilitate the delivery of biologically active agent (e.g., a self-amplifying replicon RNA encoding an IL-12 molecule) into the tumor cells.

(i) Lipid Nanoparticle

The present disclosure, at least in part, relates to the delivery of biologically active molecules to cells using lipid nanoparticles. Specifically, the invention relates to a synthetic oncolytic virus comprising IL-12 expressing self-amplifying replicon RNA encapsulated by lipid nanoparticles, the composition thereof, and methods of using the synthetic oncolytic virus, and the composition thereof to treat a subject having cancer or suspected of having cancer.

A lipid nanoparticle (LNPs), as used herein, refers to vesicle, such as a spherical vesicle, having a contiguous lipid bilayer. Lipid nanoparticles can be used in methods by which pharmaceutical therapies are delivered to targeted locations. Non-limiting examples of LNPs include liposomes, bolaamphiphiles, solid lipid nanoparticles (SLN), nanostructured lipid carriers (NLC), and monolayer membrane structures (e.g., archaeosomes and micelles).

The lipid nanoparticle, as used herein, comprises one or more types of lipids. A lipid, as used herein, refers to a group of organic compounds that include, but are not limited to, esters of fatty acids and in some embodiments are characterized by being insoluble in water, but soluble in many organic solvents. They are usually divided into at least three classes: (1) "simple lipids" which include fats and oils as well as waxes; (2) "compound lipids" which include phospholipids and glycolipids; (3) "derived lipids" such as steroids. Non-limiting examples of lipids include triglycerides (e.g. tristearin), diglycerides (e.g. glycerol bahenate), monoglycerides (e.g. glycerol monostearate), fatty acids (e.g. stearic acid), steroids (e.g. cholesterol), and waxes (e.g. cetyl palmitate). In some embodiments, the one or more types of lipids in the LNP, comprises a cationic lipid.

A cationic lipid, as used herein, refers to any of a number of lipid species that carry a net positive charge at a selected pH, such as physiological pH. Such lipids include, but are not limited to N1,N3,N5-tris(3-(didodecylamino)propyl)benzene-1,3,5-tricarboxamide (TT3), N-(2,3-dioleoyloxy)propyl)-N,N,N-trimethylammonium chloride (DOTAP); lipofectamine; 1,2-DiLinoleyloxy-N,N-dimethylaminopropane (DLinDMA), 1,2-Dilinolenyloxy-N,N-dimethylaminopropane (DLenDMA), dioctadecyldimethylammonium (DODMA), Distearyldimethylammonium (DSDMA), N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); 3-(N—(N',N'-dimethylaminoethane)-carbamoyl)cholesterol (DC-Chol) and N-(1,2-dimyristyloxyprop-3-yl)-N,N-dimethyl-N-hydroxyethyl ammonium bromide (DMRIE).

In some embodiments, the cationic lipid is TT3. TT3, as used herein, is capable of forming lipid nanoparticles for delivery of various biologic active agents into the cells. In addition, the present disclosure also demonstrates that an unloaded TT3-LNP can induce immunogenic cell death (ICD) in cancer cells in vivo and in vitro Immunogenic cell death, as described herein, refers to a form of cell death that can induce an effective immune response through activation of dendritic cells (DCs) and consequent activation of specific T cell response. In some embodiments, the cells that undergo immunogenic cell death (ICD) are tumor cells Immunogenic tumor cell death can trigger an effective anti-tumor immune response. In some embodiments, the synthetic oncolytic virus comprises TT3-LNP encapsulating a self-amplifying replicon RNA encoding only a reporter gene (TT3-LNP-replicon RNA). The self-amplifying replicon RNA can work synergistically with the TT3-LNP to induce higher level of ICD in tumor cells compared to TT3-LNP alone. In other embodiments, the synthetic oncolytic virus comprises a TT3-LNP encapsulating a self-amplifying replicon RNA encoding an IL-12 molecule. IL-12, which is an immunoregulatory cytokine, elicits potent immune response against the local tumor. Moreover, the combination of TT3-LNP, self-amplifying replicon RNA and IL-12 expression, not only is effective in synergistic inhibition of tumor cells on site, but also elicits a systemic anti-tumor immune response to kill distal tumor cells and prevent the recurrence of tumors.

In some embodiments, the cationic lipid is DOTAP. DOTAP, as used herein, is also capable of forming lipid nanoparticles. DOTAP can be used for the highly efficient transfection of DNA including yeast artificial chromosomes (YACs) into eukaryotic cells for transient or stable gene expression, and is also suitable for the efficient transfer of other negatively charged molecules, such as RNA, oligonucleotides, nucleotides, ribonucleo-protein (RNP) complexes, and proteins into research samples of mammalian cells.

In other embodiments, the cationic lipid is lipofectamine Lipofectamine, as used herein, is a common transfection reagent, produced and sold by Invitrogen, used in molecular and cellular biology. It is used to increase the transfection efficiency of RNA (including mRNA and siRNA) or plasmid DNA into in vitro cell cultures by lipofection. Lipofectamine contains lipid subunits that can form liposomes or lipid nanoparticles in an aqueous environment, which entrap the transfection payload, e.g. self-amplifying replicon RNA. The RNA-containing liposomes (positively charged on their surface) can fuse with the negatively charged plasma membrane of living cells, due to the neutral co-lipid mediating fusion of the liposome with the cell membrane, allowing nucleic acid cargo molecules to cross into the cytoplasm for replication or expression.

In some embodiments, LNPs are composed primarily of cationic lipids along with other lipid ingredients. These typically include other lipid molecules belonging but not limited to the phosphatidylcholine (PC) class (e.g., 1,2-Distearoyl-sn-glycero-3-phosphocholine (DSPC), and 1,2-Dioleoyl-sn-glycero-3-phosphoethanolamine (DOPE), sterols (e.g., cholesterol) and Polyethylene glycol (PEG)-lipid conjugates (e.g., 1,2-distearoyl-sn-glycero-3-phosphoethanolamine-N-[folate(polyethylene glycol)-2000 (DSPE-PEG2000) and 1,2-dimyristoyl-sn-glycero-3-phosphoethanolamine-N-[methoxy(polyethylene glycol)-2000 (C14-PEG2000). Table 1 shows the formulation of two LNPs, TT3-LNP and DOTAP-LNP.

TABLE 1

| | | | | |
|---|---|---|---|---|
| DOTAP-LNP | DOTAP | DSPC | Cholesterol | DSPE-PEG2000 |
| Molar ratio | 40 | 10 | 48 | 2 |
| TT3-LNP | TT3 | DOPE | Cholesterol | C14-PEG2000 |
| Molar Ratio | 20 | 30 | 40 | 0.75 |

Particle size of lipid nanoparticles can affect drug release rate, bio-distribution, mucoadhesion, cellular uptake of water and buffer exchange to the interior of the nanoparticles, and protein diffusion. In some embodiments, the diameter of the LNPs ranges from 30 to 150 nm. In some embodiments, the diameter of the LNPs ranges from 100-120 nm. In some embodiments, the diameter of the LNPs can be 30 nm, 40 nm, 50 nm, 60 nm, 70 nm, 80 nm, 90 nm, 100 nm, 101 nm, 102 nm, 103 nm, 104 nm, 105 nm, 106 nm, 107 nm, 108 nm, 109 nm, 110 nm, 111 nm, 112 nm, 113 nm, 114 nm, 115 nm, 116 nm, 117 nm, 118 nm, 119 nm, or 120 nm.

Zeta potential is a measure of the effective electric charge on the lipid nanoparticle surface. The magnitude of the zeta potential provides information about particle stability. In some embodiments, the zeta potential of the LNPs ranges from −10 millivolts (my) to 25 mv. In some embodiments, the zeta potential of the LNPs ranges from 3-6 mv. In some embodiments, the zeta potential of the LNPs can be 3 mv, 3.1 mv, 3.2 mv, 3.3 mv, 3.4 my, 3.5 mv, 3.6 mv, 3.7 mv, 3.8 mv, 3.9 mv, 4 mv, 4.1 mv, 4.2 mv, 4.3 mv, 4.4 mv, 4.5 mv, 4.6 my, 4.7 mv, 4.8 mv, 4.9 mv, 5 mv, 5.1 mv, 5.2 mv, 5.3 mv, 5.4 mv, 5.5 mv, 5.6 mv, 5.7 my, 5.8 mv, 5.9 mv, and 6 mv.

The present disclosure, at least in part, is related to encapsulating replicon RNA with the lipid nanoparticles. In some embodiments, the mass ratio between the LNPs and the replicon RNA ranges from 1:2 to 2:1. In some embodiments, the mass ratio between the LNPs and the replicon RNA can be 1:2, 1:1.5, 1:1.2, 1:1, 1.1:1, 1.2:1, 1.3:1, 1.4:1, 1.5:1, 1.6:1, 1.7:1, 1.8:1, 1.9:1 and 2:1. In some embodiments, the mass ratio between the LNPs and the replicon RNA can be 1:1.

(ii) Self-Amplifying Replicon RNA

In the present disclosure, a self-amplifying replicon RNA encoding IL-12 molecule under the subgenomic promoter, in place of the structural proteins required for virus replication, are of substantial interest in cancer immunotherapy. As used herein, the term "self-amplifying replicon RNA" refers to a self-replicating genetic element comprised a RNA that replicates from one origin of replication. The terms "replicon RNA" and "self-amplifying replicon RNA" are used interchangeably herein. In some embodiments, the self-amplifying replicon RNA is a viral replicon.

A virus is a small pathogen that is only capable of replication inside a living host cell (e.g., prokaryotic and eukaryotic cells). Outside of living cells, viruses exist as independent particles (e.g., viral particles or virions), which comprise genetic material in the form of DNA or RNA, the latter of which can be single-stranded or double-stranded. Viruses with DNA are referred to as DNA viruses, and viruses with RNA are referred to as RNA viruses. In some cases, the virus comprises nucleic acid-associated proteins and the combination of the virus and nucleic acid-associated proteins is referred to as nucleoprotein. In addition to the genetic material, viruses have a single or double protein coat, also known as a capsid, which facilitates attachment of the virus to a living host cell's receptors during infection and protects the genetic material of the virus from enzymatic degradation. The combination of nucleoprotein and the capsid is referred to as a nucleocapsid. In some cases, viruses have a lipid bilayer envelope, studded with virus-coded, glycosylated (trans-) membrane-associated proteins. Once a virus has infected a living host cell, the virus is dependent on the living host cell to supply the machinery for its replication, and propagation thereafter. The viral genome codes for some structural proteins and non-structural regulatory proteins.

As used herein, the term "subgenome" or "subgenomic" refers to a smaller section of the whole replicon genome. Accordingly, subgenomic transcription, as used herein, refers to the transcription of one or more genes in the replicon genome but not all the genes constituting the replicon genome. In one embodiment, subgenomic transcription refers to transcription of the genes of experimental or therapeutic interest, which are described elsewhere herein.

The term "structural protein," as used in the context of viruses herein, refers to proteins that constitute the structural components of mature assembled virus particles or virions. Non-limiting examples of such structural proteins include nucleocapsid core proteins (e.g., gag proteins), enzymes packaged within the virus particle (e.g., pol proteins), and membrane components (e.g., env proteins). In contrast, the term "non-structural protein," as used in the context of viruses herein, refer to proteins that are expressed within the host cell but do not constitute structural components of the virus particle or virion. Some of the roles of non-structural proteins include, but are not limited to, replicon formation, immunomodulation, and transactivation of structural protein genes.

In some embodiments, the self-amplifying replicon RNA is derived from an alphavirus. Distinct from host mRNA, alphavirus replicon RNAs encode a set of four nonstructural proteins (nsPs 1-4) that are responsible both for genome replication and, when engineered to include genes encoding non-virus products, such as IL-12 molecules, provide for transcription of such non-viral products under the subgenomic promoter. Alphaviruses are part of the Group IV Togaviridae family of viruses, possess a positive sense, single-stranded RNA genome, and are characterized by an icosahedral nucleocapsid. Other non-limiting examples of Group IV viruses can be Astroviridae, Caliciviridae, Coronaviridae, Flaviviridae, Picornaviridae, Arteriviridae, and Togaviridae. The alphavirus genus includes 26 enveloped viruses that infect eukaryotes. Alphaviruses have a broad host range and are transmitted by mosquitos and hematophagous arthropods. Non-limiting examples of alphaviruses include Venezuelan equine encephalitis virus (VEE), Semliki Forest virus (SF), Sindbis virus (SIN),Eastern Equine Encephalitis virus (EEE), Western equine encephalitis virus (WEE), Everglades virus (EVE), Mucambo virus (MUC), Pixuna virus (PIX), Semliki Forest virus (SF), Middelburg virus (MID), Chikungunya virus (CHIK), O'Nyong-Nyong virus (ONN), Ross River virus (RR), Barmah Forest virus (BF), Getah virus (GET), Sagiyama virus (SAG), Bebaru virus (BEB), Mayaro virus (MAY), Una virus (UNA), Aura virus (AURA), Babanki virus (BAB), Highlands J virus (HJ), and Fort Morgan virus (FM).

In the present disclosure, at least in part, the alphavirus replicon is a VEE alphavirus replicon. The VEE virus is a viral pathogen typically carried by mosquitos that causes VEE or encephalomyelitis predominately in equine species. Humans, however, may also contract VEE, and people with weakened immune systems are especially at risk of having severe complications if infected with VEE. The virion of VEE is spherical and possesses a lipid membrane with glycoprotein surface proteins spread around the outer surface. Typically, VEE has a genome of approximately 11.45 kb, excluding the 5'-terminal cap and 3'-terminal poly(A) tract, and comprises 4 nonstructural proteins (nsPs) and 5 structural proteins. The non-structural proteins include nsP1, nsP2, nsP3, and nsP4, while the structural region encodes proteins C, E3, E2, 6K, and E1. In some instances, the self-amplifying replicon RNA is a WT replicon RNA derived from VEE. The sequence of the VEE virus WT replicon RNA is set forth in SEQ ID NO: 1:

```
                                                          (SEQ ID NO: 1)
ATGGGCGGCGCATGAGAGAAGCCCAGACCAATTACCTACCCAAAATGGAGAAAGTTCACGTT

GACATCGAGGAAGACAGCCCATTCCTCAGAGCTTTGCAGCGGAGCTTCCCGCAGTTTGAGGT

AGAAGCCAAGCAGGTCACTGATAATGACCATGCTAATGCCAGAGCGTTTTCGCATCTGGCTT

CAAAACTGATCGAAACGGAGGTGGACCCATCCGACACGATCCTTGACATTGGAAGTGCGCCC

GCCCGCAGAATGTATTCTAAGCACAAGTATCATTGTATCTGTCCGATGAGATGTGCGGAAGA

TCCGGACAGATTGTATAAGTATGCAACTAAGCTGAAGAAAAACTGTAAGGAAATAACTGATA

AGGAATTGGACAAGAAAATGAAGGAGCTGGCCGCCGTCATGAGCGACCCTGACCTGGAAACT

GAGACTATGTGCCTCCACGACGACGAGTCGTGTCGCTACGAAGGGCAAGTCGCTGTTTACCA

GGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATAT

CCATCATACTCTACCAACTGGGCCGACGAAACCGTGTTAACGGCTCGTAACATAGGCCTATG

CAGCTCTGACGTTATGGAGCGGTCACGTAGAGGGATGTCCATTCTTAGAAAGAAGTATTTGA

AACCATCCAACAATGTTCTATTCTCTGTTGGCTCGACCATCTACCACGAGAAGAGGGACTTA

CTGAGGAGCTGGCACCTGCCGTCTGTATTTCACTTACGTGGCAAGCAAAATTACACATGTCG

GTGTGAGACTATAGTTAGTTGCGACGGGTACGTCGTTAAAAGAATAGCTATCAGTCCAGGCC

TGTATGGGAAGCCTTCAGGCTATGCTGCTACGATGCACCGCGAGGGATTCTTGTGCTGCAAA
```

-continued

```
GTGACAGACACATTGAACGGGGAGAGGGTCTCTTTTCCCGTGTGCACGTATGTGCCAGCTAC
ATTGTGTGACCAAATGACTGGCATACTGGCAACAGATGTCAGTGCGGACGACGCGCAAAAAC
TGCTGGTTGGGCTCAACCAGCGTATAGTCGTCAACGGTCGCACCCAGAGAAACACCAATACC
ATGAAAAATTACCTTTTGCCCGTAGTGGCCCAGGCATTTGCTAGGTGGGCAAAGGAATATAA
GGAAGATCAAGAAGATGAAAGGCCACTAGGACTACGAGATAGACAGTTAGTCATGGGGTGTT
GTTGGGCTTTTAGAAGGCACAAGATAACATCTATTTATAAGCGCCCGGATACCCAAACCATC
ATCAAAGTGAACAGCGATTTCCACTCATTCGTGCTGCCCAGGATAGGCAGTAACACATTGGA
GATCGGGCTGAGAACAAGAATCAGGAAAATGTTAGAGGAGCACAAGGAGCCGTCACCTCTCA
TTACCGCCGAGGACGTACAAGAAGCTAAGTGCGCAGCCGATGAGGCTAAGGAGGTGCGTGAA
GCCGAGGAGTTGCGCGCAGCTCTACCACCTTTGGCAGCTGATGTTGAGGAGCCCACTCTGGA
GGCAGACGTCGACTTGATGTTACAAGAGGCTGGGGCCGGCTCAGTGGAGACACCTCGTGGCT
TGATAAAGGTTACCAGCTACGATGGCGAGGACAAGATCGGCTCTTACGCTGTGCTTTCTCCG
CAGGCTGTACTCAAGAGTGAAAAATTATCTTGCATCCACCCTCTCGCTGAACAAGTCATAGT
GATAACACACTCTGGCCGAAAAGGGCGTTATGCCGTGGAACCATACCATGGTAAAGTAGTGG
TGCCAGAGGGACATGCAATACCCGTCCAGGACTTTCAAGCTCTGAGTGAAAGTGCCACCATT
GTGTACAACGAACGTGAGTTCGTAAACAGGTACCTGCACCATATTGCCACACATGGAGGAGC
GCTGAACACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGGCTCACA
GGCGAGCTGGTGGATCCTCCCTTCCATGAATTCGCCTACGAGAGTCTGAGAACACGACCAGC
CGCTCCTTACCAAGTACCAACCATAGGGGTGTATGGCGTGCCAGGATCAGGCAAGTCTGGCA
TCATTAAAAGCGCAGTCACCAAAAAAGATCTAGTGGTGAGCGCCAAGAAAGAAAACTGTGCA
GAAATTATAAGGGACGTCAAGAAAATGAAAGGGCTGGACGTCAATGCCAGAACTGTGGACTC
AGTGCTCTTGAATGGATGCAAACACCCCGTAGAGACCCTGTATATTGACGAAGCTTTTGCTT
GTCATGCAGGTACTCTCAGAGCGCTCATAGCCATTATAAGACCTAAAAAGGCAGTGCTCTGC
GGGGATCCCAAACAGTGCGGTTTTTTTAACATGATGTGCCTGAAAGTGCATTTTAACCACGA
GATTTGCACACAAGTCTTCCACAAAAGCATCTCTCGCCGTTGCACTAAATCTGTGACTTCGG
TCGTCTCAACCTTGTTTTACGACAAAAAAATGAGAACGACGAATCCGAAAGAGACTAAGATT
GTGATTGACACTACCGGCAGTACCAAACCTAAGCAGGACGATCTCATTCTCACTTGTTTCAG
AGGGTGGGTGAAGCAGTTGCAAATAGATTACAAAGGCAACGAAATAATGACGGCAGCTGCCT
CTCAAGGGCTGACCCGTAAAGGTGTGTATGCCGTTCGGTACAAGGTGAATGAAAATCCTCTG
TACGCACCCACCTCAGAACATGTGAACGTCCTACTGACCCGCACGGAGGACCGCATCGTGTG
GAAAACACTAGCCGGCGACCCATGGATAAAAACACTGACTGCCAAGTACCCTGGGAATTTCA
CTGCCACGATAGAGGAGTGGCAAGCAGAGCATGATGCCATCATGAGGCACATCTTGGAGAGA
CCGGACCCTACCGACGTCTTCCAGAATAAGGCAAACGTGTGTTGGGCCAAGGCTTTAGTGCC
GGTGCTGAAGACCGCTGGCATAGACATGACCACTGAACAATGGAACACTGTGGATTATTTTG
AAACGGACAAAGCTCACTCAGCAGAGATAGTATTGAACCAACTATGCGTGAGGTTCTTTGGA
CTCGATCTGGACTCCGGTCTATTTTCTGCACCCACTGTTCCGTTATCCATTAGGAATAATCA
CTGGGATAACTCCCCGTCGCCTAACATGTACGGGCTGAATAAAGAAGTGGTCCGTCAGCTCT
CTCGCAGGTACCCACAACTGCCTCGGGCAGTTGCCACTGGAAGAGTCTATGACATGAACACT
GGTACACTGCGCAATTATGATCCGCGCATAAACCTAGTACCTGTAAACAGAAGACTGCCTCA
```

-continued

```
TGCTTTAGTCCTCCACCATAATGAACACCCACAGAGTGACTTTTCTTCATTCGTCAGCAAAT
TGAAGGGCAGAACTGTCCTGGTGGTCGGGGAAAAGTTGTCCGTCCCAGGCAAATGGTTGAC
TGGTTGTCAGACCGGCCTGAGGCTACCTTCAGAGCTCGGCTGGATTTAGGCATCCCAGGTGA
TGTGCCCAAATATGACATAATATTTGTTAATGTGAGGACCCCATATAAATACCATCACTATC
AGCAGTGTGAAGACCATGCCATTAAGCTTAGCATGTTGACCAAGAAAGCTTGTCTGCATCTG
AATCCCGGCGGAACCTGTGTCAGCATAGGTTATGGTTACGCTGACAGGGCCAGCGAAAGCAT
CATTGGTGCTATAGCGCGGCAGTTCAAGTTTTCCCGGGTATGCAAACCGAAATCCTCACTTG
AAGAGACGGAAGTTCTGTTTGTATTCATTGGGTACGATCGCAAGGCCCGTACGCACAATTCT
TACAAGCTTTCATCAACCTTGACCAACATTTATACAGGTTCCAGACTCCACGAAGCCGGATG
TGCACCCTCATATCATGTGGTGCGAGGGGATATTGCCACGGCCACCGAAGGAGTGATTATAA
ATGCTGCTAACAGCAAAGGACAACCTGGCGGAGGGGTGTGCGGAGCGCTGTATAAGAAATTC
CCGGAAAGCTTCGATTTACAGCCGATCGAAGTAGGAAAAGCGCGACTGGTCAAAGGTGCAGC
TAAACATATCATTCATGCCGTAGGACCAAACTTCAACAAAGTTTCGGAGGTTGAAGGTGACA
AACAGTTGGCAGAGGCTTATGAGTCCATCGCTAAGATTGTCAACGATAACAATTACAAGTCA
GTAGCGATTCCACTGTTGTCCACCGGCATCTTTTCCGGGAACAAAGATCGACTAACCCAATC
ATTGAACCATTTGCTGACAGCTTTAGACACCACTGATGCAGATGTAGCCATATACTGCAGGG
ACAAGAAATGGGAAATGACTCTCAAGGAAGCAGTGGCTAGGAGAGAAGCAGTGGAGGAGATA
TGCATATCCGACGACTCTTCAGTGACAGAACCTGATGCAGAGCTGGTGAGGGTGCATCCGAA
GAGTTCTTTGGCTGGAAGGAAGGGCTACAGCACAAGCGATGGCAAAACTTTCTCATATTTGG
AAGGGACCAAGTTTCACCAGGCGGCCAAGGATATAGCAGAAATTAATGCCATGTGGCCCGTT
GCAACGGAGGCCAATGAGCAGGTATGCATGTATATCCTCGGAGAAAGCATGAGCAGTATTAG
GTCGAAATGCCCCGTCGAAGAGTCGGAAGCCTCCACACCACCTAGCACGCTGCCTTGCTTGT
GCATCCATGCCATGACTCCAGAAAGAGTACAGCGCCTAAAAGCCTCACGTCCAGAACAAATT
ACTGTGTGCTCATCCTTTCCATTGCCGAAGTATAGAATCACTGGTGTGCAGAAGATCCAATG
CTCCCAGCCTATATTGTTCTCACCGAAAGTGCCTGCGTATATTCATCCAAGGAAGTATCTCG
TGGAAACACCACCGGTAGACGAGACTCCGGAGCCATCGGCAGAGAACCAATCCACAGAGGGG
ACACCTGAACAACCACCACTTATAACCGAGGATGAGACCAGGACTAGAACGCCTGAGCCGAT
CATCATCGAAGAGGAAGAAGAGGATAGCATAAGTTTGCTGTCAGATGGCCCGACCCACCAGG
TGCTGCAAGTCGAGGCAGACATTCACGGGCCGCCCTCTGTATCTAGCTCATCCTGGTCCATT
CCTCATGCATCCGACTTTGATGTGGACAGTTTATCCATACTTGACACCCTGGAGGGAGCTAG
CGTGACCAGCGGGGCAACGTCAGCCGAGACTAACTCTTACTTCGCAAAGAGTATGGAGTTTC
TGGCGCGACCGGTGCCTGCGCCTCGAACAGTATTCAGGAACCCTCCACATCCCGCTCCGCGC
ACAAGAACACCGTCACTTGCACCCAGCAGGGCCTGCTCGAGAACCAGCCTAGTTTCCACCCC
GCCAGGCGTGAATAGGGTGATCACTAGAGAGGAGCTCGAGGCGCTTACCCCGTCACGCACTC
CTAGCAGGTCGGTCTCGAGAACCAGCCTGGTCTCCAACCCGCCAGGCGTAAATAGGGTGATT
ACAAGAGAGGAGTTTGAGGCGTTCGTAGCACAACAACAATGACGGTTTGATGCGGGTGCATA
CATCTTTTCCTCCGACACCGGTCAAGGGCATTTACAACAAAAATCAGTAAGGCAAACGGTGC
TATCCGAAGTGGTGTTGGAGAGGACCGAATTGGAGATTTCGTATGCCCCGCGCCTCGACCAA
GAAAAGAAGAATTACTACGCAAGAAATTACAGTTAAATCCCACACCTGCTAACAGAAGCAG
ATACCAGTCCAGGAAGGTGGAGAACATGAAAGCCATAACAGCTAGACGTATTCTGCAAGGCC
TAGGGCATTATTTGAAGGCAGAAGGAAAAGTGGAGTGCTACCGAACCCTGCATCCTGTTCCT
```

-continued

```
TTGTATTCATCTAGTGTGAACCGTGCCTTTTCAAGCCCCAAGGTCGCAGTGGAAGCCTGTAA

CGCCATGTTGAAAGAGAACTTTCCGACTGTGGCTTCTTACTGTATTATTCCAGAGTACGATG

CCTATTTGGACATGGTTGACGGAGCTTCATGCTGCTTAGACACTGCCAGTTTTTGCCCTGCA

AAGCTGCGCAGCTTTCCAAAGAAACACTCCTATTTGGAACCCACAATACGATCGGCAGTGCC

TTCAGCGATCCAGAACACGCTCCAGAACGTCCTGGCAGCTGCCACAAAAAGAAATTGCAATG

TCACGCAAATGAGAGAATTGCCCGTATTGGATTCGGCGGCCTTTAATGTGGAATGCTTCAAG

AAATATGCGTGTAATAATGAATATTGGGAAACGTTTAAAGAAAACCCCATCAGGCTTACTGA

AGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAG

AGAGACGTGAAAGTGACTCCAGGAACAAAACATACTGAAGAACGGCCCAAGGTACAGGTGAT

CCAGGCTGCCGATCCGCTAGCAACAGCGTATCTGTGCGGAATCCACCGAGAGCTGGTTAGGA

GATTAAATGCGGTCCTGCTTCCGAACATTCATACACTGTTTGATATGTCGGCTGAAGACTTT

GACGCTATTATAGCCGAGCACTTCCAGCCTGGGGATTGTGTTCTGGAAACTGACATCGCGTC

GTTTGATAAAAGTGAGGACGACGCCATGGCTCTGACCGCGTTAATGATTCTGGAAGACTTAG

GTGTGGACGCAGAGCTGTTGACGCTGATTGAGGCGGCTTTCGGCGAAATTTCATCAATACAT

TTGCCCACTAAAACTAAATTTAAATTCGGAGCCATGATGAAATCTGGAATGTTCCTCACACT

GTTTGTGAACACAGTCATTAACATTGTAATCGCAAGCAGAGTGTTGAGAGAACGGCTAACCG

GATCACCATGTGCAGCATTCATTGGAGATGACAATATCGTGAAAGGAGTCAAATCGGACAAA

TTAATGGCAGACAGGTGCGCCACCTGGTTGAATATGGAAGTCAAGATTATAGATGCTGTGGT

GGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGAC

GATGAACATGATGATGACAGGAGAAGGGCATTGCATGAAGAGTCAACACGCTGGAACCGAGT

GGGTATTCTTTCAGAGCTGTGCAAGGCAGTAGAATCAAGGTATGAAACCGTAGGAACTTCCA

TCATAGTTATGGCCATGACTACTCTAGCTAGCAGTGTTAAATCATTCAGCTACCTGAGAGGG

GCCCCTATAACTCTCTACGGCTAACCTGAATGGACTACGACATAGTCTAGTCCGCCAAGTCT

AGCATATGGGCGCGCCCTCAGCATCGATTGAATTGGCCACCATGGTGAGCAAGGGCGAGGAG

GATAACATGGCCATCATCAAGGAGTTCATGCGCTTCAAGGTGCACATGGAGGGCTCCGTGAA

CGGCCACGAGTTCGAGATCGAGGGCGAGGGCGAGGGCCGCCCCTACGAGGGCACCCAGACCG

CCAAGCTGAAGGTGACCAAGGGTGGCCCCCTGCCCTTCGCCTGGGACATCCTGTCCCCTCAG

TTCATGTACGGCTCCAAGGCCTACGTGAAGCACCCCGCCGACATCCCCGACTACTTGAAGCT

GTCCTTCCCCGAGGGCTTCAAGTGGGAGCGCGTGATGAACTTCGAGGACGGCGGCGTGGTGA

CCGTGACCCAGGACTCCTCCCTGCAGGACGGCGAGTTCATCTACAAGGTGAAGCTGCGCGGC

ACCAACTTCCCCTCCGACGGCCCCGTAATGCAGAAGAAGACCATGGGCTGGGAGGCCTCCTC

CGAGCGGATGTACCCCGAGGACGGCGCCCTGAAGGGCGAGATCAAGCAGAGGCTGAAGCTGA

AGGACGGCGGCCACTACGACGCTGAGGTCAAGACCACCTACAAGGCCAAGAAGCCCGTGCAG

CTGCCCGGCGCCTACAACGTCAACATCAAGTTGGACATCACCTCCCACAACGAGGACTACAC

CATCGTGGAACAGTACGAACGCGCCGAGGGCCGCCACTCCACCGGCGGCATGGACGAGCTGT

ACAAGTAGGAATTGGCAAGCTGCTTACATAGAACTCGCGGCGATTGGCATGCCGCCTTAAAA

TTTTTATTTTATTTTTCTTTTCTTTTCCGAATCGGATTTTGTTTTTAATATTTCAAAAAAAA

AAAAAAAAAAAAAAAAACGCGTCGAGGGGAATTAATTCTTGAAGACGAAAGGGCCAGGTGG
```

```
-continued
CACTTTTCGGGGAAATGTGCGCGGAACCCCTATTTGTTTATTTTTCTAAATACATTCAAATA

TGTATCCGCTCATGAGACAATAACCCTGATAAATGCTTCAATAATATTGAAAAAGGAAGAGT

ATGAGTATTCAACATTTCCGTGTCGCCCTTATTCCCTTTTTTGCGGCATTTTGCCTTCCTGT

TTTTGCTCACCCAGAAACGCTGGTGAAAGTAAAAGATGCTGAAGATCAGTTGGGTGCACGAG

TGGGTTACATCGAACTGGATCTCAACAGCGGTAAGATCCTTGAGAGTTTTCGCCCCGAAGAA

CGTTTTCCAATGATGAGCACTTTTAAAGTTCTGCTATGTGGCGCGGTATTATCCCGTGTTGA

CGCCGGGCAAGAGCAACTCGGTCGCCGCATACACTATTCTCAGAATGACTTGGTTGAGTACT

CACCAGTCACAGAAAAGCATCTTACGGATGGCATGACAGTAAGAGAATTATGCAGTGCTGCC

ATAACCATGAGTGATAACACTGCGGCCAACTTACTTCTGACAACGATCGGAGGACCGAAGGA

GCTAACCGCTTTTTTGCACAACATGGGGGATCATGTAACTCGCCTTGATCGTTGGGAACCGG

AGCTGAATGAAGCCATACCAAACGACGAGCGTGACACCACGATGCCTGTAGCAATGGCAACA

ACGTTGCGCAAACTATTAACTGGCGAACTACTTACTCTAGCTTCCCGGCAACAATTAATAGA

CTGGATGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCACTGGGG

CCAGATGGTAAGCCCTCCCGTATCGTAGTTATCTACACGACGGGGAGTCAGGCAACTATGGA

TGAACGAAATAGACAGATCGCTGAGATAGGTGCCTCACTGATTAAGCATTGGTAACTGTCAG

ACCAAGTTTACTCATATATACTTTAGATTGATTTAAAACTTCATTTTTAATTTAAAAGGATC

TAGGTGAAGATCCTTTTTGATAATCTCATGACCAAAATCCCTTAACGTGAGTTTTCGTTCCA

CTGAGCGTCAGACCCCGTAGAAAAGATCAAAGGATCTTCTTGAGATCCTTTTTTTCTGCGCG

TAATCTGCTGCTTGCAAACAAAAAAACCACCGCTACCAGCGGTGGTTTGTTTGCCGGATCAA

GAGCTACCAACTCTTTTTCCGAAGGTAACTGGCTTCAGCAGAGCGCAGATACCAAATACTGT

CCTTCTAGTGTAGCCGTAGTTAGGCCACCACTTCAAGAACTCTGTAGCACCGCCTACATACC

TCGCTCTGCTAATCCTGTTACCAGTGGCTGCTGCCAGTGGCGATAAGTCGTGTCTTACCGGG

TTGGACTCAAGACGATAGTTACCGGATAAGGCGCAGCGGTCGGGCTGAACGGGGGGTTCGTG

CACACAGCCCAGCTTGGAGCGAACGACCTACACCGAACTGAGATACCTACAGCGTGAGCATT

GAGAAAGCGCCACGCTTCCCGAAGGGAGAAAGGCGGACAGGTATCCGGTAAGCGGCAGGGTC

GGAACAGGAGAGCGCACGAGGGAGCTTCCAGGGGGAAACGCCTGGTATCTTTATAGTCCTGT

CGGGTTTCGCCACCTCTGACTTGAGCGTCGATTTTTGTGATGCTCGTCAGGGGGCGGAGCC

TATGGAAAAACGCCAGCAACGCGAGCTCTAATACGACTCACTATAG
```

The self-amplifying replicon RNA, as described herein, comprises a nucleotide sequence that is at least 80%, 85%, 90%, 91%, 92%, 93%, 94%, 95%, 96%, 97%, 98%, 99% or more identical to SEQ ID NO: 1. In some embodiments, the self-amplifying replicon RNA is at least 90% identical to SEQ ID NO: 1.

Self-amplifying RNA (replicon) is a promising new platform for gene therapy, but applications are still limited by short persistence of expression in some cell types and low levels of transgene expression in vivo. An in vitro evolution synthetic replicon RNA provides a potentially powerful strategy for modifying and enhancing replicon expression both in vitro and in vivo. Using the method of in vitro evolution, mutations were identified in nsP2 and nsP3 of Venezuelan equine encephalitis (VEE) replicon that promoted subgenomic expression in human cells.

In some embodiments, the self-amplifying replicon RNA comprises mutations that render the replicon RNA capable of expressing the IL-12 molecule at a higher level compared to the replicon RNA comprising SEQ ID NO: 1. In some embodiments, the self-amplifying replicon RNA, comprises at least one point mutation in a nucleic acid position 3936 and/or 4758 of WT replicon of SEQ ID NO: 1. In some embodiments, the self-amplifying replicon RNA, comprises at least one of the following point mutations: guanine to cytosine at position 3936 (G3936C) and adenine to guanine at position 4758 (A4758G) of WT replicon sequence of SEQ ID NO:1. The G3936C mutation would result in a glycine to arginine change at amino acid residue 1309 (G1309R). The A4758G mutation would result in a serine to glycine change at amino acid residue 1583 (S1583G). In some embodiments, the sequence of the mutant self-amplifying replicon RNA (mtReplicon RNA) is set forth in SEQ ID NO: 2 with the mutations highlighted (bold, underlined text):

(SEQ ID NO: 2)
```
ATGGGCGGCGCATGAGAGAAGCCCAGACCAATTACCTACCCAAAATGGAGAAAGTTCACGTT
GACATCGAGGAAGACAGCCCATTCCTCAGAGCTTTGCAGCGGAGCTTCCCGCAGTTTGAGGT
AGAAGCCAAGCAGGTCACTGATAATGACCATGCTAATGCCAGAGCGTTTTCGCATCTGGCTT
CAAAACTGATCGAAACGGAGGTGGACCCATCCGACACGATCCTTGACATTGGAAGTGCGCCC
GCCCGCAGAATGTATTCTAAGCACAAGTATCATTGTATCTGTCCGATGAGATGTGCGGAAGA
TCCGGACAGATTGTATAAGTATGCAACTAAGCTGAAGAAAAACTGTAAGGAAATAACTGATA
AGGAATTGGACAAGAAAATGAAGGAGCTGGCCGCCGTCATGAGCGACCCTGACCTGGAAACT
GAGACTATGTGCCTCCACGACGACGAGTCGTGTCGCTACGAAGGGCAAGTCGCTGTTTACCA
GGATGTATACGCGGTTGACGGACCGACAAGTCTCTATCACCAAGCCAATAAGGGAGTTAGAG
TCGCCTACTGGATAGGCTTTGACACCACCCCTTTTATGTTTAAGAACTTGGCTGGAGCATAT
CCATCATACTCTACCAACTGGGCCGACGAAACCGTGTTAACGGCTCGTAACATAGGCCTATG
CAGCTCTGACGTTATGGAGCGGTCACGTAGAGGGATGTCCATTCTTAGAAAGAAGTATTTGA
AACCATCCAACAATGTTCTATTCTCTGTTGGCTCGACCATCTACCACGAGAAGAGGGACTTA
CTGAGGAGCTGGCACCTGCCGTCTGTATTTCACTTACGTGGCAAGCAAAATTACACATGTCG
GTGTGAGACTATAGTTAGTTGCGACGGGTACGTCGTTAAAAGAATAGCTATCAGTCCAGGCC
TGTATGGGAAGCCTTCAGGCTATGCTGCTACGATGCACCGCGAGGGATTCTTGTGCTGCAAA
GTGACAGACACATTGAACGGGAGAGGGTCTCTTTTCCCGTGTGCACGTATGTGCCAGCTAC
ATTGTGTGACCAAATGACTGGCATACTGGCAACAGATGTCAGTGCGACGACGCGCAAAAAC
TGCTGGTTGGGCTCAACCAGCGTATAGTCGTCAACGGTCGCACCCAGAGAAACACCAATACC
ATGAAAAATTACCTTTTGCCCGTAGTGGCCCAGGCATTTGCTAGGTGGGCAAAGGAATATAA
GGAAGATCAAGAAGATGAAAGGCCACTAGGACTACGAGATAGACAGTTAGTCATGGGGTGTT
GTTGGGCTTTTAGAAGGCACAAGATAACATCTATTTATAAGCGCCCGGATACCCAAACCATC
ATCAAAGTGAACAGCGATTTCCACTCATTCGTGCTGCCCAGGATAGGCAGTAACACATTGGA
GATCGGGCTGAGAACAAGAATCAGGAAAATGTTAGAGGAGCACAAGGAGCCGTCACCTCTCA
TTACCGCCGAGGACGTACAAGAAGCTAAGTGCGCAGCCGATGAGGCTAAGGAGGTGCGTGAA
GCCGAGGAGTTGCGCGCAGCTCTACCACCTTTGGCAGCTGATGTTGAGGAGCCCACTCTGGA
GGCAGACGTCGACTTGATGTTACAAGAGGCTGGGGCCGGCTCAGTGGAGACACCTCGTGGCT
TGATAAAGGTTACCAGCTACGATGGCGAGGACAAGATCGGCTCTTACGCTGTGCTTTCTCCG
CAGGCTGTACTCAAGAGTGAAAAATTATCTTGCATCCACCCTCTCGCTGAACAAGTCATAGT
GATAACACACTCTGGCCGAAAAGGGCGTTATGCCGTGGAACCATACCATGGTAAAGTAGTGG
TGCCAGAGGGACATGCAATACCCGTCCAGGACTTTCAAGCTCTGAGTGAAAGTGCCACCATT
GTGTACAACGAACGTGAGTTCGTAAACAGGTACCTGCACCATATTGCCACACATGGAGGAGC
GCTGAACACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGGCTCACA
GGCGAGCTGGTGGATCCTCCCTTCCATGAATTCGCCTACGAGAGTCTGAGAACACGACCAGC
CGCTCCTTACCAAGTACCAACCATAGGGGTGTATGGCGTGCCAGGATCAGGCAAGTCTGGCA
TCATTAAAAGCGCAGTCACCAAAAAAGATCTAGTGGTGAGCGCCAAGAAAGAAACTGTGCA
GAAATTATAAGGGACGTCAAGAAAATGAAAGGGCTGGACGTCAATGCCAGAACTGTGGACTC
AGTGCTCTTGAATGGATGCAAACACCCCGTAGAGACCCTGTATATTGACGAAGCTTTTGCTT
GTCATGCAGGTACTCTCAGAGCGCTCATAGCCATTATAAGACCTAAAAAGGCAGTGCTCTGC
```

-continued

```
GGGGATCCCAAACAGTGCGGTTTTTTTAACATGATGTGCCTGAAAGTGCATTTTAACCACGA

GATTTGCACACAAGTCTTCCACAAAAGCATCTCTCGCCGTTGCACTAAATCTGTGACTTCGG

TCGTCTCAACCTTGTTTTACGACAAAAAAATGAGAACGACGAATCCGAAAGAGACTAAGATT

GTGATTGACACTACCGGCAGTACCAAACCTAAGCAGGACGATCTCATTCTCACTTGTTTCAG

AGGGTGGGTGAAGCAGTTGCAAATAGATTACAAAGGCAACGAAATAATGACGGCAGCTGCCT

CTCAAGGGCTGACCCGTAAAGGTGTGTATGCCGTTCGGTACAAGGTGAATGAAAATCCTCTG

TACGCACCCACCTCAGAACATGTGAACGTCCTACTGACCCGCACGGAGGACCGCATCGTGTG

GAAAACACTAGCCGGCGACCCATGGATAAAAACACTGACTGCCAAGTACCCTGGGAATTTCA

CTGCCACGATAGAGGAGTGGCAAGCAGAGCATGATGCCATCATGAGGCACATCTTGGAGAGA

CCGGACCCTACCGACGTCTTCCAGAATAAGGCAAACGTGTGTTGGGCCAAGGCTTTAGTGCC

GGTGCTGAAGACCGCTGGCATAGACATGACCACTGAACAATGGAACACTGTGGATTATTTTG

AAACGGACAAAGCTCACTCAGCAGAGATAGTATTGAACCAACTATGCGTGAGGTTCTTTGGA

CTCGATCTGGACTCCGGTCTATTTTCTGCACCCACTGTTCCGTTATCCATTAGGAATAATCA

CTGGGATAACTCCCCGTCGCCTAACATGTACGGGCTGAATAAAGAAGTGGTCCGTCAGCTCT

CTCGCAGGTACCCACAACTGCCTCGGGCAGTTGCCACTGGAAGAGTCTATGACATGAACACT

GGTACACTGCGCAATTATGATCCGCGCATAAACCTAGTACCTGTAAACAGAAGACTGCCTCA

TGCTTTAGTCCTCCACCATAATGAACACCCACAGAGTGACTTTTCTTCATTCGTCAGCAAAT

TGAAGGGCAGAACTGTCCTGGTGGTCGGGGAAAAGTTGTCCGTCCCAGGCAAAATGGTTGAC

TGGTTGTCAGACCGGCCTGAGGCTACCTTCAGAGCTCGGCTGGATTTAGGCATCCCAGGTGA

TGTGCCCAAATATGACATAATATTTGTTAATGTGAGGACCCCATATAAATACCATCACTATC

AGCAGTGTGAAGACCATGCCATTAAGCTTAGCATGTTGACCAAGAAAGCTTGTCTGCATCTG

AATCCCGGCGGAACCTGTGTCAGCATAGGTTATGGTTACGCTGACAGGGCCAGCGAAAGCAT

CATTGGTGCTATAGCGCGGCAGTTCAAGTTTTCCCGGGTATGCAAACCGAAATCCTCACTTG

AAGAGACGGAAGTTCTGTTTGTATTCATTCGGTACGATCGCAAGGCCCGTACGCACAATTCT

TACAAGCTTTCATCAACCTTGACCAACATTTATACAGGTTCCAGACTCCACGAAGCCGGATG

TGCACCCTCATATCATGTGGTGCGAGGGGATATTGCCACGGCCACCGAAGGAGTGATTATAA

ATGCTGCTAACAGCAAAGGACAACCTGGCGGAGGGGTGTGCGGAGCGCTGTATAAGAAATTC

CCGGAAAGCTTCGATTTACAGCCGATCGAAGTAGGAAAAGCGCGACTGGTCAAAGGTGCAGC

TAAACATATCATTCATGCCGTAGGACCAAACTTCAACAAAGTTTCGGAGGTTGAAGGTGACA

AACAGTTGGCAGAGGCTTATGAGTCCATCGCTAAGATTGTCAACGATAACAATTACAAGTCA

GTAGCGATTCCACTGTTGTCCACCGGCATCTTTTCCGGGAACAAAGATCGACTAACCCAATC

ATTGAACCATTTGCTGACAGCTTTAGACACCACTGATGCAGATGTAGCCATATACTGCAGGG

ACAAGAAATGGGAAATGACTCTCAAGGAAGCAGTGGCTAGGAGAGAAGCAGTGGAGGAGATA

TGCATATCCGACGACTCTTCAGTGACAGAACCTGATGCAGAGCTGGTGAGGGTGCATCCGAA

GAGTTCTTTGGCTGGAAGGAAGGGCTACAGCACAAGCGATGGCAAAACTTTCTCATATTTGG

AAGGGACCAAGTTTCACCAGGCGGCCAAGGATATAGCAGAAATTAATGCCATGTGGCCCGTT

GCAACGGAGGCCAATGAGCAGGTATGCATGTATATCCTCGGAGAAGGCATGAGCAGTATTAG

GTCGAAATGCCCCGTCGAAGAGTCGGAAGCCTCCACACCACCTAGCACGCTGCCTTGCTTGT

GCATCCATGCCATGACTCCAGAAAGAGTACAGCGCCTAAAAGCCTCACGTCCAGAACAAATT

ACTGTGTGCTCATCCTTTCCATTGCCGAAGTATAGAATCACTGGTGTGCAGAAGATCCAATG

CTCCCAGCCTATATTGTTCTCACCGAAAGTGCCTGCGTATATTCATCCAAGGAAGTATCTCG
```

-continued

```
TGGAAACACCACCGGTAGACGAGACTCCGGAGCCATCGGCAGAGAACCAATCCACAGAGGGG

ACACCTGAACAACCACCACTTATAACCGAGGATGAGACCAGGACTAGAACGCCTGAGCCGAT

CATCATCGAAGAGGAAGAAGAGGATAGCATAAGTTTGCTGTCAGATGGCCCGACCCACCAGG

TGCTGCAAGTCGAGGCAGACATTCACGGGCCGCCCTCTGTATCTAGCTCATCCTGGTCCATT

CCTCATGCATCCGACTTTGATGTGGACAGTTTATCCATACTTGACACCCTGGAGGGAGCTAG

CGTGACCAGCGGGGCAACGTCAGCCGAGACTAACTCTTACTTCGCAAAGAGTATGGAGTTTC

TGGCGCGACCGGTGCCTGCGCCTCGAACAGTATTCAGGAACCCTCCACATCCCGCTCCGCGC

ACAAGAACACCGTCACTTGCACCCAGCAGGGCCTGCTCGAGAACCAGCCTAGTTTCCACCCC

GCCAGGCGTGAATAGGGTGATCACTAGAGAGGAGCTCGAGGCGCTTACCCCGTCACGCACTC

CTAGCAGGTCGGTCTCGAGAACCAGCCTGGTCTCCAACCCGCCAGGCGTAAATAGGGTGATT

ACAAGAGAGGAGTTTGAGGCGTTCGTAGCACAACAACAATGACGGTTTGATGCGGGTGCATA

CATCTTTTCCTCCGACACCGGTCAAGGGCATTTACAACAAAAATCAGTAAGGCAAACGGTGC

TATCCGAAGTGGTGTTGGAGAGGACCGAATTGGAGATTTCGTATGCCCCGCGCCTCGACCAA

GAAAAAGAAGAATTACTACGCAAGAAATTACAGTTAAATCCCACACCTGCTAACAGAAGCAG

ATACCAGTCCAGGAAGGTGGAGAACATGAAAGCCATAACAGCTAGACGTATTCTGCAAGGCC

TAGGGCATTATTTGAAGGCAGAAGGAAAAGTGGAGTGCTACCGAACCCTGCATCCTGTTCCT

TTGTATTCATCTAGTGTGAACCGTGCCTTTTCAAGCCCCAAGGTCGCAGTGGAAGCCTGTAA

CGCCATGTTGAAAGAGAACTTTCCGACTGTGGCTTCTTACTGTATTATTCCAGAGTACGATG

CCTATTTGGACATGGTTGACGGAGCTTCATGCTGCTTAGACACTGCCAGTTTTTGCCCTGCA

AAGCTGCGCAGCTTTCCAAAGAAACACTCCTATTTGGAACCCACAATACGATCGGCAGTGCC

TTCAGCGATCCAGAACACGCTCCAGAACGTCCTGGCAGCTGCCACAAAAAGAAATTGCAATG

TCACGCAAATGAGAGAATTGCCCGTATTGGATTCGGCGGCCTTTAATGTGGAATGCTTCAAG

AAATATGCGTGTAATAATGAATATTGGGAAACGTTTAAAGAAAACCCCATCAGGCTTACTGA

AGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAG

AGAGACGTGAAAGTGACTCCAGGAACAAAACATACTGAAGAACGGCCCAAGGTACAGGTGAT

CCAGGCTGCCGATCCGCTAGCAACAGCGTATCTGTGCGGAATCCACCGAGAGCTGGTTAGGA

GATTAAATGCGGTCCTGCTTCCGAACATTCATACACTGTTTGATATGTCGGCTGAAGACTTT

GACGCTATTATAGCCGAGCACTTCCAGCCTGGGGATTGTGTTCTGGAAACTGACATCGCGTC

GTTTGATAAAAGTGAGGACGACGCCATGGCTCTGACCGCGTTAATGATTCTGGAAGACTTAG

GTGTGGACGCAGAGCTGTTGACGCTGATTGAGGCGGCTTTCGGCGAAATTTCATCAATACAT

TTGCCCACTAAAACTAAATTTAAATTCGGAGCCATGATGAAATCTGGAATGTTCCTCACACT

GTTTGTGAACACAGTCATTAACATTGTAATCGCAAGCAGAGTGTTGAGAGAACGGCTAACCG

GATCACCATGTGCAGCATTCATTGGAGATGACAATATCGTGAAAGGAGTCAAATCGGACAAA

TTAATGGCAGACAGGTGCGCCACCTGGTTGAATATGGAAGTCAAGATTATAGATGCTGTGGT

GGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGAC

GATGAACATGATGATGACAGGAGAAGGGCATTGCATGAAGAGTCAACACGCTGGAACCGAGT

GGGTATTCTTTCAGAGCTGTGCAAGGCAGTAGAATCAAGGTATGAAACCGTAGGAACTTCCA

TCATAGTTATGGCCATGACTACTCTAGCTAGCAGTGTTAAATCATTCAGCTACCTGAGAGGG
```

-continued

```
GCCCCTATAACTCTCTACGGCTAACCTGAATGGACTACGACATAGTCTAGTCCGCCAAGTCT
AGCATATGGGCGCGCCCTCAGCATCGATTGAATTGGCCACCATGGTGAGCAAGGGCGAGGAG
GATAACATGGCCATCATCAAGGAGTTCATGCGCTTCAAGGTGCACATGGAGGGCTCCGTGAA
CGGCCACGAGTTCGAGATCGAGGGCGAGGGCGAGGGCCGCCCCTACGAGGGCACCCAGACCG
CCAAGCTGAAGGTGACCAAGGGTGGCCCCCTGCCCTTCGCCTGGGACATCCTGTCCCCTCAG
TTCATGTACGGCTCCAAGGCCTACGTGAAGCACCCCGCCGACATCCCCGACTACTTGAAGCT
GTCCTTCCCCGAGGGCTTCAAGTGGGAGCGCGTGATGAACTTCGAGGACGGCGGCGTGGTGA
CCGTGACCCAGGACTCCTCCCTGCAGGACGGCGAGTTCATCTACAAGGTGAAGCTGCGCGGC
ACCAACTTCCCCTCCGACGGCCCCGTAATGCAGAAGAAGACCATGGGCTGGGAGGCCTCCTC
CGAGCGGATGTACCCCGAGGACGGCGCCCTGAAGGGCGAGATCAAGCAGAGGCTGAAGCTGA
AGGACGGCGGCCACTACGACGCTGAGGTCAAGACCACCTACAAGGCCAAGAAGCCCGTGCAG
CTGCCCGGCGCCTACAACGTCAACATCAAGTTGGACATCACCTCCCACAACGAGGACTACAC
CATCGTGGAACAGTACGAACGCGCCGAGGGCCGCCACTCCACCGGCGGCATGGACGAGCTGT
ACAAGTAGGAATTGGCAAGCTGCTTACATAGAACTCGCGGCGATTGGCATGCCGCCTTAAAA
TTTTTATTTTATTTTTCTTTTCTTTTCCGAATCGGATTTTGTTTTTAATATTTCAAAAAAAA
AAAAAAAAAAAAAAAAAACGCGTCGAGGGGAATTAATTCTTGAAGACGAAAGGGCCAGGTGG
CACTTTTCGGGGAAATGTGCGCGGAACCCCTATTTGTTTATTTTTCTAAATACATTCAAATA
TGTATCCGCTCATGAGACAATAACCCTGATAAATGCTTCAATAATATTGAAAAAGGAAGAGT
ATGAGTATTCAACATTTCCGTGTCGCCCTTATTCCCTTTTTTGCGGCATTTTGCCTTCCTGT
TTTTGCTCACCCAGAAACGCTGGTGAAAGTAAAAGATGCTGAAGATCAGTTGGGTGCACGAG
TGGGTTACATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCCGTGTTGA
CGCCGGGCAAGAGCAACTCGGTCGCCGCATACACTATTCTCAGAATGACTTGGTTGAGTACT
CACCAGTCACAGAAAAGCATCTTACGGATGGCATGACAGTAAGAGAATTATGCAGTGCTGCC
ATAACCATGAGTGATAACACTGCGGCCAACTTACTTCTGACAACGATCGGAGGACCGAAGGA
GCTAACCGCTTTTTTGCACAACATGGGGGATCATGTAACTCGCCTTGATCGTTGGGAACCGG
AGCTGAATGAAGCCATACCAAACGACGAGCGTGACACCACGATGCCTGTAGCAATGGCAACA
ACGTTGCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGGCTGGT
TTATTGCTGATAAATCTGGAGCCGGTGAGCGTGGGTCTCGCGGTATCATTGCAGCACTGGGG
CCAGATGGTAAGCCCTCCCGTATCGTAGTTATCTACACGACGGGGAGTCAGGCAACTATGGA
TGAACGAAATAGACAGATCGCTGAGATAGGTGCCTCACTGATTAAGCATTGGTAACTGTCAG
ACCAAGTTTACTCATATATACTTTAGATTGATTTAAAACTTCATTTTTAATTTAAAAGGATC
TAGGTGAAGATCCTTTTTGATAATCTCATGACCAAAATCCCTTAACGTGAGTTTTCGTTCCA
CTGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACTGT
CCTTCTAGTGTAGCCGTAGTTAGGCCACCACTTCAAGAACTCTGTAGCACCGCCTACATACC
TCGCTCTGCTAATCCTGTTACCAGTGGCTGCTGCCAGTGGCGATAAGTCGTGTCTTACCGGG
TTGGACTCAAGACGATAGTTACCGGATAAGGCGCAGCGGTCGGGCTGAACGGGGGGTTCGTG
CACACAGCCCAGCTTGGAGCGAACGACCTACACCGAACTGAGATACCTACAGCGTGAGCATT
```

-continued

```
GAGAAAGCGCCACGCTTCCCGAAGGGAGAAAGGCGGACAGGTATCCGGTAAGCGGCAGGGTC

GGAACAGGAGAGCGCACGAGGGAGCTTCCAGGGGGAAACGCCTGGTATCTTTATAGTCCTGT

CGGGTTTCGCCACCTCTGACTTGAGCGTCGATTTTTGTGATGCTCGTCAGGGGGCGGAGCC

TATGGAAAAACGCCAGCAACGCGAGCTCTAATACGACTCACTATAG
```

In other embodiments, the self-amplifying replicon RNA is derived from a Hepatitis C virus (HCV). HCV are part of the Group IV Flaviviridae family of viruses, possessing monopartite, linear, single-stranded RNA genomes of positive polarity, 9.6 to 12.3 kilobase in length. The 5'-termini of flaviviruses carry a methylated nucleotide cap, while other members of this family are uncapped and encode an internal ribosome entry site.

In other embodiments, the alphavirus is a SF virus. The SF virus is a viral pathogen typically carried by mosquitos that causes encephalitis. The Semliki Forest virus is a positive-stranded RNA virus with a genome of approximately 13,000 base pairs which encodes nine proteins. The 5' two thirds of the genome encode four non-structural proteins concerned with RNA synthesis and the structural proteins are encoded in the 3' third. Of the structural proteins, the C proteins makes up the icosahedral capsid which is enveloped by a lipid bilayer, derived from the host cell. The outermost surface of the virus is almost entirely covered by heterodimers of glycoproteins E1 and E2, arranged in inter-connective trimers, which form an outer shell. Trimers are anchored in the membrane by an E2 cytoplasmic domain that associates with the nucleocapsid.

In other embodiments, the alphavirus is a SIN virus. The virus is transmitted by mosquitoes. SIN virus causes Sindbis fever in humans and the symptoms include arthralgia, rash and malaise. Sindbis viruses are enveloped particles with an icosahedral capsid. Its genome is a single stranded RNA approximately 11.7 kb long. It has a 5' cap and 3' polyadenylated tail therefore serves directly as messenger RNA (mRNA) in a host cell. The genome encodes four non-structural proteins at the 5' end and the capsid and two envelope proteins at the 3' end. This is characteristic of all Togaviruses. Replication is cytoplasmic and rapid. The genomic RNA is partially translated at the 5' end to produce the non-structural proteins which are then involved in genome replication and the production of new genomic RNA and a shorter sub-genomic RNA strand. This sub-genomic strand is translated into the structural proteins. The viruses assemble at the host cell surfaces and acquire their envelope through budding. A non-coding RNA element has been found to be essential for Sindbis virus genome replication.

The viral replicon RNA, is capable of stimulating immune response via toll like receptors (TLRs). A subset of TLRs, TLR3, TLR7/8, and TLR9, is involved in antiviral responses by triggering the production of antiviral cytokines such as type I interferons (IFNs). TLR3 responds to double stranded RNA, a replication intermediary for many viruses. TLR7/8 recognize viral single-stranded RNAs, whereas TLR9 recognizes unmethylated CpG motifs within viral DNA. TLRs involved in virus recognition are expressed on endosomal membranes and can be separated according to their requirement for the adaptor protein MyD88: TLR3 activity is MyD88-independent while TLRs7/8/9 depend on MyD88. The activation of TLR3 leads to the production of Type I Interferon (IFN). Type-I interferon signaling through ISGF3 (STAT1/STAT2/IRF9) complex is required for sustained Rip3 activation and necroptosis.

In some embodiments, the LNP-replicon RNA are capable of stimulating TLR3 signaling in tumor cells, which leads to necrotic cell death of tumor cells. In some embodiments, the LNP-replicon RNA can enhance the immunogenic cell death (ICD) induced by the LNPs. In some embodiments, TT3-LNP-Replicon RNA can exert tumor inhibition by synergistically induce ICD in tumor cells and trigger an anti-tumor immune response (e.g., recruiting of immune cells such as granulocytes, monocytes, macrophages, myeloid derived suppressive cells, dendritic cells, T cells, and NK cells). In some embodiments, the synthetic oncolytic virus comprises TT3-LNP-mtReplicon RNA.

In some embodiments, the replicon RNA comprises a coding sequence for a detectable molecule in the subgenomic region. In some embodiments, the detectable molecule is a nucleic acid or a polypeptide. In some embodiments, the polypeptide is a fluorescent protein. Fluorescent proteins are known in the art, and are a subclass of fluorophores, which are fluorescent chemical compounds with the ability to re-emit light upon excitation. The fluorophore will absorb excitation light energy of a first specific wavelength, and then will re-emit light energy at a second, longer specific wavelength. Each type of fluorophore responds to and emits differing wavelengths of light, depending on the nature of its chemical structure and environment. In some embodiments, the fluorescent protein includes, but is not limited to, wt-GFP, green fluorescent protein (e.g., EGFP, Emerald, Superfolder GFP, Azami Green, mWasabi, TagGFP, TurboGFP, AcGFP, ZsGreen, T-Sapphire, etc.), blue fluorescent protein, (e.g., EBFP, EBFP2, Azurite, mTagBFP, etc.), cyan fluorescent protein (e.g., ECFP, mECFP, Cerulean, mTurquoise, CyPet, AmCyan1, Midori-Ishi Cyan, TagCFP, mTFP1 (Teal), etc.), yellow fluorescent protein (e.g., EYFP, Topaz, Venus, mCitrine, YPet, TagYFP, PhiYFP, ZsYellow1, mBanana, etc.), orange fluorescent protein (e.g., Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, etc.), or red fluorescent protein (e.g., mRuby, mApple, mStrawberry, AsRed2, mRFP1, JRed, mCherry, HcRed1, mRaspberry, dKeima-Tandem, HcRed-Tandem, mPlum, AQ143, etc.).

In some aspects, as described herein, the self-amplifying replicon RNA comprises a coding sequence for expression of IL-12 in the subgenomic region. An exemplary coding sequence for IL-12 is set forth in SEQ ID NO: 3:

(SEQ ID NO: 3)
```
ATGAGGGTCCCCGCTCAGCTCCTGGGGCTCCTGCTGCTCTGGCTCCCAGGTGCACGATGTGC

CATGTGGGAGCTGGAGAAAGACGTTTATGTTGTAGAGGTGGACTGGACTCCCGATGCCCCTG

GAGAAACAGTGAACCTCACCTGTGACACGCCTGAAGAAGATGACATCACCTGGACCTCAGAC

CAGAGACATGGAGTCATAGGCTCTGGAAAGACCCTGACCATCACTGTCAAAGAGTTTCTAGA

TGCTGGCCAGTACACCTGCCACAAAGGAGGCGAGACTCTGAGCCACTCACATCTGCTGCTCC

ACAAGAAGGAAAATGGAATTTGGTCCACTGAAATTTTAAAAAATTTCAAAAACAAGACTTTC

CTGAAGTGTGAAGCACCAAATTACTCCGGACGGTTCACGTGCTCATGGCTGGTGCAAAGAAA

CATGGACTTGAAGTTCAACATCAAGAGCAGTAGCAGTTCCCCTGACTCTCGGGCAGTGACAT

GTGGAATGGCGTCTCTGTCTGCAGAGAAGGTCACACTGGACCAAAGGGACTATGAGAAGTAT

TCAGTGTCCTGCCAGGAGGATGTCACCTGCCCAACTGCCGAGGAGACCCTGCCCATTGAACT

GGCGTTGGAAGCACGGCAGCAGAATAAATATGAGAACTACAGCACCAGCTTCTTCATCAGGG

ACATCATCAAACCAGACCCGCCCAAGAACTTGCAGATGAAGCCTTTGAAGAACTCACAGGTG

GAGGTCAGCTGGGAGTACCCTGACTCCTGGAGCACTCCCCATTCCTACTTCTCCCTCAAGTT

CTTTGTTCGAATCCAGCGCAAGAAAGAAAAGATGAAGGAGACAGAGGAGGGGTGTAACCAGA

AAGGTGCGTTCCTCGTAGAGAAGACATCTACCGAAGTCCAATGCAAAGGCGGGAATGTCTGC

GTGCAAGCTCAGGATCGCTATTACAATTCCTCATGCAGCAAGTGGGCATGTGTTCCCTGCAG

GGTCCGATCCGGAGGTTCCGGTGGTGGATCCGGAGGTGGCTCCGGCGGCGGATCCAGGGTCA

TTCCAGTCTCTGGACCTGCCAGGTGTCTTAGCCAGTCCCGAAACCTGCTGAAGACCACAGAT

GACATGGTGAAGACGGCCAGAGAAAAACTGAAACATTATTCCTGCACTGCTGAAGACATCGA

TCATGAAGACATCACACGGGACCAAACCAGCACATTGAAGACCTGTTTACCACTGGAACTAC

ACAAGAACGAGAGTTGCCTGGCTACTAGAGAGACTTCTTCCACAACAAGAGGGAGCTGCCTG

CCCCCACAGAAGACGTCTTTGATGATGACCCTGTGCCTTGGTAGCATCTATGAGGACTTGAA

GATGTACCAGACAGAGTTCCAGGCCATCAACGCAGCACTTCAGAATCACAACCATCAGCAGA

TCATTCTAGACAAGGGCATGCTGGTGGCCATCGATGAGCTGATGCAGTCTCTGAATCATAAT

GGCGAGACTCTGCGCCAGAAACCTCCTGTGGGAGAAGCAGACCCTTACAGAGTGAAAATGAA

GCTCTGCATCCTGCTTCACGCCTTCAGCACCCGCGTCGTGACCATCAACAGGGTGATGGGCT

ATCTGAGCTCCGCCTGA
```

Structurally, IL-12 belongs to type I cytokines and has a four α-helical bundle structure. IL-12 acts in a form of a heterodimeric protein (IL-12-p70; IL-12-p30/p40) consisting of two covalently linked p30 and p40 subunits. Contrary to the heterodimeric form, IL-12-p40/p40 homodimer acts mostly as a competitive suppressant of IL-12-p70 actions. IL-12 is a pleiotropic cytokine, the actions of which create an interconnection between the innate and adaptive immunity. IL-12 was first described as a factor secreted from PMA-induced EBV-transformed B-cell lines. Based on its actions, IL-12 was initially designated as "cytotoxic lymphocyte maturation factor" and "natural killer cell stimulatory factor". Due to bridging the innate and adaptive immunity and potently stimulating the production of IFN-γ, a cytokine coordinating natural mechanisms of anticancer defense, IL-12 seemed an ideal candidate for tumor immunotherapy in humans. However, severe side effects associated with systemic administration of IL-12 in clinical investigations and the very narrow therapeutic index of this cytokine markedly tempered enthusiasm for the use of this cytokine in cancer patients.

Following the discovery of IL-12, three other members (IL-23, IL-27, and IL-35) have been added to the IL-12 family and shown to play critical roles in Th1 cell functions. IL-12 is a ligand of a receptor composed of two amino acid chains, IL-12R-β1 and IL-12R-β2. IL-12 receptor is expressed in a constitutive (e.g., IL-12R-β1 in B cells) or inducible (IL-12R-β2) manner in a variety of immune cells, including NK cells, T, and B lymphocytes. Ligand-bound IL-12R-β2 becomes phosphorylated on tyrosines, which provides harboring sites for two kinases, JAK2 and TYK2. Among the STAT family of transcription factors, STAT4 is considered to be the most specific mediator of cellular responses elicited by IL-12. The main elements of IL-12 actions are as follows: increasing production of IFN-γ, which is the most potent mediator of IL-12 actions, from NK and T cells; stimulation of growth and cytotoxicity of activated NK cells, CD8+ and CD4+ T cells, shifting differentiation of CD4+ Th0 cells toward the Th1 phenotype; enhancement of antibody-dependent cellular cytotoxicity (ADCC) against tumor cells; and the induction of IgG and suppression of IgE production from B cells. The main source of IL-12 in humans is the activated antigen-presenting cells, such as dendritic cells, especially of the CD1c+ phenotype, as well as the hematopoietic phagocytes (monocytes, macrophages, and also neutrophils), but IL-12 can also be produced by other cell types. While IL-12 acts on a variety of immune cells, the overall physiological role for IL-12 seems to be orchestrating the Th1-type immune response against certain pathogens.

The present disclosure, in some aspect, describes local delivery of IL-12 by a LNP encapsulated viral replicon RNA, which encodes an IL-12 molecule in its subgenomic region. In addition to the synergistic tumor cell immunogenic cell death (ICD) induced by the LNP-replicon RNA, in some embodiments, the expression of IL12 in the tumor microenvironment can lead to further immunostimulation and results in an enhancement of anti-tumor immune response. In some embodiments, the combination of LNP-replicon RNA-IL-12 in the tumor microenvironment is capable of induce a systemic anti-tumor immune response. In other embodiments, the combination of LNP-replicon RNA-IL-12 in the tumor microenvironment is capable of eradicate the tumor cells and prevent the recurrence of the tumor. In some embodiments, the synthetic oncolytic virus comprises TT3-LNP-mtReplicon RNA-IL12.

In some embodiments, the replicon RNA-IL12 further comprises a coding sequence for serum albumin. The half-life of peptides and proteins (e.g., cytokines) in a biological environment (e.g., serum, tumor microenvironment) is affected by several factors, including size, charge, proteolytic sensitivity, nature of their biology, turnover rate of proteins they bind, and other factors. In some cases, the half-life of proteins in biological environment can be roughly correlated with their size. Peptides and proteins smaller than approximately 70 kDa (e.g., cytokines) can be eliminated via kidney filtration, so they generally possess very short half-lives. Larger proteins, however, may persist for several days. Three types of proteins, IgGs, serum albumin, and transferrin, persist for much longer than would be predicted just by their size. In some embodiments, the serum albumin is human serum albumin. In some embodiments, the serum albumin is mouse serum albumin (MSA). An exemplary coding sequence for replicon RNA-IL12-MSA is set forth in SEQ ID NO: 4:

```
(SEQ ID NO: 4)
ATGGGCGGCGCATGAGAGAAGCCCAGACCAATTACCTACCCAAAATGGAGAAAGTTCACGTT

GACATCGAGGAAGACAGCCCATTCCTCAGAGCTTTGCAGCGGAGCTTCCCGCAGTTTGAGGT

AGAAGCCAAGCAGGTCACTGATAATGACCATGCTAATGCCAGAGCGTTTTCGCATCTGGCTT

CAAAACTGATCGAAACGGAGGTGGACCCATCCGACACGATCCTTGACATTGGAAGTGCGCCC

GCCCGCAGAATGTATTCTAAGCACAAGTATCATTGTATCTGTCCGATGAGATGTGCGGAAGA

TCCGGACAGATTGTATAAGTATGCAACTAAGCTGAAGAAAAACTGTAAGGAAATAACTGATA

AGGAATTGGACAAGAAAATGAAGGAGCTGGCCGCCGTCATGAGCGACCCTGACCTGGAAACT

GAGACTATGTGCCTCCACGACGACGAGTCGTGTCGCTACGAAGGGCAAGTCGCTGTTTACCA

GGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATAT

CCATCATACTCTACCAACTGGGCCGACGAAACCGTGTTAACGGCTCGTAACATAGGCCTATG

CAGCTCTGACGTTATGGAGCGGTCACGTAGAGGGATGTCCATTCTTAGAAAGAAGTATTTGA

AACCATCCAACAATGTTCTATTCTCTGTTGGCTCGACCATCTACCACGAGAAGAGGGACTTA

CTGAGGAGCTGGCACCTGCCGTCTGTATTTCACTTACGTGGCAAGCAAAATTACACATGTCG

GTGTGAGACTATAGTTAGTTGCGACGGGTACGTCGTTAAAAGAATAGCTATCAGTCCAGGCC

TGTATGGGAAGCCTTCAGGCTATGCTGCTACGATGCACCGCGAGGGATTCTTGTGCTGCAAA

GTGACAGACACATTGAACGGGGAGAGGGTCTCTTTTCCCGTGTGCACGTATGTGCCAGCTAC

ATTGTGTGACCAAATGACTGGCATACTGGCAACAGATGTCAGTGCGGACGACGCGCAAAAAC

TGCTGGTTGGGCTCAACCAGCGTATAGTCGTCAACGGTCGCACCCAGAGAAACACCAATACC

ATGAAAAATTACCTTTTGCCCGTAGTGGCCCAGGCATTTGCTAGGTGGGCAAAGGAATATAA

GGAAGATCAAGAAGATGAAAGGCCACTAGGACTACGAGATAGACAGTTAGTCATGGGGTGTT

GTTGGGCTTTTAGAAGGCACAAGATAACATCTATTTATAAGCGCCCGGATACCCAAACCATC

ATCAAAGTGAACAGCGATTTCCACTCATTCGTGCTGCCCAGGATAGGCAGTAACACATTGGA

GATCGGGCTGAGAACAAGAATCAGGAAAATGTTAGAGGAGCACAAGGAGCCGTCACCTCTCA

TTACCGCCGAGGACGTACAAGAAGCTAAGTGCGCAGCCGATGAGGCTAAGGAGGTGCGTGAA

GCCGAGGAGTTGCGCGCAGCTCTACCACCTTTGGCAGCTGATGTTGAGGAGCCCACTCTGGA
```

-continued

```
AGCCGATGTCGACTTGATGTTACAAGAGGCTGGGGCCGGCTCAGTGGAGACACCTCGTGGCT
TGATAAAGGTTACCAGCTACGATGGCGAGGACAAGATCGGCTCTTACGCTGTGCTTTCTCCG
CAGGCTGTACTCAAGAGTGAAAAATTATCTTGCATCCACCCTCTCGCTGAACAAGTCATAGT
GATAACACACTCTGGCCGAAAAGGGCGTTATGCCGTGGAACCATACCATGGTAAAGTAGTGG
TGCCAGAGGGACATGCAATACCCGTCCAGGACTTTCAAGCTCTGAGTGAAAGTGCCACCATT
GTGTACAACGAACGTGAGTTCGTAAACAGGTACCTGCACCATATTGCCACACATGGAGGAGC
GCTGAACACTGATGAAGAATATTACAAAACTGTCAAGCCCAGCGAGCACGACGGCGAATACC
TGTACGACATCGACAGGAAACAGTGCGTCAAGAAAGAACTAGTCACTGGGCTAGGGCTCACA
GGCGAGCTGGTGGATCCTCCCTTCCATGAATTCGCCTACGAGAGTCTGAGAACACGACCAGC
CGCTCCTTACCAAGTACCAACCATAGGGGTGTATGGCGTGCCAGGATCAGGCAAGTCTGGCA
TCATTAAAAGCGCAGTCACCAAAAAAGATCTAGTGGTGAGCGCCAAGAAAGAAAACTGTGCA
GAAATTATAAGGGACGTCAAGAAAATGAAAGGGCTGGACGTCAATGCCAGAACTGTGGACTC
AGTGCTCTTGAATGGATGCAAACACCCCGTAGAGACCCTGTATATTGACGAAGCTTTTGCTT
GTCATGCAGGTACTCTCAGAGCGCTCATAGCCATTATAAGACCTAAAAAGGCAGTGCTCTGC
GGGGATCCCAAACAGTGCGGTTTTTTTAACATGATGTGCCTGAAAGTGCATTTTAACCACGA
GATTTGCACACAAGTCTTCCACAAAAGCATCTCTCGCCGTTGCACTAAATCTGTGACTTCGG
TCGTCTCAACCTTGTTTTACGACAAAAAAATGAGAACGACGAATCCGAAAGAGACTAAGATT
GTGATTGACACTACCGGCAGTACCAAACCTAAGCAGGACGATCTCATTCTCACTTGTTTCAG
AGGGTGGGTGAAGCAGTTGCAAATAGATTACAAAGGCAACGAAATAATGACGGCAGCTGCCT
CTCAAGGGCTGACCCGTAAAGGTGTGTATGCCGTTCGGTACAAGGTGAATGAAAATCCTCTG
TACGCACCCACCTCAGAACATGTGAACGTCCTACTGACCCGCACGGAGGACCGCATCGTGTG
GAAAACACTAGCCGGCGACCCATGGATAAAAACACTGACTGCCAAGTACCCTGGGAATTTCA
CTGCCACGATAGAGGAGTGGCAAGCAGAGCATGATGCCATCATGAGGCACATCTTGGAGAGA
CCGGACCCTACCGACGTCTTCCAGAATAAGGCAAACGTGTGTTGGGCCAAGGCTTTAGTGCC
GGTGCTGAAGACCGCTGGCATAGACATGACCACTGAACAATGGAACACTGTGGATTATTTTG
AAACGGACAAAGCTCACTCAGCAGAGATAGTATTGAACCAACTATGCGTGAGGTTCTTTGGA
CTCGATCTGGACTCCGGTCTATTTTCTGCACCCACTGTTCCGTTATCCATTAGGAATAATCA
CTGGGATAACTCCCCGTCGCCTAACATGTACGGGCTGAATAAAGAAGTGGTCCGTCAGCTCT
CTCGCAGGTACCCACAACTGCCTCGGGCAGTTGCCACTGGAAGAGTCTATGACATGAACACT
GGTACACTGCGCAATTATGATCCGCGCATAAACCTAGTACCTGTAAACAGAAGACTGCCTCA
TGCTTTAGTCCTCCACCATAATGAACACCCACAGAGTGACTTTTCTTCATTCGTCAGCAAAT
TGAAGGGCAGAACTGTCCTGGTGGTCGGGGAAAAGTTGTCCGTCCCAGGCAAAATGGTTGAC
TGGTTGTCAGACCGGCCTGAGGCTACCTTCAGAGCTCGGCTGGATTTAGGCATCCCAGGTGA
TGTGCCCAAATATGACATAATATTTGTTAATGTGAGGACCCCATATAAATACCATCACTATC
AGCAGTGTGAAGACCATGCCATTAAGCTTAGCATGTTGACCAAGAAAGCTTGTCTGCATCTG
AATCCCGGCGGAACCTGTGTCAGCATAGGTTATGGTTACGCTGACAGGGCCAGCGAAAGCAT
CATTGGTGCTATAGCGCGGCAGTTCAAGTTTTCCCGGGTATGCAAACCGAAATCCTCACTTG
AAGAGACGGAAGTTCTGTTTGTATTCATTCGGTACGATCGCAAGGCCCGTACGCACAATTCT
TACAAGCTTTCATCAACCTTGACCAACATTTATACAGGTTCCAGACTCCACGAAGCCGGATG
TGCACCCTCATATCATGTGGTGCGAGGGGATATTGCCACGGCCACCGAAGGAGTGATTATAA
ATGCTGCTAACAGCAAAGGACAACCTGGCGGAGGGGTGTGCGGAGCGCTGTATAAGAAATTC
```

-continued

```
CCGGAAAGCTTCGATTTACAGCCGATCGAAGTAGGAAAAGCGCGACTGGTCAAAGGTGCAGC

TAAACATATCATTCATGCCGTAGGACCAAACTTCAACAAAGTTTCGGAGGTTGAAGGTGACA

AACAGTTGGCAGAGGCTTATGAGTCCATCGCTAAGATTGTCAACGATAACAATTACAAGTCA

GTAGCGATTCCACTGTTGTCCACCGGCATCTTTTCCGGGAACAAAGATCGACTAACCCAATC

ATTGAACCATTTGCTGACAGCTTTAGACACCACTGATGCAGATGTAGCCATATACTGCAGGG

ACAAGAAATGGGAAATGACTCTCAAGGAAGCAGTGGCTAGGAGAGAAGCAGTGGAGGAGATA

TGCATATCCGACGACTCTTCAGTGACAGAACCTGATGCAGAGCTGGTGAGGGTGCATCCGAA

GAGTTCTTTGGCTGGAAGGAAGGGCTACAGCACAAGCGATGGCAAAACTTTCTCATATTTGG

AAGGGACCAAGTTTCACCAGGCGGCCAAGGATATAGCAGAAATTAATGCCATGTGGCCCGTT

GCAACGGAGGCCAATGAGCAGGTATGCATGTATATCCTCGGAGAAGGCATGAGCAGTATTAG

GTCGAAATGCCCCGTCGAAGAGTCGGAAGCCTCCACACCACCTAGCACGCTGCCTTGCTTGT

GCATCCATGCCATGACTCCAGAAAGAGTACAGCGCCTAAAAGCCTCACGTCCAGAACAAATT

ACTGTGTGCTCATCCTTTCCATTGCCGAAGTATAGAATCACTGGTGTGCAGAAGATCCAATG

CTCCCAGCCTATATTGTTCTCACCGAAAGTGCCTGCGTATATTCATCCAAGGAAGTATCTCG

TGGAAACACCACCGGTAGACGAGACTCCGGAGCCATCGGCAGAGAACCAATCCACAGAGGGG

ACACCTGAACAACCACCACTTATAACCGAGGATGAGACCAGGACTAGAACGCCTGAGCCGAT

CATCATCGAAGAGGAAGAAGAGGATAGCATAAGTTTGCTGTCAGATGGCCCGACCCACCAGG

TGCTGCAAGTCGAGGCAGACATTCACGGGCCGCCCTCTGTATCTAGCTCATCCTGGTCCATT

CCTCATGCATCCGACTTTGATGTGGACAGTTTATCCATACTTGACACCCTGGAGGGAGCTAG

CGTGACCAGCGGGGCAACGTCAGCCGAGACTAACTCTTACTTCGCAAAGAGTATGGAGTTTC

TGGCGCGACCGGTGCCTGCGCCTCGAACAGTATTCAGGAACCCTCCACATCCCGCTCCGCGC

ACAAGAACACCGTCACTTGCACCCAGCAGGGCCTGCTCGAGAACCAGCCTAGTTTCCACCCC

GCCAGGCGTGAATAGGGTGATCACTAGAGAGGAGCTCGAGGCGCTTACCCCGTCACGCACTC

CTAGCAGGTCGGTCTCGAGAACCAGCCTGGTCTCCAACCCGCCAGGCGTAAATAGGGTGATT

ACAAGAGAGGAGTTTGAGGCGTTCGTAGCACAACAACAATGACGGTTTGATGCGGGTGCATA

CATCTTTTCCTCCGACACCGGTCAAGGGCATTTACAACAAAAATCAGTAAGGCAAACGGTGC

TATCCGAAGTGGTGTTGGAGAGGACCGAATTGGAGATTTCGTATGCCCCGCGCCTCGACCAA

GAAAAGAAGAATTACTACGCAAGAAATTACAGTTAAATCCCACACCTGCTAACAGAAGCAG

ATACCAGTCCAGGAAGGTGGAGAACATGAAAGCCATAACAGCTAGACGTATTCTGCAAGGCC

TAGGGCATTATTTGAAGGCAGAAGGAAAAGTGGAGTGCTACCGAACCCTGCATCCTGTTCCT

TTGTATTCATCTAGTGTGAACCGTGCCTTTTCAAGCCCCAAGGTCGCAGTGGAAGCCTGTAA

CGCCATGTTGAAAGAGAACTTTCCGACTGTGGCTTCTTACTGTATTATTCCAGAGTACGATG

CCTATTTGGACATGGTTGACGGAGCTTCATGCTGCTTAGACACTGCCAGTTTTTGCCCTGCA

AAGCTGCGCAGCTTTCCAAAGAAACACTCCTATTTGGAACCCACAATACGATCGGCAGTGCC

TTCAGCGATCCAGAACACGCTCCAGAACGTCCTGGCAGCTGCCACAAAAAGAAATTGCAATG

TCACGCAAATGAGAGAATTGCCCGTATTGGATTCGGCGGCCTTTAATGTGGAATGCTTCAAG

AAATATGCGTGTAATAATGAATATTGGGAAACGTTTAAAGAAAACCCCATCAGGCTTACTGA

AGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAG

AGAGACGTGAAAGTGACTCCAGGAACAAAACATACTGAAGAACGGCCCAAGGTACAGGTGAT
```

```
-continued
CCAGGCTGCCGATCCGCTAGCAACAGCGTATCTGTGCGGAATCCACCGAGAGCTGGTTAGGA

GATTAAATGCGGTCCTGCTTCCGAACATTCATACACTGTTTGATATGTCGGCTGAAGACTTT

GACGCTATTATAGCCGAGCACTTCCAGCCTGGGGATTGTGTTCTGGAAACTGACATCGCGTC

GTTTGATAAAAGTGAGGACGACGCCATGGCTCTGACCGCGTTAATGATTCTGGAAGACTTAG

GTGTGGACGCAGAGCTGTTGACGCTGATTGAGGCGGCTTTCGGCGAAATTTCATCAATACAT

TTGCCCACTAAAACTAAATTTAAATTCGGAGCCATGATGAAATCTGGAATGTTCCTCACACT

GTTTGTGAACACAGTCATTAACATTGTAATCGCAAGCAGAGTGTTGAGAGAACGGCTAACCG

GATCACCATGTGCAGCATTCATTGGAGATGACAATATCGTGAAAGGAGTCAAATCGGACAAA

TTAATGGCAGACAGGTGCGCCACCTGGTTGAATATGGAAGTCAAGATTATAGATGCTGTGGT

GGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGAC

GATGAACATGATGATGACAGGAGAAGGGCATTGCATGAAGAGTCAACACGCTGGAACCGAGT

GGGTATTCTTTCAGAGCTGTGCAAGGCAGTAGAATCAAGGTATGAAACCGTAGGAACTTCCA

TCATAGTTATGGCCATGACTACTCTAGCTAGCAGTGTTAAATCATTCAGCTACCTGAGAGGG

GCCCCTATAACTCTCTACGGCTAACCTGAATGGACTACGACATAGTCTAGTCCGCCAAGTCT

AGCATATGGGCGCGCCCTCAGCATCGATTTGAATTGGCCACCATGAGGGTCCCCGCTCAGCT

CCTGGGGCTCCTGCTGCTCTGGCTCCCAGGTGCACGATGTGCCATGTGGGAGCTGGAGAAAG

ACGTTTATGTTGTAGAGGTGGACTGGACTCCCGATGCCCCTGGAGAAACAGTGAACCTCACC

TGTGACACGCCTGAAGAAGATGACATCACCTGGACCTCAGACCAGAGACATGGAGTCATAGG

CTCTGGAAAGACCCTGACCATCACTGTCAAAGAGTTTCTAGATGCTGGCCAGTACACCTGCC

ACAAAGGAGGCGAGACTCTGAGCCACTCACATCTGCTGCTCCACAAGAAGGAAAATGGAATT

TGGTCCACTGAAATTTTAAAAAATTTCAAAAACAAGACTTTCCTGAAGTGTGAAGCACCAAA

TTACTCCGGACGGTTCACGTGCTCATGGCTGGTGCAAAGAAACATGGACTTGAAGTTCAACA

TCAAGAGCAGTAGCAGTTCCCCTGACTCTCGGGCAGTGACATGTGGAATGGCGTCTCTGTCT

GCAGAGAAGGTCACACTGGACCAAAGGGACTATGAGAAGTATTCAGTGTCCTGCCAGGAGGA

TGTCACCTGCCCAACTGCCGAGGAGACCCTGCCCATTGAACTGGCGTTGGAAGCACGGCAGC

AGAATAAATATGAGAACTACAGCACCAGCTTCTTCATCAGGGACATCATCAAACCAGACCCG

CCCAAGAACTTGCAGATGAAGCCTTTGAAGAACTCACAGGTGGAGGTCAGCTGGGAGTACCC

TGACTCCTGGAGCACTCCCCATTCCTACTTCTCCCTCAAGTTCTTTGTTCGAATCCAGCGCA

AGAAAGAAAGATGAAGGAGACAGAGGAGGGGTGTAACCAGAAAGGTGCGTTCCTCGTAGAG

AAGACATCTACCGAAGTCCAATGCAAAGGCGGGAATGTCTGCGTGCAAGCTCAGGATCGCTA

TTACAATTCCTCATGCAGCAAGTGGGCATGTGTTCCCTGCAGGGTCCGATCCGGAGGTTCCG

GTGGTGGATCCGGAGGTGGCTCCGGCGGCGGATCCAGGGTCATTCCAGTCTCTGGACCTGCC

AGGTGTCTTAGCCAGTCCCGAAACCTGCTGAAGACCACAGATGACATGGTGAAGACGGCCAG

AGAAAAACTGAAACATTATTCCTGCACTGCTGAAGACATCGATCATGAAGACATCACACGGG

ACCAAACCAGCACATTGAAGACCTGTTTACCACTGGAACTACACAAGAACGAGAGTTGCCTG

GCTACTAGAGAGACTTCTTCCACAACAAGAGGGAGCTGCCTGCCCCCACAGAAGACGTCTTT

GATGATGACCCTGTGCCTTGGTAGCATCTATGAGGACTTGAAGATGTACCAGACAGAGTTCC

AGGCCATCAACGCAGCACTTCAGAATCACAACCATCAGCAGATCATTCTAGACAAGGGCATG

CTGGTGGCCATCGATGAGCTGATGCAGTCTCTGAATCATAATGGCGAGACTCTGCGCCAGAA

ACCTCCTGTGGGAGAAGCAGACCCTTACAGAGTGAAAATGAAGCTCTGCATCCTGCTTCACG
```

-continued

```
CCTTCAGCACCCGCGTCGTGACCATCAACAGGGTGATGGGCTATCTGAGCTCCGCCGGTTCC

GGTGGCGGATCCGAAGCACACAAGAGTGAGATCGCCCATCGGTATAATGATTTGGGAGAACA

ACATTTCAAAGGCCTAGTCCTGATTGCCTTTTCCCAGTATCTCCAGAAATGCTCATACGATG

AGCATGCCAAATTAGTGCAGGAAGTAACAGACTTTGCAAAGACGTGTGTTGCCGATGAGTCT

GCCGCCAACTGTGACAAATCCCTTCACACTCTTTTTGGAGATAAGTTGTGTGCCATTCCAAA

CCTCCGTGAAAACTATGGTGAACTGGCTGACTGCTGTACAAAACAAGAGCCCGAAAGAAACG

AATGTTTCCTGCAACACAAAGATGACAACCCCAGCCTGCCACCATTTGAAAGGCCAGAGGCT

GAGGCCATGTGCACCTCCTTTAAGGAAAACCCAACCACCTTTATGGGACACTATTTGCATGA

AGTTGCCAGAAGACATCCTTATTTCTATGCCCCAGAACTTCTTTACTATGCTGAGCAGTACA

ATGAGATTCTGACCCAGTGTTGTGCAGAGGCTGACAAGGAAAGCTGCCTGACCCCGAAGCTT

GATGGTGTGAAGGAGAAAGCATTGGTCTCATCTGTCCGTCAGAGAATGAAGTGCTCCAGTAT

GCAGAAGTTTGGAGAGAGCTTTTAAAGCATGGGCAGTAGCTCGTCTGAGCCAGACATTCC

CCAATGCTGACTTTGCAGAAATCACCAAATTGGCAACAGACCTGACCAAAGTCAACAAGGAG

TGCTGCCATGGTGACCTGCTGGAATGCGCAGATGACAGGGCGGAACTTGCCAAGTACATGTG

TGAAAACCAGGCGACTATCTCCAGCAAACTGCAGACTTGCTGCGATAAACCACTGTTGAAGA

AAGCCCACTGTCTTAGTGAGGTGGAGCATGACACCATGCCTGCTGATCTGCCTGCCATTGCT

GCTGATTTTGTTGAGGACCAGGAAGTGTGCAAGAACTATGCTGAGGCCAAGGATGTCTTCCT

GGGCACGTTCTTGTATGAATATTCAAGAAGACACCCTGATTACTCTGTATCCCTGTTGCTGA

GACTTGCTAAGAAATATGAAGCCACTCTGGAAAAGTGCTGCGCTGAAGCCAATCCTCCCGCA

TGCTACGGCACAGTGCTTGCTGAATTTCAGCCTCTTGTAGAAGAGCCTAAGAACTTGGTCAA

AACCAACTGTGATCTTTACGAGAAGCTTGGAGAATATGGATTCCAAAATGCCATTCTAGTTC

GCTACACCCAGAAAGCACCTCAGGTGTCAACCCCAACTCTCGTGGAGGCTGCAAGAAACCTA

GGAAGAGTGGGCACCAAGTGTTGTACACTTCCTGAAGATCAGAGACTGCCTTGTGTGGAAGA

CTATCTGTCTGCAATCCTGAACCGTGTGTGTCTGCTGCATGAGAAGACCCCAGTGAGTGAGC

ATGTTACCAAGTGCTGTAGTGGATCCCTGGTGGAAAGGCGGCCATGCTTCTCTGCTCTGACA

GTTGATGAAACATATGTCCCCAAAGAGTTTAAAGCTGAGACCTTCACCTTCCACTCTGATAT

CTGCACACTTCCAGAGAAGGAGAAGCAGATTAAGAAACAAACGGCTCTTGCTGAGCTGGTGA

AGCACAAGCCCAAGGCTACAGCGGAGCAACTGAAGACTGTCATGGATGACTTTGCACAGTTC

CTGGATACATGTTGCAAGGCTGCTGACAAGGACACCTGCTTCTCGACTGAGGGTCCAAACCT

TGTCACTAGATGCAAAGACGCCTTAGCCTGAGCGATCGCTAAATACAGCAGCAATTGGCAAG

CTGCTTACATAGAACTCGCGGCGATTGGCATGCCGCCTTAAAATTTTTATTTTATTTTTCTT

TTCTTTTCCGAATCGGATTTTGTTTTTAATATTTCAAAAAAAAAAAAAAAAAAAAAAAAAAC

GCGTCGAGGGGAATTAATTCTTGAAGACGAAAGGGCCAGGTGGCACTTTTCGGGGAAATGTG

CGCGGAACCCCTATTTGTTTATTTTTCTAAATACATTCAAATATGTATCCGCTCATGAGACA

ATAACCCTGATAAATGCTTCAATAATATTGAAAAAGGAAGAGTATGAGTATTCAACATTTCC

GTGTCGCCCTTATTCCCTTTTTGCGGCATTTTGCCTTCCTGTTTTTGCTCACCCAGAAACG

CTGGTGAAAGTAAAAGATGCTGAAGATCAGTTGGGTGCACGAGTGGGTTACATCGAACTGGA

TCTCAACAGCGGTAAGATCCTTGAGAGTTTTCGCCCCGAAGAACGTTTTCCAATGATGAGCA

CTTTTAAAGTTCTGCTATGTGGCGCGGTATTATCCCGTGTTGACGCCGGGCAAGAGCAACTC

GGTCGCCGCATACACTATTCTCAGAATGACTTGGTTGAGTACTCACCAGTCACAGAAAAGCA
```

```
-continued
TCTTACGGATGGCATGACAGTAAGAGAATTATGCAGTGCTGCCATAACCATGAGTGATAACA

CTGCGGCCAACTTACTTCTGACAACGATCGGAGGACCGAAGGAGCTAACCGCTTTTTTGCAC

AACATGGGGATCATGTAACTCGCCTTGATCGTTGGGAACCGGAGCTGAATGAAGCCATACC

AAACGACGAGCGTGACACCACGATGCCTGTAGCAATGGCAACAACGTTGCGCAAACTATTAA

CTGGCGAACTACTTACTCTAGCTTCCCGGCAACAATTAATAGACTGGATGGAGGCGGATAAA

GTTGCAGGACCACTTCTGCGCTCGGCCCTTCCGGCTGGCTGGTTTATTGCTGATAAATCTGG

AGCCGGTGAGCGTGGGTCTCGCGGTATCATTGCAGCACTGGGGCCAGATGGTAAGCCCTCCC

GTATCGTAGTTATCTACACGACGGGGAGTCAGGCAACTATGGATGAACGAAATAGACAGATC

GCTGAGATAGGTGCCTCACTGATTAAGCATTGGTAACTGTCAGACCAAGTTTACTCATATAT

ACTTTAGATTGATTTAAAACTTCATTTTTAATTTAAAAGGATCTAGGTGAAGATCCTTTTTG

ATAATCTCATGACCAAAATCCCTTAACGTGAGTTTTCGTTCCACTGAGCGTCAGACCCCGTA

GAAAAGATCAAAGGATCTTCTTGAGATCCTTTTTTTCTGCGCGTAATCTGCTGCTTGCAAAC

AAAAAAACCACCGCTACCAGCGGTGGTTTGTTTGCCGGATCAAGAGCTACCAACTCTTTTTC

CGAAGGTAACTGGCTTCAGCAGAGCGCAGATACCAAATACTGTCCTTCTAGTGTAGCCGTAG

TTAGGCCACCACTTCAAGAACTCTGTAGCACCGCCTACATACCTCGCTCTGCTAATCCTGTT

ACCAGTGGCTGCTGCCAGTGGCGATAAGTCGTGTCTTACCGGGTTGGACTCAAGACGATAGT

TACCGGATAAGGCGCAGCGGTCGGGCTGAACGGGGGGTTCGTGCACACAGCCCAGCTTGGAG

CGAACGACCTACACCGAACTGAGATACCTACAGCGTGAGCATTGAGAAAGCGCCACGCTTCC

CGAAGGGAGAAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCACCTCTGA

CTTGAGCGTCGATTTTTGTGATGCTCGTCAGGGGGGCGGAGCCTATGGAAAAACGCCAGCAA

CGCGAGCTCTAATACGACTCACTATAG
```

In some embodiments, the replicon RNA-IL-12 is fused with a serum albumin coding sequence. In some embodiments, the IL-12-albumin fusion molecule has a longer half live in tumor microenvironment. In some embodiments, the IL-12-albumin fusion protein can persist in tumor microenvironment for at least 1 day, 2 days, 3 days, 4 days, 5 days, 6 days, 7 days, 8 days, or longer.

In some embodiments, the synthetic oncolytic virus comprises LNP-replicon RNA-IL-12-serum albumin. In other embodiments, the synthetic oncolytic virus comprises TT3-LNP-repliconRNA-IL-12-serum albumin. In other embodiments, the synthetic oncolytic virus comprises TT3-LNP-mtReplicon RNA-IL-12-serum albumin. The persist presence of IL-12 in the tumor microenvironment may prolong the anti-tumor immune response exerted by the synthetic oncolytic virus.

In some embodiments, the replicon RNA-IL12-serum albumin further comprises a coding sequence for lumican. Lumican is one of the major extracellular proteins in the interstitial extracellular matrix (ECM) of the skin, corneal stroma, sclera, aorta, muscle, lung, kidney, bone, cartilage and intervertebral discs. It is a member of the family of small, leucine-rich proteoglycans (SLRP), with a core protein of 30-50 kDa comprising a signal peptide, a negatively charged N-terminal domain, a highly conserved leucine-rich internal domain and a carboxyl-terminal domain. The protein core and the glycan chains of lumican can interact with various cellular effectors, including cytokines, growth factors and cell surface receptors, to modulate cell adhesion, proliferation and migration. As an endogenous collagen-binding protein, the presence of lumican in tumor microenvironment would promote local retention of IL-12 to enhance efficacy and safety of the tumor immunotherapy, as described herein. In some embodiments, the replicon RNA-IL-12-MSA comprises a coding sequence for lumican. In other embodiments, the mtReplicon RNA-IL-12-MSA (mtRep-IL12-MSA) comprises a coding sequence for lumican. An exemplary coding sequence for mtReplicon RNA-IL-12-MSA-lumican (mtRep-IL12-MSA-Lumican) is set forth in SEQ ID NO: 5:

(SEQ ID NO: 5)
```
ATGGGCGGCGCATGAGAGAAGCCCAGACCAATTACCTACCCAAAATGGAGAAAGTTCACGTT

GACATCGAGGAAGACAGCCCATTCCTCAGAGCTTTGCAGCGGAGCTTCCCGCAGTTTGAGGT

AGAAGCCAAGCAGGTCACTGATAATGACCATGCTAATGCCAGAGCGTTTTCGCATCTGGCTT

CAAAACTGATCGAAACGGAGGTGGACCCATCCGACACGATCCTTGACATTGGAAGTGCGCCC
```

-continued
```
GCCCGCAGAATGTATTCTAAGCACAAGTATCATTGTATCTGTCCGATGAGATGTGCGGAAGA

TCCGGACAGATTGTATAAGTATGCAACTAAGCTGAAGAAAAACTGTAAGGAAATAACTGATA

AGGAATTGGACAAGAAAATGAAGGAGCTGGCCGCCGTCATGAGCGACCCTGACCTGGAAACT

GAGACTATGTGCCTCCACGACGACGAGTCGTGTCGCTACGAAGGGCAAGTCGCTGTTTACCA

GGATGTATACGCGGTTGACGGACCGACAAGTCTCTATCACCAAGCCAATAAGGGAGTTAGAG

TCGCCTACTGGATAGGCTTTGACACCACCCCTTTTATGTTTAAGAACTTGGCTGGAGCATAT

CCATCATACTCTACCAACTGGGCCGACGAAACCGTGTTAACGGCTCGTAACATAGGCCTATG

CAGCTCTGACGTTATGGAGCGGTCACGTAGAGGGATGTCCATTCTTAGAAAGAAGTATTTGA

AACCATCCAACAATGTTCTATTCTCTGTTGGCTCGACCATCTACCACGAGAAGAGGGACTTA

CTGAGGAGCTGGCACCTGCCGTCTGTATTTCACTTACGTGGCAAGCAAAATTACACATGTCG

GTGTGAGACTATAGTTAGTTGCGACGGGTACGTCGTTAAAAGAATAGCTATCAGTCCAGGCC

TGTATGGGAAGCCTTCAGGCTATGCTGCTACGATGCACCGCGAGGGATTCTTGTGCTGCAAA

GTGACAGACACATTGAACGGGGAGAGGGTCTCTTTTCCCGTGTGCACGTATGTGCCAGCTAC

ATTGTGTGACCAAATGACTGGCATACTGGCAACAGATGTCAGTGCGGACGACGCGCAAAAC

TGCTGGTTGGGCTCAACCAGCGTATAGTCGTCAACGGTCGCACCCAGAGAAACACCAATACC

ATGAAAAATTACCTTTTGCCCGTAGTGGCCCAGGCATTTGCTAGGTGGGCAAAGGAATATAA

GGAAGATCAAGAAGATGAAAGGCCACTAGGACTACGAGATAGACAGTTAGTCATGGGGTGTT

GTTGGGCTTTTAGAAGGCACAAGATAACATCTATTTATAAGCGCCCGGATACCCAAACCATC

ATCAAAGTGAACAGCGATTTCCACTCATTCGTGCTGCCCAGGATAGGCAGTAACACATTGGA

GATCGGGCTGAGAACAAGAATCAGGAAAATGTTAGAGGAGCACAAGGAGCCGTCACCTCTCA

TTACCGCCGAGGACGTACAAGAAGCTAAGTGCGCAGCCGATGAGGCTAAGGAGGTGCGTGAA

GCCGAGGAGTTGCGCGCAGCTCTACCACCTTTGGCAGCTGATGTTGAGGAGCCCACTCTGGA

AGCCGATGTCGACTTGATGTTACAAGAGGCTGGGGCCGGCTCAGTGGAGACACCTCGTGGCT

TGATAAAGGTTACCAGCTACGATGGCGAGGACAAGATCGGCTCTTACGCTGTGCTTTCTCCG

CAGGCTGTACTCAAGAGTGAAAAATTATCTTGCATCCACCCTCTCGCTGAACAAGTCATAGT

GATAACACACTCTGGCCGAAAAGGGCGTTATGCCGTGGAACCATACCATGGTAAAGTAGTGG

TGCCAGAGGGACATGCAATACCCGTCCAGGACTTTCAAGCTCTGAGTGAAAGTGCCACCATT

GTGTACAACGAACGTGAGTTCGTAAACAGGTACCTGCACCATATTGCCACACATGGAGGAGC

GCTGAACACTGATGAAGAATATTACAAAACTGTCAAGCCCAGCGAGCACGACGGCGAATACC

TGTACGACATCGACAGGAAACAGTGCGTCAAGAAAGAACTAGTCACTGGGCTAGGGCTCACA

GGCGAGCTGGTGGATCCTCCCTTCCATGAATTCGCCTACGAGAGTCTGAGAACACGACCAGC

CGCTCCTTACCAAGTACCAACCATAGGGGTGTATGGCGTGCCAGGATCAGGCAAGTCTGGCA

TCATTAAAAGCGCAGTCACCAAAAAAGATCTAGTGGTGAGCGCCAAGAAAGAAAACTGTGCA

GAAATTATAAGGGACGTCAAGAAAATGAAAGGGCTGGACGTCAATGCCAGAACTGTGGACTC

AGTGCTCTTGAATGGATGCAAACACCCCGTAGAGACCCTGTATATTGACGAAGCTTTTGCTT

GTCATGCAGGTACTCTCAGAGCGCTCATAGCCATTATAAGACCTAAAAAGGCAGTGCTCTGC

GGGGATCCCAAACAGTGCGGTTTTTTTAACATGATGTGCCTGAAAGTGCATTTTAACCACGA

GATTTGCACACAAGTCTTCCACAAAAGCATCTCTCGCCGTTGCACTAAATCTGTGACTTCGG

TCGTCTCAACCTTGTTTTACGACAAAAAAATGAGAACGACGAATCCGAAAGAGACTAAGATT

GTGATTGACACTACCGGCAGTACCAAACCTAAGCAGGACGATCTCATTCTCACTTGTTTCAG

AGGGTGGGTGAAGCAGTTGCAAATAGATTACAAAGGCAACGAAATAATGACGGCAGCTGCCT
```

-continued

```
CTCAAGGGCTGACCCGTAAAGGTGTGTATGCCGTTCGGTACAAGGTGAATGAAAATCCTCTG

TACGCACCCACCTCAGAACATGTGAACGTCCTACTGACCCGCACGGAGGACCGCATCGTGTG

GAAAACACTAGCCGGCGACCCATGGATAAAAACACTGACTGCCAAGTACCCTGGGAATTTCA

CTGCCACGATAGAGGAGTGGCAAGCAGAGCATGATGCCATCATGAGGCACATCTTGGAGAGA

CCGGACCCTACCGACGTCTTCCAGAATAAGGCAAACGTGTGTTGGGCCAAGGCTTTAGTGCC

GGTGCTGAAGACCGCTGGCATAGACATGACCACTGAACAATGGAACACTGTGGATTATTTTG

AAACGGACAAAGCTCACTCAGCAGAGATAGTATTGAACCAACTATGCGTGAGGTTCTTTGGA

CTCGATCTGGACTCCGGTCTATTTTCTGCACCCACTGTTCCGTTATCCATTAGGAATAATCA

CTGGGATAACTCCCCGTCGCCTAACATGTACGGGCTGAATAAAGAAGTGGTCCGTCAGCTCT

CTCGCAGGTACCCACAACTGCCTCGGGCAGTTGCCACTGGAAGAGTCTATGACATGAACACT

GGTACACTGCGCAATTATGATCCGCGCATAAACCTAGTACCTGTAAACAGAAGACTGCCTCA

TGCTTTAGTCCTCCACCATAATGAACACCCACAGAGTGACTTTTCTTCATTCGTCAGCAAAT

TGAAGGGCAGAACTGTCCTGGTGGTCGGGGAAAAGTTGTCCGTCCCAGGCAAAATGGTTGAC

TGGTTGTCAGACCGGCCTGAGGCTACCTTCAGAGCTCGGCTGGATTTAGGCATCCCAGGTGA

TGTGCCCAAATATGACATAATATTTGTTAATGTGAGGACCCCATATAAATACCATCACTATC

AGCAGTGTGAAGACCATGCCATTAAGCTTAGCATGTTGACCAAGAAAGCTTGTCTGCATCTG

AATCCCGGCGGAACCTGTGTCAGCATAGGTTATGGTTACGCTGACAGGGCCAGCGAAAGCAT

CATTGGTGCTATAGCGCGGCAGTTCAAGTTTTCCCGGGTATGCAAACCGAAATCCTCACTTG

AAGAGACGGAAGTTCTGTTTGTATTCATTCGGTACGATCGCAAGGCCCGTACGCACAATTCT

TACAAGCTTTCATCAACCTTGACCAACATTTATACAGGTTCCAGACTCCACGAAGCCGGATG

TGCACCCTCATATCATGTGGTGCGAGGGGATATTGCCACGGCCACCGAAGGAGTGATTATAA

ATGCTGCTAACAGCAAAGGACAACCTGGCGGAGGGGTGTGCGGAGCGCTGTATAAGAAATTC

CCGGAAAGCTTCGATTTACAGCCGATCGAAGTAGGAAAAGCGCGACTGGTCAAAGGTGCAGC

TAAACATATCATTCATGCCGTAGGACCAAACTTCAACAAAGTTTCGGAGGTTGAAGGTGACA

AACAGTTGGCAGAGGCTTATGAGTCCATCGCTAAGATTGTCAACGATAACAATTACAAGTCA

GTAGCGATTCCACTGTTGTCCACCGGCATCTTTTCCGGGAACAAAGATCGACTAACCCAATC

ATTGAACCATTTGCTGACAGCTTTAGACACCACTGATGCAGATGTAGCCATATACTGCAGGG

ACAAGAAATGGGAAATGACTCTCAAGGAAGCAGTGGCTAGGAGAGAAGCAGTGGAGGAGATA

TGCATATCCGACGACTCTTCAGTGACAGAACCTGATGCAGAGCTGGTGAGGGTGCATCCGAA

GAGTTCTTTGGCTGGAAGGAAGGGCTACAGCACAAGCGATGGCAAAACTTTCTCATATTTGG

AAGGGACCAAGTTTCACCAGGCGGCCAAGGATATAGCAGAAATTAATGCCATGTGGCCCGTT

GCAACGGAGGCCAATGAGCAGGTATGCATGTATATCCTCGGAGAAGGCATGAGCAGTATTAG

GTCGAAATGCCCCGTCGAAGAGTCGGAAGCCTCCACACCACCTAGCACGCTGCCTTGCTTGT

GCATCCATGCCATGACTCCAGAAAGAGTACAGCGCCTAAAAGCCTCACGTCCAGAACAAATT

ACTGTGTGCTCATCCTTTCCATTGCCGAAGTATAGAATCACTGGTGTGCAGAAGATCCAATG

CTCCCAGCCTATATTGTTCTCACCGAAAGTGCCTGCGTATATTCATCCAAGGAAGTATCTCG

TGGAAACACCACCGGTAGACGAGACTCCGGAGCCATCGGCAGAGAACCAATCCACAGAGGGG

ACACCTGAACAACCACCACTTATAACCGAGGATGAGACCAGGACTAGAACGCCTGAGCCGAT

CATCATCGAAGAGGAAGAAGAGGATAGCATAAGTTTGCTGTCAGATGGCCCGACCCACCAGG

TGCTGCAAGTCGAGGCAGACATTCACGGGCCGCCCTCTGTATCTAGCTCATCCTGGTCCATT
```

-continued

```
CCTCATGCATCCGACTTTGATGTGGACAGTTTATCCATACTTGACACCCTGGAGGGAGCTAG

CGTGACCAGCGGGGCAACGTCAGCCGAGACTAACTCTTACTTCGCAAAGAGTATGGAGTTTC

TGGCGCGACCGGTGCCTGCGCCTCGAACAGTATTCAGGAACCCTCCACATCCCGCTCCGCGC

ACAAGAACACCGTCACTTGCACCCAGCAGGGCCTGCTCGAGAACCAGCCTAGTTTCCACCCC

GCCAGGCGTGAATAGGGTGATCACTAGAGAGGAGCTCGAGGCGCTTACCCCGTCACGCACTC

CTAGCAGGTCGGTCTCGAGAACCAGCCTGGTCTCCAACCCGCCAGGCGTAAATAGGGTGATT

ACAAGAGAGGAGTTTGAGGCGTTCGTAGCACAACAACAATGACGGTTTGATGCGGGTGCATA

CATCTTTTCCTCCGACACCGGTCAAGGGCATTTACAACAAAAATCAGTAAGGCAAACGGTGC

TATCCGAAGTGGTGTTGGAGAGGACCGAATTGGAGATTTCGTATGCCCCGCGCCTCGACCAA

GAAAAGAAGAATTACTACGCAAGAAATTACAGTTAAATCCCACACCTGCTAACAGAAGCAG

ATACCAGTCCAGGAAGGTGGAGAACATGAAAGCCATAACAGCTAGACGTATTCTGCAAGGCC

TAGGGCATTATTTGAAGGCAGAAGGAAAAGTGGAGTGCTACCGAACCCTGCATCCTGTTCCT

TTGTATTCATCTAGTGTGAACCGTGCCTTTTCAAGCCCCAAGGTCGCAGTGGAAGCCTGTAA

CGCCATGTTGAAAGAGAACTTTCCGACTGTGGCTTCTTACTGTATTATTCCAGAGTACGATG

CCTATTTGGACATGGTTGACGGAGCTTCATGCTGCTTAGACACTGCCAGTTTTTGCCCTGCA

AAGCTGCGCAGCTTTCCAAAGAAACACTCCTATTTGGAACCCACAATACGATCGGCAGTGCC

TTCAGCGATCCAGAACACGCTCCAGAACGTCCTGGCAGCTGCCACAAAAAGAAATTGCAATG

TCACGCAAATGAGAGAATTGCCCGTATTGGATTCGGCGGCCTTTAATGTGGAATGCTTCAAG

AAATATGCGTGTAATAATGAATATTGGGAAACGTTTAAAGAAAACCCCATCAGGCTTACTGA

AGAAAACGTGGTAAATTACATTACCAAATTAAAAGGACCAAAAGCTGCTGCTCTTTTTGCGA

AGACACATAATTTGAATATGTTGCAGGACATACCAATGGACAGGTTTGTAATGGACTTAAAG

AGAGACGTGAAAGTGACTCCAGGAACAAAACATACTGAAGAACGGCCCAAGGTACAGGTGAT

CCAGGCTGCCGATCCGCTAGCAACAGCGTATCTGTGCGGAATCCACCGAGAGCTGGTTAGGA

GATTAAATGCGGTCCTGCTTCCGAACATTCATACACTGTTTGATATGTCGGCTGAAGACTTT

GACGCTATTATAGCCGAGCACTTCCAGCCTGGGGATTGTGTTCTGGAAACTGACATCGCGTC

GTTTGATAAAAGTGAGGACGACGCCATGGCTCTGACCGCGTTAATGATTCTGGAAGACTTAG

GTGTGGACGCAGAGCTGTTGACGCTGATTGAGGCGGCTTTCGGCGAAATTTCATCAATACAT

TTGCCCACTAAAACTAAATTTAAATTCGGAGCCATGATGAAATCTGGAATGTTCCTCACACT

GTTTGTGAACACAGTCATTAACATTGTAATCGCAAGCAGAGTGTTGAGAGAACGGCTAACCG

GATCACCATGTGCAGCATTCATTGGAGATGACAATATCGTGAAAGGAGTCAAATCGGACAAA

TTAATGGCAGACAGGTGCGCCACCTGGTTGAATATGGAAGTCAAGATTATAGATGCTGTGGT

GGGCGAGAAAGCGCCTTATTTCTGTGGAGGGTTTATTTTGTGTGACTCCGTGACCGGCACAG

CGTGCCGTGTGGCAGACCCCCTAAAAAGGCTGTTTAAGCTTGGCAAACCTCTGGCAGCAGAC

GATGAACATGATGATGACAGGAGAAGGGCATTGCATGAAGAGTCAACACGCTGGAACCGAGT

GGGTATTCTTTCAGAGCTGTGCAAGGCAGTAGAATCAAGGTATGAAACCGTAGGAACTTCCA

TCATAGTTATGGCCATGACTACTCTAGCTAGCAGTGTTAAATCATTCAGCTACCTGAGAGGG

GCCCCTATAACTCTCTACGGCTAACCTGAATGGACTACGACATAGTCTAGTCCGCCAAGTCT

AGCATATGGGCGCGCCCTCAGCATCGATTTGAATTGGCCACCATGAGGGTCCCCGCTCAGCT

CCTGGGGCTCCTGCTGCTCTGGCTCCCAGGTGCACGATGTGCCATGTGGGAGCTGGAGAAAG

ACGTTTATGTTGTAGAGGTGGACTGGACTCCCGATGCCCCTGGAGAAACAGTGAACCTCACC

TGTGACACGCCTGAAGAAGATGACATCACCTGGACCTCAGACCAGAGACATGGAGTCATAGG
```

-continued

```
CTCTGGAAAGACCCTGACCATCACTGTCAAAGAGTTTCTAGATGCTGGCCAGTACACCTGCC
ACAAAGGAGGCGAGACTCTGAGCCACTCACATCTGCTGCTCCACAAGAAGGAAAATGGAATT
TGGTCCACTGAAATTTTAAAAAATTTCAAAAACAAGACTTTCCTGAAGTGTGAAGCACCAAA
TTACTCCGGACGGTTCACGTGCTCATGGCTGGTGCAAAGAAACATGGACTTGAAGTTCAACA
TCAAGAGCAGTAGCAGTTCCCCTGACTCTCGGGCAGTGACATGTGGAATGGCGTCTCTGTCT
GCAGAGAAGGTCACACTGGACCAAAGGGACTATGAGAAGTATTCAGTGTCCTGCCAGGAGGA
TGTCACCTGCCCAACTGCCGAGGAGACCCTGCCCATTGAACTGGCGTTGGAAGCACGGCAGC
AGAATAAATATGAGAACTACAGCACCAGCTTCTTCATCAGGGACATCATCAAACCAGACCCG
CCCAAGAACTTGCAGATGAAGCCTTTGAAGAACTCACAGGTGGAGGTCAGCTGGGAGTACCC
TGACTCCTGGAGCACTCCCCATTCCTACTTCTCCCTCAAGTTCTTTGTTCGAATCCAGCGCA
AGAAAGAAAGATGAAGGAGACAGAGGAGGGGTGTAACCAGAAAGGTGCGTTCCTCGTAGAG
AAGACATCTACCGAAGTCCAATGCAAAGGCGGGAATGTCTGCGTGCAAGCTCAGGATCGCTA
TTACAATTCCTCATGCAGCAAGTGGGCATGTGTTCCCTGCAGGGTCCGATCCGGAGGTTCCG
GTGGTGGATCCGGAGGTGGCTCCGGCGGCGGATCCAGGGTCATTCCAGTCTCTGGACCTGCC
AGGTGTCTTAGCCAGTCCCGAAACCTGCTGAAGACCACAGATGACATGGTGAAGACGGCCAG
AGAAAAACTGAAACATTATTCCTGCACTGCTGAAGACATCGATCATGAAGACATCACACGGG
ACCAAACCAGCACATTGAAGACCTGTTTACCACTGGAACTACACAAGAACGAGAGTTGCCTG
GCTACTAGAGAGACTTCTTCCACAACAAGAGGGAGCTGCCTGCCCCCACAGAAGACGTCTTT
GATGATGACCCTGTGCCTTGGTAGCATCTATGAGGACTTGAAGATGTACCAGACAGAGTTCC
AGGCCATCAACGCAGCACTTCAGAATCACAACCATCAGCAGATCATTCTAGACAAGGGCATG
CTGGTGGCCATCGATGAGCTGATGCAGTCTCTGAATCATAATGGCGAGACTCTGCGCCAGAA
ACCTCCTGTGGGAGAAGCAGACCCTTACAGAGTGAAAATGAAGCTCTGCATCCTGCTTCACG
CCTTCAGCACCCGCGTCGTGACCATCAACAGGGTGATGGGCTATCTGAGCTCCGCCGGTTCC
GGTGGCGGATCCGAAGCACACAAGAGTGAGATCGCCCATCGGTATAATGATTTGGGAGAACA
ACATTTCAAAGGCCTAGTCCTGATTGCCTTTTCCCAGTATCTCCAGAAATGCTCATACGATG
AGCATGCCAAATTAGTGCAGGAAGTAACAGACTTTGCAAAGACGTGTGTTGCCGATGAGTCT
GCCGCCAACTGTGACAAATCCCTTCACACTCTTTTTGGAGATAAGTTGTGTGCCATTCCAAA
CCTCCGTGAAAACTATGGTGAACTGGCTGACTGCTGTACAAAACAAGAGCCCGAAAGAAACG
AATGTTTCCTGCAACACAAAGATGACAACCCCAGCCTGCCACCATTTGAAAGGCCAGAGGCT
GAGGCCATGTGCACCTCCTTTAAGGAAAACCCAACCACCTTTATGGGACACTATTTGCATGA
AGTTGCCAGAAGACATCCTTATTTCTATGCCCCAGAACTTCTTTACTATGCTGAGCAGTACA
ATGAGATTCTGACCCAGTGTTGTGCAGAGGCTGACAAGGAAAGCTGCCTGACCCCGAAGCTT
GATGGTGTGAAGGAGAAAGCATTGGTCTCATCTGTCCGTCAGAGAATGAAGTGCTCCAGTAT
GCAGAAGTTTGGAGAGAGCTTTTAAAGCATGGGCAGTAGCTCGTCTGAGCCAGACATTCC
CCAATGCTGACTTTGCAGAAATCACCAAATTGGCAACAGACCTGACCAAAGTCAACAAGGAG
TGCTGCCATGGTGACCTGCTGGAATGCGCAGATGACAGGGCGGAACTTGCCAAGTACATGTG
TGAAAACCAGGCGACTATCTCCAGCAAACTGCAGACTTGCTGCGATAAACCACTGTTGAAGA
AAGCCCACTGTCTTAGTGAGGTGGAGCATGACACCATGCCTGCTGATCTGCCTGCCATTGCT
GCTGATTTTGTTGAGGACCAGGAAGTGTGCAAGAACTATGCTGAGGCCAAGGATGTCTTCCT
GGGCACGTTCTTGTATGAATATTCAAGAAGACACCCTGATTACTCTGTATCCCTGTTGCTGA
```

```
-continued
GACTTGCTAAGAAATATGAAGCCACTCTGGAAAAGTGCTGCGCTGAAGCCAATCCTCCCGCA

TGCTACGGCACAGTGCTTGCTGAATTTCAGCCTCTTGTAGAAGAGCCTAAGAACTTGGTCAA

AACCAACTGTGATCTTTACGAGAAGCTTGGAGAATATGGATTCCAAAATGCCATTCTAGTTC

GCTACACCCAGAAAGCACCTCAGGTGTCAACCCCAACTCTCGTGGAGGCTGCAAGAAACCTA

GGAAGAGTGGGCACCAAGTGTTGTACACTTCCTGAAGATCAGAGACTGCCTTGTGTGGAAGA

CTATCTGTCTGCAATCCTGAACCGTGTGTGTCTGCTGCATGAGAAGACCCCAGTGAGTGAGC

ATGTTACCAAGTGCTGTAGTGGATCCCTGGTGGAAAGGCGGCCATGCTTCTCTGCTCTGACA

GTTGATGAAACATATGTCCCCAAAGAGTTTAAAGCTGAGACCTTCACCTTCCACTCTGATAT

CTGCACACTTCCAGAGAAGGAGAAGCAGATTAAGAAACAAACGGCTCTTGCTGAGCTGGTGA

AGCACAAGCCCAAGGCTACAGCGGAGCAACTGAAGACTGTCATGGATGACTTTGCACAGTTC

CTGGATACATGTTGCAAGGCTGCTGACAAGGACACCTGCTTCTCGACTGAGGGTCCAAACCT

TGTCACTAGATGCAAAGACGCCTTAGCCGGCGGAGGTTCCGGTGGCGGATCCCAATACTATG

ACTACGATATACCCCTGTTCATGTACGGGCAAATATCTCCAAACTGTGCACCAGAATGTAAC

TGCCCTCACTCATACCCCACTGCAATGTACTGTGACGACCTGAAGTTGAAATCCGTGCCAAT

GGTGCCTCCTGGGATTAAGTACCTGTACCTCCGCAACAATCAGATCGACCATATTGACGAGA

AGGCTTTTGAAAACGTCACAGACCTCCAGTGGCTTATCCTGGACCATAACCTGCTTGAAAAT

AGTAAGATAAAGGGCAAAGTATTTTCCAAACTTAAACAGCTTAAAAAACTCCACATCAACTA

CAATAACCTTACTGAATCCGTGGGACCATTGCCAAAATCTCTCCAAGATTTGCAGTTGACTA

ACAACAAGATATCCAAACTCGGCTCCTTCGATGGGCTGGTTAATCTGACTTTCATCTACTTG

CAACACAACCAATTGAAGGAGGATGCAGTTTCAGCTAGTCTTAAAGGTCTGAAAAGCCTTGA

GTATCTTGATCTGTCATTTAATCAAATGTCCAAGCTCCCTGCTGGGCTCCCAACAAGTCTGC

TGACACTCTATCTCGACAATAACAAGATAAGTAACATTCCCGATGAGTACTTTAAAAGATTT

ACCGGCCTCCAATACTTGCGGCTTTCTCACAACGAGTTGGCAGACTCTGGTGTACCCGGCAA

CTCCTTTAATATAAGTTCTCTTCTCGAGCTTGATTTGTCCTATAACAAACTGAAGAGTATCC

CTACTGTCAATGAAAATTTGGAGAATTACTACCTCGAAGTCAATGAGCTTGAGAAGTTCGAT

GTTAAGTCTTTCTGTAAGATACTGGGTCCATTGTCATACAGCAAGATTAAACATCTTCGCTT

GGATGGGAATCCCTTGACTCAAAGCTCACTTCCCCCCGACATGTACGAATGCCTGAGGGTAG

CCAACGAAATCACAGTAAACGGAGGTGGCTCCTGAGCGATCGCTAAATACAGCAGCAATTGG

CAAGCTGCTTACATAGAACTCGCGGCGATTGGCATGCCGCCTTAAAATTTTTATTTTATTTT

TCTTTTCTTTTCCGAATCGGATTTTGTTTTTAATATTTCAAAAAAAAAAAAAAAAAAAAAAA

AAACGCGTCGAGGGGAATTAATTCTTGAAGACGAAAGGGCCAGGTGGCACTTTTCGGGGAAA

TGTGCGCGGAACCCCTATTTGTTTATTTTTCTAAATACATTCAAATATGTATCCGCTCATGA

GACAATAACCCTGATAAATGCTTCAATAATATTGAAAAAGGAAGAGTATGAGTATTCAACAT

TTCCGTGTCGCCCTTATTCCCTTTTTTGCGGCATTTTGCCTTCCTGTTTTTGCTCACCCAGA

AACGCTGGTGAAAGTAAAAGATGCTGAAGATCAGTTGGGTGCACGAGTGGGTTACATCGAAC

TGGATCTCAACAGCGGTAAGATCCTTGAGAGTTTTCGCCCCGAAGAACGTTTTCCAATGATG

AGCACTTTTAAAGTTCTGCTATGTGGCGCGGTATTATCCCGTGTTGACGCCGGGCAAGAGCA

ACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGAT

AACACTGCGGCCAACTTACTTCTGACAACGATCGGAGGACCGAAGGAGCTAACCGCTTTTTT

GCACAACATGGGGGATCATGTAACTCGCCTTGATCGTTGGGAACCGGAGCTGAATGAAGCCA
```

-continued

```
TACCAAACGACGAGCGTGACACCACGATGCCTGTAGCAATGGCAACAACGTTGCGCAAACTA

TTAACTGGCGAACTACTTACTCTAGCTTCCCGGCAACAATTAATAGACTGGATGGAGGCGGA

TAAAGTTGCAGGACCACTTCTGCGCTCGGCCCTTCCGGCTGGCTGGTTTATTGCTGATAAAT

CTGGAGCCGGTGAGCGTGGGTCTCGCGGTATCATTGCAGCACTGGGGCCAGATGGTAAGCCC

TCCCGTATCGTAGTTATCTACACGACGGGGAGTCAGGCAACTATGGATGAACGAAATAGACA

GATCGCTGAGATAGGTGCCTCACTGATTAAGCATTGGTAACTGTCAGACCAAGTTTACTCAT

ATATACTTTAGATTGATTTAAAACTTCATTTTTAATTTAAAAGGATCTAGGTGAAGATCCTT

TTTGATAATCTCATGACCAAAATCCCTTAACGTGAGTTTTCGTTCCACTGAGCGTCAGACCC

CGTAGAAAAGATCAAAGGATCTTCTTGAGATCCTTTTTTTCTGCGCGTAATCTGCTGCTTGC

AAACAAAAAAACCACCGCTACCAGCGGTGGTTTGTTTGCCGGATCAAGAGCTACCAACTCTT

TTTCCGAAGGTAACTGGCTTCAGCAGAGCGCAGATACCAAATACTGTCCTTCTAGTGTAGCC

GTAGTTAGGCCACCACTTCAAGAACTCTGTAGCACCGCCTACATACCTCGCTCTGCTAATCC

TGTTACCAGTGGCTGCTGCCAGTGGCGATAAGTCGTGTCTTACCGGGTTGGACTCAAGACGA

TAGTTACCGGATAAGGCGCAGCGGTCGGGCTGAACGGGGGGTTCGTGCACACAGCCCAGCTT

GGAGCGAACGACCTACACCGAACTGAGATACCTACAGCGTGAGCATTGAGAAAGCGCCACGC

TTCCCGAAGGGAGAAAGGCGGACAGGTATCCGGTAAGCGGCAGGGTCGGAACAGGAGAGCGC

ACGAGGGAGCTTCCAGGGGGAAACGCCTGGTATCTTTATAGTCCTGTCGGGTTTCGCCACCT

CTGACTTGAGCGTCGATTTTTGTGATGCTCGTCAGGGGGCGGAGCCTATGGAAAAACGCCA

GCAACGCGAGCTCTAATACGACTCACTATAG
```

In some embodiments, the synthetic oncolytic virus comprises LNP-replicon RNA-IL-12-serum albumin-lumican. In other embodiments, the synthetic oncolytic virus comprises TT3-LNP-repliconRNA-IL-12-serum albumin-lumican. In other embodiments, the synthetic oncolytic virus comprises TT3-LNP-mtReplicon RNA-IL-12-serum albumin-lumican. The retention of IL-12 in the tumor microenvironment may improve the efficacy and safety of the synthetic oncolytic virus.

In some instances, the replicon RNA may comprise one or more gene(s) of experimental or therapeutic interest. In some embodiments, the gene(s) of experimental or therapeutic interest encode cytokines, chemokines, or growth factors other than IL-12. Cytokines are known in the art, and the term itself refers to a generalized grouping of small proteins that are secreted by certain cells within the immune system and have an effect on other cells. Cytokines are known to enhance the cellular immune response and, as used herein, can include, but are not limited to, TNFα, IFN-γ, IFN-α, TGF-β, IL-1, IL-2, IL-4, IL-10, IL-13, IL-17, IL-18, and chemokines. Chemokines are useful for studies investigating response to infection, immune responses, inflammation, trauma, sepsis, cancer, and reproduction, among other applications. Chemokines are known in the art, and are a type of cytokines that induce chemotaxis in nearby responsive cells, typically of white blood cells, to sites of infection. Non-limiting examples of chemokines include, CCL14, CCL19, CCL20, CCL21, CCL25, CCL27, CXCL12, CXCL13, CXCL-8, CCL2, CCL3, CCL4, CCL5, CCL11, and CXCL10. Growth factors are known in the art, and the term itself is sometimes interchangeable with the term cytokines. As used herein, the term "growth factors" refers to a naturally occurring substance capable of signaling between cells and stimulating cellular growth. While cytokines may be growth factors, certain types of cytokines may also have an inhibitory effect on cell growth, thus differentiating the two terms. Non-limiting examples of growth factors include Adrenomedullin (AM), Angiopoietin (Ang), Autocrine motility factor, Bone morphogenetic proteins (BMPs), Ciliary neurotrophic factor (CNTF), Leukemia inhibitory factor (LIF), Interleukin-6 (IL-6), Macrophage colony-stimulating factor (m-CSF), Granulocyte colony-stimulating factor (G-CSF), Granulocyte macrophage colony-stimulating factor (GM-CSF), Epidermal growth factor (EGF), Ephrin A1, Ephrin A2, Ephrin A3, Ephrin A4, Ephrin A5, Ephrin B1, Ephrin B2, Ephrin B3, Erythropoietin (EPO), Fibroblast growth factor 1(FGF1), Fibroblast growth factor 2(FGF2), Fibroblast growth factor 3(FGF3), Fibroblast growth factor 4(FGF4), Fibroblast growth factor 5(FGF5), Fibroblast growth factor 6(FGF6), Fibroblast growth factor 7(FGF7), Fibroblast growth factor 8(FGF8), Fibroblast growth factor 9(FGF9), Fibroblast growth factor 10(FGF10), Fibroblast growth factor 11(FGF11), Fibroblast growth factor 12(FGF12), Fibroblast growth factor 13(FGF13), Fibroblast growth factor 14(FGF14), Fibroblast growth factor 15(FGF15), Fibroblast growth factor 16(FGF16), Fibroblast growth factor 17(FGF17), Fibroblast growth factor 18(FGF18), Fibroblast growth factor 19(FGF19), Fibroblast growth factor 20(FGF20), Fibroblast growth factor 21(FGF21), Fibroblast growth factor 22(FGF22), Fibroblast growth factor 23(FGF23), Fetal Bovine Somatotrophin (FBS), Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factor-1 (IGF-1), Insulin-like growth factor-2 (IGF-2), Interleukin-1 (IL-1),IL-2,IL-3, IL-4, IL-5, IL-6, IL-7, Keratinocyte growth factor (KGF), Migration-stimulating factor (MSF), Macrophage-stimulating protein (MSP), Myostatin (GDF-8), Neuregulin 1 (NRG1), Neuregulin 2 (NRG2), Neuregulin 3 (NRG3), Neuregulin 4 (NRG4), Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS), T-cell growth factor (TCGF), Thrombopoietin (TPO), Transforming growth factor alpha (TGF-α), Transforming growth factor beta (TGF-β), Tumor necrosis factor-alpha (TNF-α), and Vascular endothelial growth factor (VEGF).

II. Pharmaceutical Compositions

In some aspects, the present disclosure, at least in part, relates to a pharmaceutical composition, comprising the synthetic oncolytic virus, as described herein. The pharmaceutical composition described herein may further comprise a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used for in vivo administration must be sterile. This is readily accomplished by, for example, filtration through sterile filtration membranes. The synthetic oncolytic virus-containing compositions may be placed into a container having a sterile access port, for example, an intravenous solution bag or vial having a stopper pierceable by a hypodermic injection needle.

In some embodiments, the pharmaceutical composition to be used herein, can be formulated for intratumoral injection. Intratumoral injection, as used herein, refers to direct injections into the tumor, an anti-tumor composition (e g immunostimulatory synthetic oncolytic virus). A high concentration of composition can be achieved in situ, while using small amounts of drugs. Local delivery of immunotherapies allows multiple combination therapies, while preventing significant systemic exposure and off-target toxicities.

In other embodiments, the pharmaceutical composition can be formulated for intramuscular injection, intravenous injection, or subcutaneous injection.

The pharmaceutical compositions to be used in the present methods can comprise pharmaceutically acceptable carriers, buffer agents, excipients, salts, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises lipid nanoparticles which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

In other examples, the pharmaceutical composition described herein can be formulated in sustained-release format. Suitable examples of sustained-release preparations include semipermeable matrices of solid hydrophobic polymers containing the synthetic oncolytic virus which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

Suitable surface-active agents include, in particular, non-ionic agents, such as polyoxyethylenesorbitans (e.g., TWEEN™ 20, 40, 60, 80 or 85) and other sorbitans (e.g., SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets having a suitable size and can have a pH in the range of 5.5 to 8.0.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

III. Therapeutic Applications

The pharmaceutical compositions disclosed herein, comprising a synthetic oncolytic virus, can be used to treat cancer, for example, cancer immunotherapy.

To practice the method disclosed herein, an effective amount of any of the pharmaceutical compositions described herein can be administered to a subject (e.g., a human) in need of the treatment via a suitable route, such as intratumoral administration, by intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, synthetic oncolytic virus containing pharmaceutical composition can be aerosolized using a fluorocarbon formulation and a metered dose inhaler, or inhaled as a lyophilized and milled powder. In some examples, the pharmaceutical composition described herein is formulated for intratumoral injection. In particular examples, the pharmaceutical composition may be administered to a subject (e.g., a human patient) via a local route, for example, injected to a local site such as a tumor site or an infectious site.

As used herein, "an effective amount" refers to the amount of each active agent required to confer therapeutic effect on the subject, either alone or in combination with one or more other active agents. In some embodiments, the therapeutic effect is reduced tumor burden, reduction of cancer cells, or increased immune activity. Determination of whether an amount of synthetic oncolytic virus achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a synthetic oncolytic virus may be appropriate. Various formulations and devices for achieving sustained release are known in the art.

In some embodiments, the treatment is a single injection of the synthetic oncolytic virus containing pharmaceutical composition. In some embodiments, the single injection is administered intratumorally to the subject in need thereof.

In some example, dosages for a synthetic oncolytic virus as described herein may be determined empirically in individuals who have been given one or more administration(s) of synthetic oncolytic. Individuals are given incremental dosages of the synthetic oncolytic containing composition. To assess efficacy of the synthetic oncolytic virus, an indicator of the disease/disorder can be followed. For repeated administrations over several days or longer, depending on the condition, the treatment is sustained until a desired suppression of symptoms occurs or until sufficient therapeutic levels are achieved to alleviate a target disease or disorder, or a symptom thereof.

In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen of the synthetic oncolytic virus used can vary over time.

In some embodiments, the method described herein comprises administering to a subject in need of the treatment (e.g., a human patient) one or multiple doses of synthetic oncolytic virus-containing pharmaceutical composition.

For the purpose of the present disclosure, the appropriate dosage synthetic oncolytic virus as described herein will depend on the specific synthetic oncolytic virus, the type and severity of the disease/disorder, the synthetic oncolytic virus is administered for preventive or therapeutic purposes, previous therapy, the patient's clinical history and response to the synthetic oncolytic virus, and the discretion of the attending physician. A clinician may administer a synthetic oncolytic virus, until a dosage is reached that achieves the desired result. In some embodiments, the desired result is a decrease in tumor burden, a decrease in cancer cells, or increased immune activity. Methods of determining whether a dosage resulted in the desired result would be evident to one of skill in the art. Administration of one or more synthetic oncolytic virus can be continuous or intermittent, depending, for example, upon the recipient's physiological condition, whether the purpose of the administration is therapeutic or prophylactic, and other factors known to skilled practitioners. The administration synthetic oncolytic virus may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, a synthetic oncolytic virus-containing pharmaceutical composition as described herein are administered to a subject in need of the treatment at an amount sufficient to reduce tumor burden or cancer cell growth, by at least 5% (e.g., 10%, 20%, 30%, 40%, 50%, 60%, 70%, 80%, 90% or greater) in vivo. In other embodiments, the synthetic oncolytic virus-containing pharmaceutical compositions as described herein can be administered in an amount effective in increasing immune activity by at least 5%, 10%, 20%, 30%, 40%, 50%, 60%, 70%, 80%, 90% or greater.

The subject to be treated by the methods described herein can be a mammal, such as a human, farm animals, sport animals, pets, primates, horses, dogs, cats, mice and rats. In one embodiment, the subject is a human. The synthetic oncolytic virus-containing composition as described herein may be used for enhancing immune activity, for example, T cell activity, in a subject in need of the treatment.

In some embodiments, the subject may be a human patient having, suspected of having, or at risk for a cancer. Non limiting examples of cancers include melanoma, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, prostate cancer, vulval cancer, thyroid cancer, hepatic carcinoma, gastric cancer, and various types of head and neck cancer, including squamous cell head and neck cancer. In some embodiments, the cancer can be melanoma, lung cancer, colorectal cancer, renal-cell cancer, urothelial carcinoma, or Hodgkin's lymphoma.

A subject having a target disease or disorder (e.g., cancer) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices.

In some embodiments, a synthetic oncolytic virus-containing pharmaceutical composition may be co-used with another suitable therapeutic agent (e.g., an anti-cancer agent an anti-viral agent, or an anti-bacterial agent) and/or other agents that serve to enhance and/or complement the immunostimulatory effect of a synthetic oncolytic virus. In such combined therapy, the a synthetic oncolytic virus-containing composition and the additional therapeutic agent (e.g., an anti-cancer therapeutic agent or others described herein) may be administered to a subject in need of the treatment in a sequential manner, i.e., each therapeutic agent is administered at a different time. Alternatively, these therapeutic agents, or at least two of the agents, are administered to the subject in a substantially simultaneous manner Combination therapy can also embrace the administration of the agents described herein (e.g., a synthetic oncolytic virus containing pharmaceutical composition and an anti-cancer agent) in further combination with other biologically active ingredients (e.g., a different anti-cancer agent) and non-drug therapies (e.g., surgery).

It should be appreciated that any combination of a synthetic oncolytic virus-containing composition and another anti-cancer agent (e.g., a chemotherapeutic agent) may be used in any sequence for treating a cancer. The combinations described herein may be selected on the basis of a number of factors, which include but are not limited to the effectiveness of reducing tumor formation or tumor growth, reducing cancer cells, increasing immune activity, and/or alleviating at least one symptom associated with the cancer, or the effectiveness for mitigating the side effects of another agent of the combination. For example, a combined therapy described herein may reduce any of the side effects associated with each individual members of the combination, for example, a side effect associated with the anti-cancer agent.

In some embodiments, another anti-cancer therapeutic agent is a chemotherapy, a radiation therapy, a surgical therapy and/or an immunotherapy. Examples of the chemotherapeutic agents include, but are not limited to, Carboplatin or Cisplatin, Docetaxel, Gemcitabine, Nab-Paclitaxel, Paclitaxel, Pemetrexed, and Vinorelbine. Examples of radiation therapy include, but are not limited to, ionizing radiation, gamma-radiation, neutron beam radiotherapy, electron beam radiotherapy, proton therapy, brachytherapy, systemic radioactive isotopes and radiosensitizers. Examples of a surgical therapy include, but are not limited to, a curative surgery (e.g., tumor removal surgery), a preventive surgery, a laparoscopic surgery, and a laser surgery. Examples of an immunotherapy include, but are not limited to, adoptive cell transfer and therapeutic cancer vaccines.

Additional examples of chemotherapy include, but are not limited to, platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin HCl, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives); Purine antagonists (Thioguanine, Fludarabine, Cladribine, 6-Mercaptopurine, Pentostatin, clofarabine and relatives) and Pyrimidine antagonists (Cytarabine, Floxuridine, Azacitidine, Tegafur, Carmofur, Capecitabine, Gemcitabine, hydroxyurea, 5-Fluorouracil (5FU), and relatives); Alkylating agents, such as Nitrogen mustards (e.g., Cyclophosphamide, Melphalan, Chlorambucil, mechlorethamine, Ifosfamide, Trofosfamide, Prednimustine, Bendamustine, Uramustine, Estramustine, and relatives); nitrosoureas (e.g., Carmustine, Lomustine, Semustine, Fotemustine, Nimustine, Ranimustine, Streptozocin, and relatives); Triazenes (e.g., Dacarbazine, Altretamine, Temozolomide, and relatives); Alkyl sulphonates (e.g., Busulfan, Mannosulfan, Treosulfan, and relatives); Procarbazine; Mitobronitol, and Aziridines (e.g., Carboquone, Triaziquone, ThioTEPA, triethylenemalamine, and relatives); Antibiotics, such as Hydroxyurea, Anthracyclines (e.g., doxorubicin agent, daunorubicin, epirubicin and other derivatives); Anthracenediones (e.g., Mitoxantrone and relatives); *Streptomyces* family (e.g., Bleomycin, Mitomycin C, Actinomycin, Plicamycin); and Ultraviolet light.

III. Kits for Use in Therapy

The present disclosure also provides kits for use in immunotherapy against cancer (e.g., melanoma, lung cancer, colorectal cancer, or renal-cell cancer), and/or treating or reducing the risk for cancer. Such kits can include one or more containers comprising a synthetic oncolytic virus-containing pharmaceutical composition, e.g., any of those described herein.

In some embodiments, the kit can comprise instructions for use in accordance with any of the methods described herein. For example, the included instructions can comprise a description of administration of the a synthetic oncolytic virus-containing composition to treat, delay the onset, or alleviate a target disease as those described herein. The kit may further comprise a description of selecting an individual suitable for treatment based on identifying whether that individual has the target disease. In still other embodiments, the instructions comprise a description of administering the synthetic oncolytic virus-containing composition to an individual at risk of the target disease.

The instructions relating to the use of a synthetic oncolytic virus-containing composition generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with cancer, such as those described herein. Instructions may be provided for practicing any of the methods described herein.

The kits as described herein are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a synthetic oncolytic virus-containing composition such as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

IV. General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Materials and Methods
Cell Lines and Animals

Cell lines B16F10 (ATCC® CRL-6475™), HEK-blue-TLR2 (Invivogen), HEK-blue-TLR3 (Invivogen), HEK-blue-TLR7 (Invivogen), HEK-blue-TLR9 (Invivogen), Raw-Lucia ISG (Invivogen), and were cultured following vendor instructions (37° C., 5% CO2). Female C57BL/6J (JAX Stock No. 000664) mice 6-8 weeks of age were purchased and maintained in the animal facility at the Massachusetts Institute of Technology (MIT). All animal studies and procedures were carried out following federal, state, and local guidelines under an IACUC-approved animal protocol by Committee of Animal Care at MIT.
Antibodies, Staining, and FACS Analysis Antibodies against mouse Ly6c (HK1.4), CD11b (M1/70), CD11c (N418), F4/80 (BM8), MHC-II (M5/114.15.2), CD45 (30-F11), CD3 (17A2), CD4 (GK1.5), CD8 (53-6.7), NK1.1 (PK136), CD45.2 (104), CD24 (30-F1), XCR1 (ZET), CD64 (X54-5/7.1) were from Biolegend. Antibodies against mouse Ly6G (1A8), CD16/32 (2.4G2) and CD103 (M290) were from BD Biosciences. Antibodies against mouse Calreticulin (ab2907) was from Abcam. The live/dead dye (L34966) were from ThermoFisher.

The B16F10 melanoma tumor bearing mice were sacrificed and necropsied following federal, state, and local guidelines under an IACUC-approved animal protocol by Committee of Animal Care at MIT. Then the tumor draining lymph nodes were ground, and the tumors were sliced and digested by collagenase IV (1 mg/ml) for one hour for single cell suspensions. The single cells suspensions were filtered by 70 µm nylon constrainer and stained as described[10].

The stained samples were analyzed by FACS analyzer (LSR-II or LSR-II-Fortessa) from BD Biosciences. analyzed on a BD-LSRII Fortessa analyzer. All flow cytometry data were analyzed by FlowJo (Flowjo LLC) and the plots were prepared using GraphPad Prism.
Constructs, In Vitro Transcription, Capping/Methylating for Replicon RNA, and Neon Transfection Backbone of mutant replicon constructs were from an in vitro evolution in a previous study (in revision). The IL12-MSA and IL12-MSA-Lumican were amplified from plasmids from Prof. Dane Wittrup Lab, and engineered in the subgenomic region of mutant replicon.

Replicon RNAs were in vitro transcribed (IVT) from the templates of linearized VEE-constructs above using the MEGAscript™ T7 Transcription Kit (ThermoFisher) following the manufacturer's instructions. Resulting replicon RNAs were capped and methylated using the ScriptCap™ m7G Capping System and ScriptCap™ 2'-O-Methyltransferase Kit (Cellscript) according to the manufacturer's instructions. RNA purity was assessed by gel electrophoresis.

In vitro transfections were carried out using 5 µg RNA for per 500,000 cells in 100 µl R buffer of NEON electroporation kit (ThermoFisher) at the conditions of 1200 voltage, 20 milliseconds, and 1 pulse.
Formulations of Lipid Nanoparticles and Encapsulation of Replicon RNA For encapsulating 10 µg replicon RNA into DOTAP nanoparticle, a lipid mixture composed of 16.9375 µl DOTAP (Avanti, Cat #890890, 10 mg/ml), 15.965 µl DSPC (Avanti, Cat #850365, 3 mg/ml), 18.7675 µl cholesterol (Sigma-Aldrich, Cat #C8667, 6 mg/ml), 13.6 µl DSPE-PEG2000 (Avanti Cat #880128, 2.5 mg/ml) in a molar ratio of 40:10:48:2 was prepared in ethanol and evaporated under N2 till one third of the total initial volume remained. Then 10 µg replicon RNA (1 mg/ml) in 11.8 µl 0.1 M citrate buffer (PH 6.0) was added with pipetting, followed by a second addition of an additional 22 µl 0.1 M citrate buffer (PH 6.0) with pipetting. The mixture was shaken for an hour and then dialyzed against PBS for another hour at 25° C. in a 3,500 MWCO dialysis cassette.

Encapsulating replicon RNA into lipofectamine nanoparticle was following the instruction of Lipofectamine™ MessengerMAX™ Transfection Reagent (thermofisher.com/order/catalog/product/LMRNA008).

For encapsulating 10 µg replicon RNA into TT3 nanoparticle, a lipid mixture composed of 10 µl TT3 (10 mg/ml)[11], 8.04 µl DOPE (Avanti, Cat #850725, 10 mg/me, 5.572 µl cholesterol (Sigma-Aldrich, Cat #C8667, 10 mg/ml), 3.452 µl C14-PEG2000 (Avanti Cat #880150, 2 mg/ml) in a molar ratio of 20:30:40:0.75 was prepared in 10.437 µl ethanol. The mixture were added 4.167 µl citrate buffer (PH 3.0, 10 mM). Then 10 µg replicon RNA (1 mg/ml) in 31.667 µl citrate buffer (PH 3.0, 10 mM) was added with pipetting. The mixture was dialyzed against PBS for 80 minutes at 25° C. in a 3,500 MWCO dialysis cassette.

The resulting replicon-loaded lipid nanoparticles were aliquoted in appropriate dosages for intratumoral injection (10 µg/mouse) and for transfection in vitro (5 µg/0.5 million cells in 500 µl media).
Annexin V/PI Staining, ATP Assay, and ELISA Annexin V/PI staining follows the instruction of the kit from Biolegend (Cat #640932). Extracellular ATP was assayed by ENLITEN® ATP Assay System (Promega). HMGB1, CCL5, IFNα2, IL12, IFNγ were measured by ELISA kits from Chondrex (Cat #6010, HMGB1), R & D System (Cat #DY478, CCL5), Abcam (Cat #ab215409, IFNα2), and Biolegend (Cat #88-7121-88, IL12, Cat #88-7314-88, IFNγ) and followed their manuals.
RNA Extraction and Quantitative PCR Analysis To quantify levels of RNA transcripts, total RNA was extracted from cells or tumors transfected with LNP-replicon RNA as indicated and reverse transcribed by a TaqMan™ Reverse Transcription Reagents Kit (ABI Catalog No. N8080234), followed by amplification with Sybr Green Master Mix (Roche) and specific primers for Stat1 (Cat #MP215434), Stat2 (Cat #MP215434), IRF9 (Cat #MP206708), IRF3 (Cat #MP206702), cGAS (Cat #MP214711) and detected by a Roche LightCycler 480. The Ct values were normalized with housekeeping gene mouse Actin B for comparison.

Example 1: Synthetic all in One LNP Replicon RNA for Cancer Immunotherapy

Therapeutic processes can be simplified and therapeutic efficacy can be amplified by synthetic multifunctional lipid nanoparticles (LNPs) encapsulating replicon RNA, with the lipid and RNA components each serving multiple roles: a lipid formulation that both promotes cellular uptake/cytosolic delivery of RNA while also directly triggering immunogenic cell death. In tandem, this LNP delivers self-amplifying replicon RNA that both encodes immunomodulatory therapeutic proteins and directly provides immunostimulation amplifying the subsequent immune response. Functionally, this synthetic LNP replicon RNA should induce local immunogenic cell death in tumor and also express immunomodulatory decently in transfected cells Immunogenic cell death could enhance tumor infiltration by immune cells and provide a reservoir of tumor-specific antigens that could be cross presented to prime new T cells responses. LNP formulations containing the cationic lipid TT3 was identified as being especially relevant for these goals: 3 cationic lipid nanoparticles, each comprising a key cationic lipid-DOTAP, Lipofectamine (Lipo) or TT3, were compared. As the RNA cargo, an alphavirus replicon, derived from Venezuela Equine Encephalitis virus where the structural proteins were replaced by a cargo gene of interest inserted under the subgenomic promoter, was employed. When formulated with this self-amplifying replicon RNA (LNP-mtRep), the DOTAP, lipo, and TT3 lipid formulations formed particles with mean diameters of 97, 46, and 105 nm nanoparticles, with zeta potentials of +22.9, −6.7, and +4.3 mv, respectively (FIG. 1G-1H). The toxicity of the "empty" vs. RNA-loaded (mtRep) LNPs was assessed by incubating each formulation with B16F10 melanoma tumor cells in vitro. This assay revealed that viability significantly decreased for cells treated with TT3 LNPs, and mtRep synergized with TT3 to promote further tumor cell killing at 3-day post transfection (FIG. 1A). TT3 LNPs were more effective than DOTAP or Lipo in promoting tumor cell death. Notably, electroporation of replicon directly into tumor cells was relatively nontoxic, indicating that cell killing is promoted by the LNP delivery. To determine whether TT3 LNP-delivered replicons could drive cargo gene expression prior to cell death, we evaluated expression of the reporter gene GFP following LNP(mtRep) treatment. TT3-mtRep treatment led to ~35.4% of B16F10 cells to express GFP 12 hours post transfection, lower than electroporation (~90%), but significantly better than DOTAP-mtRep (~0.05%) or Lipo-mtRep (~7.6%) treatments (FIG. 1B). Consistent with FIG. 1A, the cells transfected with TT3 nanoparticles showed a large population of Annexin V+/PI+ dead cells and mtRep again synergized to this cell death (FIG. 1C).

To determine if the cell death triggered by TT3(mtRep) is a type of immunogenic cell death (ICD), calreticulin (CRT), which generally stays on endoplasmic reticulum (ER) and traffics to cell surface as an eat-me signal during ICD1, was measured. TT3 and mtRep synergized to promote the CRT trafficking to cell surfaces (FIG. 1D). Extracellular ATP activates the NLRP3 inflammasome2 and extracellular HMGB1 mediates inflammation3 during ICD. TT3, TT3-mtRep, and TT3-deRep effectively induced ATP and HMGB1 release. (FIGS. 1E and 1F). Taken it together, TT3-mtRep RNA is a promising oncolytic formulation that could induce immunogenic cell death while also leading to transient expression of cargo genes encoded by the replicon.

Example 2: Replicon RNA Triggers TLR3 Signaling and Induces the ISGF3 Complex Linked to Necrotic Cell Death To determine the mechanisms underlying the synergy of cell death by replicon and TT3 LNP, DOTAP, Lipo, or TT3 nanoparticles with or without encapsulated mtRep encoding a reporter gene (or encapsulating a mutant "dead" replicon (deRep) that lacks functional gene expression) were transfected into reporter cells HEK-TLR2, HEK-TLR3, HEK-TLR7, or HEK-TLR9 (invivogen.com). Both Lipo and TT3 LNPs carrying mtRep or deRep activated TLR3 signaling, but none of the other TLRs tested were stimulated (FIG. 2A-D). When tested on Raw-Lucia-ISG reporter cells (invivogen.com), interferon stimulated genes were significantly induced by these same LNP formulations (FIG. 2E). These data suggest TLR3 recognizes replicon RNA and induces interferon responses in response to LNP-mediated delivery.

Since replicon RNA activates TLR3 signaling through TRIF for Type I interferon production[4] that leads to activation of the ISGF3 (Stat 1/Stat 2/IRF9) complex for necrotic cell death[5], we assayed mRNA transcript levels of ISGF3 complex components, Stat1, Stat2, and IRF9, as well as STING pathway genes, IRF3 and cGAS by qPCR. TT3 nanoparticles encapsulating mtRep or deRep increased ~6, ~16, and ~3 times the levels of Stat1, Stat2, IRF9 over untreated controls (FIG. 2F-H), respectively. In contrast, it had no effects on the transcription of IRF3 or cGAS (FIG. 2I-J). The DOTAP and Lipo formulations failed to induce the ISGF3 complex, likely because of low transfection efficiency of replicon RNA by these nanoparticles (FIG. 1B). These data suggested that mtRep and deRep likely activate TLR3 signaling and induce ISGF3 complex to promote necrotic cell death, a type of immunogenic cell death.

Example 3: TT3-mtRep Recruits Immune Cells and Regresses Established Tumors

Whether TT3-mtRep has effects on immunogenic cell death and expression of cargo genes in vivo was of interest. The absolute number of Ly6c$^{lo}$ Ly6G$^+$ granulocytic populations, which are associated with responses to necrotic cell death[6], was measured in tumors at 3-day post intratumoral injection of TT3 nanoparticles encapsulating wild type replicon RNA (wtRep), with another mutant replicon RNA (mt2Rep), and the mutant replicon (mtRep) used above. Unexpectedly, the mtRep showed significantly greater (~2 fold higher) recruitment of this granulocytic population to tumors (FIG. 3A), and better expression of the reporter gene mCherry encoded by the subgenomic promoter (FIG. 3B). Thus, TT3-mtRep induces immunogenic cell death with decent cargo gene expression. In vivo studies using TT3-mtRep were carried out subsequently.

The expression level of Stat1/Stat2/IRF9 as well as STING signaling genes IRF3 and cGAS in vivo following intratumoral LNP delivery of replicons was measured. Consistent with the FIG. 2F-J in vitro, tumors injected with TT3-mtRep expressed significantly higher Stat1/Stat2/IRF9 (ISGF3 complex), but with comparable levels of IRF3 and cGAS (FIG. 3C), suggesting administration of TT3-mtRep also initiated necrotic cell death in vivo.

To better understand the effects of TT3-mtRep to immune composition in tumor, immune cells such as granulocytes (CD45$^+$ CD11b$^+$ Ly6c$^{lo}$ Ly6G$^+$), M-MDSC (CD45$^+$ CD11b$^+$ Ly6c$^{hi}$ Ly6G$^+$), Monocytes (D45$^+$ CD11b$^+$ Ly6c$^{lo}$ Ly6G$^-$), Macrophages (CD45$^+$ CD11b$^+$ Ly6c$^-$ Ly6G$^-$ F4/80$^+$), CD4 T (CD45$^+$ CD3ε$^+$ CD4$^+$), CD8 T (CD45$^+$ CD3ε$^+$ CD8$^+$), NK (CD45$^+$ CD3ε$^-$ NK1.1$^+$), NKT (CD45$^+$ CD3ε$^+$ NK1.11$^+$), conventional DC1 (cDC1, CD45$^+$ CD11c$^+$ MHC-II$^+$ CD24$^+$ CD64$^-$ CD103$^+$ CD11b$^-$ XCR1$^{hi}$), and conventional DC2 (cDC2, CD45$^+$ CD11c$^+$ MHC-II$^+$ CD24$^+$ CD64$^-$ CD103$^+$ CD11b$^+$XCR1$^{lo}$), ware mapped and quantified in the tumors at 1 day (FIG. 3D) and 3 days (FIG. 3E) post one injection, and at 1 day (FIG. 3F) post three sequential injections of LNP-replicon RNA. In this dynamic analysis of immune compositions in tumor, the granulocytes and the cDC1 were quickly recruited and decreased at 1 day post injection of replicon RNA, respectively (FIG. 3C), suggesting granulocytes might be early event and cDC1 likely start trafficking to tumor draining lymph node (TDLN) in response to LNP-replicon RNA. At 3 days post injection of replicon RNA, CD4 T, CD8 T, NK, and NKT cells were also recruited (FIG. 3D). When administering 3 sequential injections of LNP-replicon RNA, monocytes increased and macrophages decreased, but less significant changes were observed in lymphoid cells, such as CD4 T, NK, and NKT cells (FIG. 3E). As effects of these ~3 sequential injections, there was ~10% more cell death (FIG. 3F), ~4 times higher tumor infiltrating immune cells (FIG. 3G), and a 2-fold reduction in tumor weight (FIG. 3H) in the samples of TT3-mtRep group, resulting in significant regression of tumor growth (FIG. 3I). Consistent with the NK, and NKT cells come up along with the treatments of TT3-mtRep, CCL5 expression was significantly induced (FIG. 3I), which is mainly secreted by NK[7] and activated CD8 T cells (rstats.immgen.org/Skyline/skyline.html). These data indicate TT3-mtRep induced immunogenic cell death in tumors with expression of cargo genes as observed in FIG. 1 and FIG. 2 in vitro. Most importantly, TT3-mtRep significantly modulated the tumor microenvironment, and led to tumor recruitment of CD8 T cells and NK cells.

Example 4: TT3-mtRep Encoding with IL12-MSA or IL12-MSA-Lumican Effectively Modulates Tumor Microenvironments and Immune Composition While intratumoral injection of TT3(mtRep) encoding reporter genes alone led to tumor growth delay, encoding immunomodulatory proteins in the replicon could lead to further immunostimulation and enhancements of anti-tumor immunity. An attractive candidate is IL-12, which could polarize CD4 T helpers to Th1 and enhance cytotoxicity effects of NK and CD8 T cells[8]. One of the subunit of IL12, also named as IL12b or IL12p40, is mainly secreted from antigen presentation cells (CD8[+] DCs) (rstats.immgen.org/Skyline/skyline.html), which could be functionally activated by Type I interferon[9]. However, the interferon α2 (IFNα2), a main form of Type I interferon, is low either in the serum (FIG. 4A) or in the tumors (FIG. 4B) at day 1 and day 3 following TT3-mtRep injections, suggesting IL-12 secreted by DCs may still be low in the tumor microenvironment (TME). Thus, IL12-MSA or IL12-MSA-Lumican that fused IL12α (P30), IL12β (P40) with murine serum albumin (MSA), or with MSA and Lumican was engineered. Lumican is an endogenous collagen-binding protein, which we reasoned would promote retention of expressed IL-12 in the TME to enhance efficacy and safety of the replicon therapy. The replicon constructs were transfected in B16F10 cells in vitro by NEON transfection and we validated IL12 secretion in these transfected cells by ELISA (FIG. 4C).

Consistently, tumors injected with TT3-mtRep encoding IL12-MSA (TT3-mtRep-IL12-MSA) or IL12-MSA-Lumican (TT3-mtRep-IL12-MSA-Lumican) expressed high levels of IL12 in vivo, reaching 40 ng/mg in tumors (FIG. 4D). Comparing immune composition in tumor at day 1 post injections, granulocytes was 1.5-3 times increased in the tumors treated with TT3-mtRep expressing IL12-MSA and IL12-MSA-Lumican, in contrast to the group treated with TT3-mtRep encoding with reporter gene mCherry (FIG. 4E). At day 3, IL12-MSA and IL12-MSA-Lumican groups recruited ~2-3 times higher granulocytes, CD8 T cells, and cDC2 cells to tumors compared to replicons encoding an irrelevant reporter gene (FIG. 4F). Interestingly, tumors treated with TT3-mtRep encoding reporter genes, IL12-MSA, or IL12-MSA-Lumican all showed decreases of cDC1 cells in comparison to the untreated group (FIG. 4E-4F). To determine if cDC1 were trafficking to the TDLN, we numerated the cDC1 cells in it and showed the cDC1 cells in lymph nodes significantly increased after TT3-mtRep treatment, no matter what cargo gene was encoded (FIG. 4G). Increases of cDC1 cells continued in the IL12-MSA group (FIG. 4G).

Figure 5B:
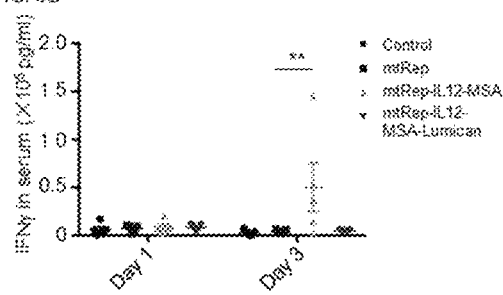
Figure 5C:
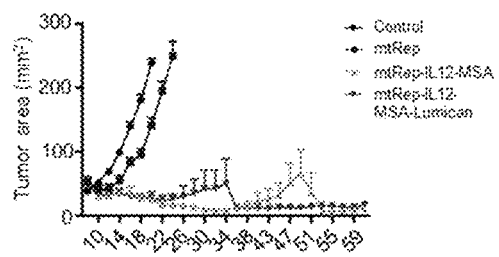
Figure 5D:
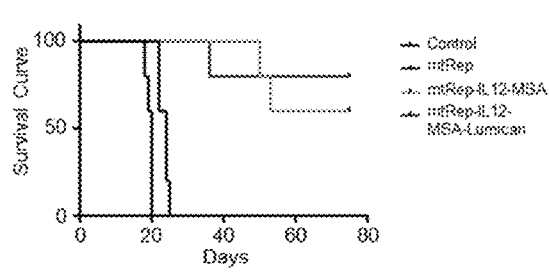
Figure 5E:
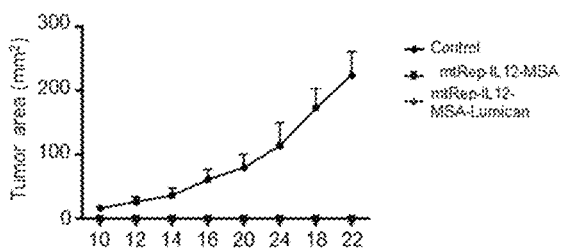

Example 5: Immunomodulatory IL12 and ICD Induced by TT3-mtRep Effectively Eradicate B16F10 Tumor As administrating IL12 protein has severe side effects in clinic studies, we measured the body weight changes of tumor bearing mice treated with replicon-encoded IL-12. The mtRep-IL12-MSA group had ~5% body loss that lasted a week. In contrast, mtRep and mtRep-IL12-MSA-Lumican groups had only ~2% body loss and recovered in a few days (FIG. 5A). Consistently, we failed to measure IL-6 or TNFα in serum at day 1 or day 3 post injection of mtRep-IL12-MSA or mtRep-IL12-MSA-Lumican (data not shown). But, we did observe significant increases of IFN-γ in serum in the group of mtRep-IL12-MSA (FIG. 5B), consistent with the body loss in FIG. 5A. Interestingly, the replicons expressing IL12-MSA or IL12-MSA-Lumican showed dramatic tumor regression, even to large established tumors with sizes at treatment of 50 mm$^2$ (FIG. 5C). The tumor bearing mice treated with TT3-mtRep encoding with IL12-MSA and IL12-MSA-Lumican were 60% and 80% tumor free at 75 days post B16F10 injection, respectively. To determine if these cured mice had elicited a systemic immune response that could prevent B16F10 tumor recurrence, these mice were challenged with 0.1 million B16F10 cells in opposite flank. As expected, all of the cured mice rejected the B16F10 tumor in comparison of the naïve mice that quickly developed of B16F10 tumor. These data indicate that synergy of immunomodulatory IL12 and ICD (immunogenic cell death) could effectively eradicate B16F10 tumor and induce systemic immune responses to prevent the recurrence of B16F10 tumor.

REFERENCES

1 Yun, Y. R. et al. Fibroblast growth factors: biology, function, and application for tissue regeneration. *J Tissue Eng* 2010, 218142, doi:10.4061/2010/218142 (2010).
2 Zha, Q. B. et al. ATP-Induced Inflammasome Activation and Pyroptosis Is Regulated by AMP-Activated Protein Kinase in Macrophages. *Front Immunol* 7, 597, doi:10.3389/fimmu.2016.00597 (2016).
3 Magna, M. & Pisetsky, D. S. The role of HMGB1 in the pathogenesis of inflammatory and autoimmune diseases. *Mol Med* 20, 138-146, doi:10.2119/molmed.2013.00164 (2014).
4 Kawai, T. & Akira, S. TLR signaling. *Cell Death Differ* 13, 816-825, doi:10.1038/sj.cdd.4401850 (2006).
5 McComb, S. et al. Type-I interferon signaling through ISGF3 complex is required for sustained Rip3 activation and necroptosis in macrophages. *Proc Natl Acad Sci USA* 111, E3206-3213, doi:10.1073/pnas.1407068111 (2014).
6 Haverkamp, J. M. et al. Myeloid-derived suppressor activity is mediated by monocytic lineages maintained by continuous inhibition of extrinsic and intrinsic death pathways. *Immunity* 41, 947-959, doi:10.1016/j.immuni.2014.10.020 (2014).
7 Bottcher, J. P. et al. N K Cells Stimulate Recruitment of cDC1 into the Tumor Microenvironment Promoting Cancer Immune Control. *Cell* 172, 1022-1037 e1014, doi:10.1016/j.cell.2018.01.004 (2018).
8 Lasek, W., Zagozdzon, R. & Jakobisiak, M. Interleukin 12: still a promising candidate for tumor immunotherapy? *Cancer Immunol Immunother* 63, 419-435, doi:10.1007/s00262-014-1523-1 (2014).
9 Montoya, M. et al. Type I interferons produced by dendritic cells promote their phenotypic and functional activation. *Blood* 99, 3263-3271, doi:DOI 10.1182/blood.V99.9.3263 (2002).
10 Li, Y. et al. Persistent Antigen and Prolonged AKT-mTORC1 Activation Underlie Memory CD8 T Cell Impairment in the Absence of CD4 T Cells. *J Immunol* 195, 1591-1598, doi:10.4049/jimmunol.1500451 (2015).
11 Li, B. et al. An Orthogonal Array Optimization of Lipid-like Nanoparticles for mRNA Delivery in Vivo. *Nano Lett* 15, 8099-8107, doi:10.1021/acs.nanolett.5b03528 (2015).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A synthetic oncolytic virus, comprising:
   (i) a lipid nanoparticle comprising N1,N3,N5-tris(3-(didodecylamino)propyl)benzene-1,3,5-tricarboxamide (TT3); and
   (ii) a self-amplifying replicon RNA comprising a sequence that encodes an interleukin (IL)-12 molecule; and
   wherein the IL-12 molecule is expressed by the self-amplifying replicon RNA.

2. The synthetic oncolytic virus of claim 1, wherein the lipid nanoparticle further comprises one or more types of lipid, where the one or more types of lipid comprises a cationic lipid.

3. The synthetic oncolytic virus of claim 1, wherein the lipid nanoparticle further comprises 1,2-Dioleoyl-sn-glycero-3-phosphoethanolamine (DOPE), cholesterol, and C14-PEG2000.

4. The synthetic oncolytic virus of claim 1, wherein the self-amplifying replicon RNA is derived from an alphavirus or a hepatitis C virus.

5. The synthetic oncolytic virus of claim 4, wherein the alphavirus is Venezuela Equine Encephalitis virus, Semliki Forest virus, or Sindbis virus.

6. The synthetic oncolytic virus of claim 1, wherein the sequence that encodes the IL-12 molecule is located in a subgenomic region of the self-amplifying replicon RNA.

7. The synthetic oncolytic virus of claim 1, wherein the self-amplifying replicon RNA comprises a nucleotide sequence that has at least 90% sequence identity to the sequence set forth in SEQ ID NO: 1.

8. The synthetic oncolytic virus of claim 7, wherein the self-amplifying replicon RNA comprises a point mutation of G3936C and/or A4758G of SEQ ID NO: 1.

9. The synthetic oncolytic virus of claim 1, wherein the self-amplifying replicon RNA further comprises a serum albumin coding sequence.

10. The synthetic oncolytic virus of claim 1, wherein the self-amplifying replicon RNA further comprises a lumican coding sequence.

11. The synthetic oncolytic virus of claim 1, wherein the IL-12 molecule is IL-12, an IL-12 subunit, or a mutant IL-12 molecule that retains the immunomodulatory function.

12. The synthetic oncolytic virus of claim 11, wherein the IL-12 molecule comprises IL-12α and/or IL-12β subunits.

13. The synthetic oncolytic virus of claim 1, wherein the lipid nanoparticle has a diameter of about 100-120 nm.

14. The synthetic oncolytic virus of claim 1, wherein the lipid nanoparticle has a zeta potential of about 3-6 mv.

15. The synthetic oncolytic virus of claim 1, wherein the lipid nanoparticle and the self-amplifying replicon RNA have a mass ratio of about 1:1.

16. A pharmaceutical composition, comprising the synthetic oncolytic virus of claim 1 and a pharmaceutically acceptable carrier.

17. The pharmaceutical composition of claim 16, wherein the pharmaceutical composition is formulated for intratumoral injection.

18. The synthetic oncolytic virus of claim 1, wherein the lipid nanoparticle further comprises 1,2-Dioleoyl-sn-glycero-3-phosphoethanolamine (DOPE) and cholesterol.

19. The pharmaceutical composition of claim 16, wherein the lipid nanoparticle further comprises 1,2-Dioleoyl-sn-glycero-3-phosphoethanolamine (DOPE) and cholesterol.

20. The pharmaceutical composition of claim 19, further comprising C14-PEG2000.

21. A pharmaceutical composition, comprising a synthetic oncolytic virus and a pharmaceutically acceptable carrier;
   wherein the synthetic oncolytic virus comprises:
   (i) a lipid nanoparticle comprising TT3, 1,2-Dioleoyl-sn-glycero-3-phosphoethanolamine (DOPE), and cholesterol; and
   (ii) a self-amplifying replicon RNA comprising a sequence that encodes an interleukin (IL)-12 molecule;
   wherein the self-amplifying replicon RNA comprises a nucleotide sequence that has at least 90% sequence identity to the sequence set forth in SEQ ID NO: 1;
   wherein the lipid nanoparticle is capable of triggering immunogenic cell death;
   wherein the IL-12 molecule is expressed by the self-amplifying replicon RNA; and
   wherein the pharmaceutical composition further comprises C14-PEG2000.

22. The synthetic oncolytic virus of claim 1, wherein the lipid nanoparticle is capable of triggering immunogenic cell death.

* * * * *

UNITED STATES PATENT AND TRADEMARK OFFICE
CERTIFICATE OF CORRECTION

| | |
|---|---|
| PATENT NO. | : 11,717,548 B2 |
| APPLICATION NO. | : 16/739407 |
| DATED | : August 8, 2023 |
| INVENTOR(S) | : Darrell J. Irvine et al. |

It is certified that error appears in the above-identified patent and that said Letters Patent is hereby corrected as shown below:

In the Specification

At Column 1, Lines 14-17, the paragraph under the heading "FEDERALLY SPONSORED RESEARCH":
"This invention was made with Government support under Grant No. R01 CA206218 awarded by the National Institutes of Health (NIH). The Government has certain rights in the invention."

Should read:
--This invention was made with government support under CA206218 awarded by the National Institutes of Health. The government has certain rights in the invention.--

Signed and Sealed this
Twenty-first Day of November, 2023

Katherine Kelly Vidal
*Director of the United States Patent and Trademark Office*

SEQUENCE LISTING

<160> NUMBER OF SEQ ID NOS: 5

<210> SEQ ID NO 1
<211> LENGTH: 10276
<212> TYPE: DNA
<213> ORGANISM: Unknown
<220> FEATURE:
<223> OTHER INFORMATION: VEE virus

<400> SEQUENCE: 1

| | | | | | |
|---|---|---|---|---|---|
| atgggcggcg | catgagagaa | gcccagacca | attacctacc | caaaatggag | aaagttcacg | 60 |
| ttgacatcga | ggaagacagc | ccattcctca | gagctttgca | gcggagcttc | ccgcagtttg | 120 |
| aggtagaagc | caagcaggtc | actgataatg | accatgctaa | tgccagagcg | ttttcgcatc | 180 |
| tggcttcaaa | actgatcgaa | acggaggtgg | acccatccga | cacgatcctt | gacattggaa | 240 |
| gtgcgcccgc | ccgcagaatg | tattctaagc | acaagtatca | ttgtatctgt | ccgatgagat | 300 |
| gtgcggaaga | tccggacaga | ttgtataagt | atgcaactaa | gctgaagaaa | aactgtaagg | 360 |
| aaataactga | taaggaattg | gacaagaaaa | tgaaggagct | ggccgccgtc | atgagcgacc | 420 |
| ctgacctgga | aactgagact | atgtgcctcc | acgacgacga | gtcgtgtcgc | tacgaagggc | 480 |
| aagtcgctgt | ttaccaggat | gtatacgcgg | ttgacggacc | gacaagtctc | tatcaccaag | 540 |
| ccaataaggg | agttagagtc | gcctactgga | taggctttga | caccacccct | tttatgttta | 600 |
| agaacttggc | tggagcatat | ccatcatact | ctaccaactg | ggccgacgaa | accgtgttaa | 660 |
| cggctcgtaa | cataggccta | tgcagctctg | acgttatgga | gcggtcacgt | agagggatgt | 720 |
| ccattcttag | aaagaagtat | ttgaaaccat | ccaacaatgt | tctattctct | gttggctcga | 780 |
| ccatctacca | cgagaagagg | gacttactga | ggagctggca | cctgccgtct | gtatttcact | 840 |
| tacgtggcaa | gcaaaattac | acatgtcggt | gtgagactat | agttagttgc | gacgggtacg | 900 |
| tcgttaaaag | aatagctatc | agtccaggcc | tgtatgggaa | gccttcaggc | tatgctgcta | 960 |
| cgatgcaccg | cgagggattc | ttgtgctgca | aagtgacaga | cacattgaac | ggggagaggg | 1020 |
| tctcttttcc | cgtgtgcacg | tatgtgccag | ctacattgtg | tgaccaaatg | actggcatac | 1080 |
| tggcaacaga | tgtcagtgcg | gacgacgcgc | aaaaactgct | ggttgggctc | aaccagcgta | 1140 |
| tagtcgtcaa | cggtcgcacc | cagagaaaca | ccaataccat | gaaaaattac | cttttgcccg | 1200 |
| tagtggccca | ggcatttgct | aggtgggcaa | aggaatataa | ggaagatcaa | gaagatgaaa | 1260 |
| ggccactagg | actacgagat | agacagttag | tcatggggtg | ttgttgggct | tttagaaggc | 1320 |
| acaagataac | atctatttat | aagcgcccgg | atacccaaac | catcatcaaa | gtgaacagcg | 1380 |
| atttccactc | attcgtgctg | cccaggatag | cagtaacac | attggagatc | gggctgagaa | 1440 |
| caagaatcag | gaaaatgtta | gaggagcaca | aggagccgtc | acctctcatt | accgccgagg | 1500 |
| acgtacaaga | agctaagtgc | gcagccgatg | aggctaagga | ggtgcgtgaa | gccgaggagt | 1560 |
| tgcgcgcagc | tctaccacct | ttggcagctg | atgttgagga | gcccactctg | gaggcagacg | 1620 |
| tcgacttgat | gttacaagag | gctggggccg | gctcagtgga | gacacctgt | ggcttgataa | 1680 |
| aggttaccag | ctacgatggc | gaggacaaga | tcggctctta | cgctgtgctt | tctccgcagg | 1740 |
| ctgtactcaa | gagtgaaaaa | ttatcttgca | tccaccctct | cgctgaacaa | gtcatagtga | 1800 |
| taacacactc | tggccgaaaa | gggcgttatg | ccgtggaacc | ataccatggt | aaagtagtgg | 1860 |
| tgccagaggg | acatgcaata | cccgtccagg | actttcaagc | tctgagtgaa | agtgccacca | 1920 |
| ttgtgtacaa | cgaacgtgag | ttcgtaaaca | ggtacctgca | ccatattgcc | acacatggag | 1980 |
| gagcgctgaa | cactgatgaa | gaatattaca | aaactgtcaa | gcccagcgag | cacgacggcg | 2040 |

```
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa ccatagggt gtatggcgtg ccaggatcag     2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg     2340 ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttttaac atgatgtgcc    2520 tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa     2640 cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg     2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt gggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgcttag     3480 tcctccacca taatgaacac ccacagagtg actttcttc attcgtcagc aaattgaagg     3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaattctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggagggtg tgcggagcgc     4140 tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
```

```
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacccct ggaggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccacccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc tgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgcccctgca agctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggccttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggtttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
```

```
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aggagtcaa atcggacaaa ttaatggcag     7140
acaggtgcgc cacctggttg aatatggaag tcaagattat agatgctgtg gtgggcgaga    7200
aagcgcctta tttctgtgga gggttttattt tgtgtgactc cgtgaccggc acagcgtgcc   7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaaccgta ggaacttcca    7440
tcatagttat ggccatgact actctagcta gcagtgttaa atcattcagc tacctgagag    7500
gggcccctat aactctctac ggctaacctg aatggactac gacatagtct agtccgccaa    7560
gtctagcata tgggcgcgcc ctcagcatcg attgaattgg ccaccatggt gagcaagggc    7620
gaggaggata acatggccat catcaaggag ttcatgcgct tcaaggtgca catggagggc    7680
tccgtgaacg gccacgagtt cgagatcgag ggcgagggcg agggccgccc ctacgagggc    7740
acccagaccg ccaagctgaa ggtgaccaag ggtggccccc tgcccttcgc ctgggacatc    7800
ctgtcccctc agttcatgta cggctccaag gcctacgtga agcacccgc cgacatcccc      7860 gactacttga agctgtcctt ccccgagggc ttcaagtggg agcgcgtgat gaacttcgag    7920
gacggcggcg tggtgaccgt gacccaggac tcctccctgc aggacggcga gttcatctac    7980
aaggtgaagc tgcgcggcac caacttcccc tccgacggcc ccgtaatgca gaagaagacc    8040
atgggctggg aggcctcctc cgagcggatg taccccgagg acggcgccct gaagggcgag    8100
atcaagcaga ggctgaagct gaaggacggc ggccactacg acgctgaggt caagaccacc    8160
tacaaggcca agaagcccgt gcagctgccc ggcgcctaca acgtcaacat caagttggac    8220
atcacctccc acaacgagga ctacaccatc gtggaacagt acgaacgcgc cgagggccgc    8280
cactccaccg gcggcatgga cgagctgtac aagtaggaat tggcaagctg cttacataga    8340
actcgcggcg attggcatgc cgccttaaaa ttttattt attttctttt tcttttccga      8400
atcggatttt gttttaata tttcaaaaaa aaaaaaaaa aaaaaaaaa cgcgtcgagg       8460 ggaattaatt cttgaagacg aaagggccag gtggcacttt cgggaaat gtgcgcggaa     8520 cccctattg tttattttt taaatacatt caaatatgta tccgctcatg agacaataac      8580
cctgataaat gcttcaataa tattgaaaaa ggaagagtat gagtattcaa catttccgtg    8640
tcgcccttat tccctttttt gcggcatttt gccttcctgt ttttgctcac ccagaaacgc    8700
tggtgaaagt aaaagatgct gaagatcagt tgggtgcacg agtgggttac atcgaactgg    8760
atctcaacag cggtaagatc cttgagagtt ttcgccccga agaacgtttt ccaatgatga    8820 gcactttta agttctgcta tgtggcgcgg tattatcccg tgttgacgcc gggcaagagc      8880
aactcggtcg ccgcatacac tattctcaga atgacttggt tgagtactca ccagtcacag    8940
aaaagcatct tacgatggc atgacagtaa gagaattatg cagtgctgcc ataaccatga    9000
gtgataacac tgcggccaac ttacttctga caacgatcgg aggaccgaag gagctaaccg    9060
cttttttgca acatggggg gatcatgtaa ctcgccttga tcgttgggaa ccggagctga    9120
```

| | |
|---|---|
| atgaagccat accaaacgac gagcgtgaca ccacgatgcc tgtagcaatg caacaacgt | 9180 |
| tgcgcaaact attaactggc gaactactta ctctagcttc ccggcaacaa ttaatagact | 9240 |
| ggatggaggc ggataaagtt gcaggaccac ttctgcgctc ggcccttccg gctggctggt | 9300 |
| ttattgctga taaatctgga gccggtgagc gtgggtctcg cggtatcatt gcagcactgg | 9360 |
| ggccagatgg taagccctcc cgtatcgtag ttatctacac gacggggagt caggcaacta | 9420 |
| tggatgaacg aaatagacag atcgctgaga taggtgcctc actgattaag cattggtaac | 9480 |
| tgtcagacca agtttactca tatatacttt agattgattt aaaacttcat ttttaattta | 9540 |
| aaaggatcta ggtgaagatc cttttt gata atctcatgac caaatccct taacgtgagt | 9600 |
| tttcgttcca ctgagcgtca gaccccgtag aaaagatcaa aggatcttct tgagatcctt | 9660 |
| ttttt ctgcg cgtaatctgc tgcttgcaaa caaaaaaacc accgctacca gcggtggttt | 9720 |
| gtttgccgga tcaagagcta ccaactcttt ttccgaaggt aactggcttc agcagagcgc | 9780 |
| agataccaaa tactgtccttc ctagtgtagc cgtagttagg ccaccacttc aagaactctg | 9840 |
| tagcaccgcc tacatacctc gctctgctaa tcctgttacc agtggctgct gccagtggcg | 9900 |
| ataagtcgtg tcttaccggg ttggactcaa gacgatagtt accggataag gcgcagcggt | 9960 |
| cgggctgaac ggggggttcg tgcacacagc ccagcttgga gcgaacgacc tacaccgaac | 10020 |
| tgagatacct acagcgtgag cattgagaaa gcgccacgct tcccgaaggg agaaaggcgg | 10080 |
| acaggtatcc ggtaagcggc agggtcgaa caggagagcg cacgagggag cttccagggg | 10140 |
| gaaacgcctg gtatctttat agtcctgtcg ggtttcgcca cctctgactt gagcgtcgat | 10200 |
| ttttgtgatg ctcgtcaggg gggcggagcc tatggaaaaa cgccagcaac gcgagctcta | 10260 |
| atacgactca ctatag | 10276 |

<210> SEQ ID NO 2
<211> LENGTH: 10276
<212> TYPE: DNA
<213> ORGANISM: Artificial Sequence
<220> FEATURE:
<223> OTHER INFORMATION: Synthetic polynucleotide

<400> SEQUENCE: 2

| | |
|---|---|
| atgggcggcg catgagagaa gcccagacca attacctacc caaaatggag aaagttcacg | 60 |
| ttgacatcga ggaagacagc ccattcctca gagctttgca gcggagcttc ccgcagtttg | 120 |
| aggtagaagc caagcaggtc actgataatg accatgctaa tgccagagcg ttttcgcatc | 180 |
| tggcttcaaa actgatcgaa acggaggtgg acccatccga cacgatcctt gacattggaa | 240 |
| gtgcgcccgc ccgcagaatg tattctaagc acaagtatca ttgtatctgt ccgatgagat | 300 |
| gtgcggaaga tccggacaga ttgtataagt atgcaactaa gctgaagaaa aactgtaagg | 360 |
| aaataactga taaggaattg acaagaaaa tgaaggagct ggccgccgtc atgagcgacc | 420 |
| ctgacctgga aactgagact atgtgcctcc acgacgacga gtcgtgtcgc tacgaagggc | 480 |
| aagtcgctgt ttaccaggat gtatacgcgg ttgacggacc acaagtctc tatcaccaag | 540 |
| ccaataaggg agttagagtc gcctactgga taggctttga caccacccct tttatgttta | 600 |
| agaacttggc tggagcatat ccatcatact ctaccaactg ggcgacgaa accgtgttaa | 660 |
| cggctcgtaa cataggccta tgcagctctg acgttatgga gcggtcacgt agagggatgt | 720 |
| ccattcttag aaagaagtat ttgaaaccat ccaacaatgt tctattctct gttggctcga | 780 |
| ccatctacca cgagaagagg gacttactga ggagctggca cctgccgtct gtatttcact | 840 |
| tacgtggcaa gcaaaattac acatgtcggt gtgagactat agttagttgc gacgggtacg | 900 |

```
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaggcagacg   1620
tcgacttgat gttacaagag gctggggccg gctcagtgga gacacctcgt ggcttgataa   1680
aggttaccag ctacgatggc gaggacaaga tcggctctta cgctgtgctt ctccgcaggg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg acgtcaatg    2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaatgagaa    2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct ggagagacc ggaccctacc gacgtcttcc    3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
```

```
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattcggta cgatcgcaag gcccgtacgc    3960
acaattctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaacttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaggc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttttccat    4920 tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctc acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa taggggtgatc actagagagg agctcgaggc gcttacccg tcacgcactc    5580 ctagcaggtc ggtctcgaga accagcctgg tctccaaccc gccaggcgta aatagggtga    5640
```

```
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtggaatgc ttcaagaaat atgcgtgtaa taatgaatat tgggaaacgt    6420
ttaaagaaaa ccccatcagg cttactgaag aaaacgtggt aaattacatt accaaattaa    6480
aaggaccaaa agctgctgct cttttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga cccccctaaaa aggctgttta agcttggcaa acctctggca gcagacgatg    7320
aacatgatga tgacaggaga agggcattgc atgaagagtc aacacgctgg aaccgagtgg    7380
gtattctttc agagctgtgc aaggcagtag aatcaaggta tgaaccgta ggaacttcca    7440 tcatagttat ggccatgact actctagcta gcagtgttaa atcattcagc tacctgagag    7500
gggcccctat aactctctac ggctaacctg aatggactac gacatagtct agtccgccaa    7560
gtctagcata tgggcgcgcc ctcagcatcg attgaattgg ccaccatggt gagcaagggc    7620
gaggaggata acatggccat catcaaggag ttcatgcgct tcaaggtgca catggagggc    7680
tccgtgaacg gccacgagtt cgagatcgag ggcgagggcg agggccgccc ctacgagggc    7740
acccagaccg ccaagctgaa ggtgaccaag ggtggccccc tgcccttcgc ctgggacatc    7800
ctgtcccctc agttcatgta cggctccaag gcctacgtga agcacccgc cgacatcccc    7860 gactacttga agctgtcctt ccccgagggc ttcaagtggg agcgcgtgat gaacttcgag    7920
gacggcggcg tggtgaccgt gacccaggac tcctcccctgc aggacggcga gttcatctac    7980
```

```
aaggtgaagc tgcgcggcac caacttcccc tccgacggcc ccgtaatgca gaagaagacc    8040
atgggctggg aggcctcctc cgagcggatg taccccgagg acggcgccct gaagggcgag    8100
atcaagcaga ggctgaagct gaaggacggc ggccactacg acgctgaggt caagaccacc    8160
tacaaggcca agaagcccgt gcagctgccc ggcgcctaca acgtcaacat caagttggac    8220
atcacctccc acaacgagga ctacaccatc gtggaacagt acgaacgcgc cgagggccgc    8280
cactccaccg gcggcatgga cgagctgtac aagtaggaat tggcaagctg cttacataga    8340
actcgcggcg attggcatgc cgccttaaaa ttttttatttt attttctttt tcttttccga    8400
atcggatttt gttttttaata tttcaaaaaa aaaaaaaaaa aaaaaaaaaa cgcgtcgagg    8460
ggaattaatt cttgaagacg aaagggccag gtggcacttt tcggggaaat gtgcgcggaa    8520
cccctatttg tttattttttc taaatacatt caaatatgta tccgctcatg agacaataac    8580
cctgataaat gcttcaataa tattgaaaaa ggaagagtat gagtattcaa catttccgtg    8640
tcgcccttat tccctttttt gcggcatttt gccttcctgt ttttgctcac ccagaaacgc    8700
tggtgaaagt aaaagatgct gaagatcagt tgggtgcacg agtgggttac atcgaactgg    8760
atctcaacag cggtaagatc cttgagagtt ttcgccccga agaacgtttt ccaatgatga    8820 gcactttttaa agttctgcta tgtggcgcgg tattatcccg tgttgacgcc gggcaagagc    8880
aactcggtcg ccgcatacac tattctcaga atgacttggt tgagtactca ccagtcacag    8940
aaaagcatct tacggatggc atgacagtaa gagaattatg cagtgctgcc ataaccatga    9000
gtgataacac tgcggccaac ttacttctga caacgatcgg aggaccgaag gagctaaccg    9060
cttttttgca acatggggg gatcatgtaa ctcgccttga tcgttgggaa ccggagctga    9120
atgaagccat accaaacgac gagcgtgaca ccacgatgcc tgtagcaatg gcaacaacgt    9180
tgcgcaaact attaactggc gaactactta ctctagcttc ccggcaacaa ttaatagact    9240
ggatggaggc ggataaagtt gcaggaccac ttctgcgctc ggcccttccg gctggctggt    9300
ttattgctga taaatctgga gccggtgagc gtgggtctcg cggtatcatt gcagcactgg    9360
ggccagatgg taagccctcc cgtatcgtag ttatctacac gacggggagt caggcaacta    9420
tggatgaacg aaatagacag atcgctgaga taggtgcctc actgattaag cattggtaac    9480
tgtcagacca agtttactca tatatacttt agattgattt aaaacttcat ttttaattta    9540
aaaggatcta ggtgaagatc ctttttgata atctcatgac caaaatccct taacgtgagt    9600
tttcgttcca ctgagcgtca ccccgtag aaaagatcaa aggatcttct tgagatcctt    9660 ttttttctgcg cgtaatctgc tgcttgcaaa caaaaaaacc accgctacca gcggtggttt    9720
gtttgccgga tcaagagcta ccaactcttt ttccgaaggt aactggcttc agcagagcgc    9780
agataccaaa tactgtcctt ctagtgtagc cgtagttagg ccaccacttc aagaactctg    9840
tagcaccgcc tacatacctc gctctgctaa tcctgttacc agtggctgct gccagtggcg    9900
ataagtcgtg tcttaccggg ttggactcaa gacgatagtt accggataag gcgcagcggt    9960
cgggctgaac ggggggttcg tgcacacagc ccagcttgga gcgaacgacc tacaccgaac    10020
tgagatacct acagcgtgag cattgagaaa gcgccacgct tcccgaaggg agaaaggcgg    10080
acaggtatcc ggtaagcggc agggtcggaa caggagagcg cacgagggag cttccagggg    10140
gaaacgcctg gtatctttat agtcctgtcg ggtttcgcca cctctgactt gagcgtcgat    10200
ttttgtgatg ctcgtcaggg gggcggagcc tatggaaaaa cgccagcaac gcgagctcta    10260
atacgactca ctatag                                                  10276
```

```
<210> SEQ ID NO 3
<211> LENGTH: 1629
<212> TYPE: DNA
<213> ORGANISM: Artificial Sequence
<220> FEATURE:
<223> OTHER INFORMATION: Synthetic polynucleotide

<400> SEQUENCE: 3
atgagggtcc ccgctcagct cctggggctc ctgctgctct ggctcccagg tgcacgatgt      60
gccatgtggg agctggagaa agacgtttat gttgtagagg tggactggac tcccgatgcc     120
cctggagaaa cagtgaacct cacctgtgac acgcctgaag aagatgacat cacctggacc     180
tcagaccaga gacatggagt cataggctct ggaaagaccc tgaccatcac tgtcaaagag     240
tttctagatg ctggccagta cacctgccac aaggaggcg agactctgag ccactcacat      300
ctgctgctcc acaagaagga aaatggaatt tggtccactg aaattttaaa aaatttcaaa     360
aacaagactt tcctgaagtg tgaagcacca aattactccg gacggttcac gtgctcatgg     420
ctggtgcaaa gaacatgga cttgaagttc aacatcaaga gcagtagcag ttcccctgac     480
tctcgggcag tgacatgtgg aatggcgtct ctgtctgcag agaaggtcac actggaccaa     540
agggactatg agaagtattc agtgtcctgc caggaggatg tcacctgccc aactgccgag     600
gagaccctgc ccattgaact ggcgttggaa gcacggcagc agaataaata tgagaactac     660
agcaccagct tcttcatcag ggacatcatc aaaccagacc cgcccaagaa cttgcagatg     720 aagccttga agaactcaca ggtggaggtc agctgggagt accctgactc ctggagcact     780
ccccattcct acttctccct caagttcttt gttcgaatcc agcgcaagaa agaaaagatg     840
aaggagacag aggaggggtg taaccagaaa ggtgcgttcc tcgtagagaa gacatctacc     900
gaagtccaat gcaaaggcgg gaatgtctgc gtgcaagctc aggatcgcta ttacaattcc     960
tcatgcagca gtgggcatg tgttccctgc agggtccgat ccggaggttc cggtggtgga    1020
tccggaggtg gctccggcgg cggatccagg tcattccag tctctggacc tgccaggtgt    1080
cttagccagt cccgaaacct gctgaagacc acagatgaca tggtgaagac ggccagagaa    1140
aaactgaaac attattcctg cactgctgaa gacatcgatc atgaagcat cacacgggac    1200 caaaccagca cattgaagac ctgtttacca ctggaactac acaagaacga gagttgcctg    1260
gctactagag agacttcttc cacaacaaga gggagctgcc tgcccccaca gaagacgtct    1320
ttgatgatga cctgtgcct tggtagcatc tatgaggact gaagatgta ccagacagag    1380 ttccaggcca tcaacgcagc acttcagaat cacaaccatc agcagatcat tctagacaag    1440
ggcatgctgg tggccatcga tgagctgatg cagtctctga atcataatgg cgagactctg    1500
cgccagaaac ctcctgtggg agaagcagac ccttacagag tgaaaatgaa gctctgcatc    1560
ctgcttcacg ccttcagcac ccgcgtcgtg accatcaaca gggtgatggg ctatctgagc    1620
tccgcctga                                                          1629

<210> SEQ ID NO 4
<211> LENGTH: 12985
<212> TYPE: DNA
<213> ORGANISM: Artificial Sequence
<220> FEATURE:
<223> OTHER INFORMATION: Synthetic polynucleotide

<400> SEQUENCE: 4
atgggcggcg catgagagaa gcccagacca attacctacc caaaatggag aaagttcacg      60
ttgacatcga ggaagacagc ccattcctca gagctttgca gcggagcttc ccgcagtttg     120
```

```
aggtagaagc caagcaggtc actgataatg accatgctaa tgccagagcg ttttcgcatc      180
tggcttcaaa actgatcgaa acggaggtgg acccatccga cacgatcctt gacattggaa      240
gtgcgcccgc ccgcagaatg tattctaagc acaagtatca ttgtatctgt ccgatgagat      300
gtgcggaaga tccggacaga ttgtataagt atgcaactaa gctgaagaaa aactgtaagg      360
aaataactga taaggaattg acaagaaaaa tgaaggagct ggccgccgtc atgagcgacc      420
ctgacctgga aactgagact atgtgcctcc acgacgacga gtcgtgtcgc tacgaagggc      480
aagtcgctgt ttaccaggat gtatacgcgg ttgacggacc gacaagtctc tatcaccaag      540
ccaataaggg agttagagtc gcctactgga taggctttga caccaccccct tttatgttta     600 agaacttggc tggagcatat ccatcatact ctaccaactg ggccgacgaa accgtgttaa      660
cggctcgtaa cataggccta tgcagctctg acgttatgga gcggtcacgt agagggatgt      720
ccattcttag aaagaagtat ttgaaaccat ccaacaatgt tctattctct gttggctcga      780
ccatctacca cgagaagagg gacttactga ggagctggca cctgccgtct gtatttcact      840
tacgtggcaa gcaaaattac acatgtcggt gtgagactat agttagttgc gacgggtacg      900
tcgttaaaag aatagctatc agtccaggcc tgtatgggaa gccttcaggc tatgctgcta      960
cgatgcaccg cgagggattc ttgtgctgca aagtgacaga cacattgaac ggggagaggg     1020
tctcttttcc cgtgtgcacg tatgtgccag ctacattgtg tgaccaaatg actggcatac     1080
tggcaacaga tgtcagtgcg acgacgcgc aaaaactgct ggttgggctc aaccagcgta      1140
tagtcgtcaa cggtcgcacc cagagaaaca ccaataccat gaaaaattac cttttgcccg     1200
tagtggccca ggcatttgct aggtgggcaa aggaatataa ggaagatcaa gaagatgaaa     1260
ggccactagg actacgagat agacagttag tcatggggtg ttgttgggct tttagaaggc     1320
acaagataac atctatttat aagcgcccgg atacccaaac catcatcaaa gtgaacagcg     1380
atttccactc attcgtgctg cccaggatag gcagtaacac attggagatc gggctgagaa     1440
caagaatcag gaaaatgtta gaggagcaca aggagccgtc acctctcatt accgccgagg     1500
acgtacaaga agctaagtgc gcagccgatg aggctaagga ggtgcgtgaa gccgaggagt     1560
tgcgcgcagc tctaccacct ttggcagctg atgttgagga gcccactctg gaagccgatg     1620
tcgacttgat gttacaagag gctggggccg gctcagtgga gacacctcgt ggcttgataa     1680
aggttaccag ctacgatggc gaggacaaga tcggctctta cgctgtgctt tctccgcagg     1740
ctgtactcaa gagtgaaaaa ttatcttgca tccaccctct cgctgaacaa gtcatagtga     1800
taacacactc tggccgaaaa gggcgttatg ccgtggaacc ataccatggt aaagtagtgg     1860
tgccagaggg acatgcaata cccgtccagg actttcaagc tctgagtgaa agtgccacca     1920
ttgtgtacaa cgaacgtgag ttcgtaaaca ggtacctgca ccatattgcc acacatggag     1980
gagcgctgaa cactgatgaa gaatattaca aaactgtcaa gcccagcgag cacgacggcg     2040
aatacctgta cgacatcgac aggaaacagt gcgtcaagaa agaactagtc actgggctag     2100
ggctcacagg cgagctggtg gatcctccct tccatgaatt cgcctacgag agtctgagaa     2160
cacgaccagc cgctccttac caagtaccaa ccataggggt gtatggcgtg ccaggatcag     2220
gcaagtctgg catcattaaa agcgcagtca ccaaaaaaga tctagtggtg agcgccaaga     2280
aagaaaactg tgcagaaatt ataagggacg tcaagaaaat gaagggctga cgtcaatg       2340 ccagaactgt ggactcagtg ctcttgaatg gatgcaaaca ccccgtagag accctgtata     2400
ttgacgaagc ttttgcttgt catgcaggta ctctcagagc gctcatagcc attataagac     2460
ctaaaaaggc agtgctctgc ggggatcccca acagtgcgg tttttttaac atgatgtgcc     2520
```

```
tgaaagtgca ttttaaccac gagatttgca cacaagtcct ccacaaaagc atctctcgcc    2580
gttgcactaa atctgtgact tcggtcgtct caaccttgtt ttacgacaaa aaatgagaa     2640 cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattcggta cgatcgcaag gcccgtacgc   3960
acaattctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag acaacctgg cggaggggtg tgcggagcgc    4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga atgggaaat gactctcaag gaagcagtgg    4500
ctaggagaga agcagtggag gagatatgca tatccgacga ctcttcagtg acagaacctg   4560
atgcagagct ggtgagggtg catccgaaga gttcttggc tggaaggaag ggctacagca    4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaggc atgagcagta ttaggtcgaa atgccccgtc gaagagtcgg   4800
aagcctccac accacctagc acgctgcctt gcttgtgcat ccatgccatg actccagaaa   4860
```

```
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga gccgatcatc atcgaagagg    5160
aagaaggaga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt ccaccccgc     5520 caggcgtgaa tagggtgatc actagagagg agctcgaggc gcttacccg tcacgcactc     5580 ctagcaggtc ggtctcgaga accagcctgg tctccaaccc gccaggcgta ataggggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tccttttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca agctgcgca gcttccaaa gaaacactcc tatttggaac      6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360
cggcctttaa tgtgaatgc ttcaagaaat atgcgtgtaa taatgaatat tgggaaacgt     6420
ttaaagaaaa ccccatcagg cttactgaag aaaacgtggt aaattacatt accaaattaa    6480
aaggaccaaa agctgctgct ctttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
```

```
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gtctagcata tgggcgcgcc ctcagcatcg atttgaattg gccaccatga ggtccccgc    7620 tcagctcctg gggctcctgc tgctctggct cccaggtgca cgatgtgcca tgtgggagct   7680
ggagaaagac gtttatgttg tagaggtgga ctggactccc gatgccctg gagaaacagt    7740 gaacctcacc tgtgacacgc ctgaagaaga tgacatcacc tggacctcag accagagaca   7800
tggagtcata ggctctggaa agaccctgac catcactgtc aaagagtttc tagatgctgg   7860
ccagtacacc tgccacaaag gaggcgagac tctgagccac tcacatctgc tgctccacaa   7920
gaaggaaaat ggaatttggt ccactgaaat tttaaaaaat ttcaaaaaca agactttcct   7980
gaagtgtgaa gcaccaaatt actccggacg gttcacgtgc tcatggctgg tgcaaagaaa   8040
catggacttg aagttcaaca tcaagagcag tagcagttcc cctgactctc gggcagtgac   8100
atgtggaatg gcgtctctgt ctgcagagaa ggtcacactg gaccaaaggg actatgagaa   8160
gtattcagtg tcctgccagg aggatgtcac ctgcccaact gccgaggaga ccctgcccat   8220
tgaactggcg ttggaagcac ggcagcagaa taaatatgag aactacagca ccagcttctt   8280
catcagggac atcatcaaac cagacccgcc caagaacttg cagatgaagc ctttgaagaa   8340
ctcacaggtg gaggtcagct gggagtaccc tgactcctgg agcactcccc attcctactt   8400
ctccctcaag ttctttgttc gaatccagcg caagaaagaa aagatgaagg agacagagga   8460
ggggtgtaac cagaaaggtg cgttcctcgt agagaagaca tctaccgaag tccaatgcaa   8520
aggcgggaat gtctgcgtgc aagctcagga tcgctattac aattcctcat gcagcaagtg   8580
ggcatgtgtt ccctgcaggg tccgatccgg aggttccggt ggtggatccg gaggtggctc   8640
cggcggcgga tccagggtca ttccagtctc tggacctgcc aggtgtctta gccagtcccg   8700
aaacctgctg aagaccacag atgacatggt gaagacggcc agagaaaaac tgaaacatta   8760
ttcctgcact gctgaagaca tcgatcatga agacatcaca cgggaccaaa ccagcacatt   8820
gaagacctgt ttaccactgg aactacacaa gaacgagagt tgcctggcta ctagagagac   8880
ttcttccaca acaagaggga gctgcctgcc cccacagaag acgtctttga tgatgaccct   8940
gtgccttggt agcatctatg aggacttgaa gatgtaccag acagagttcc aggccatcaa   9000
cgcagcactt cagaatcaca accatcagca gatcattcta gacaagggca tgctggtggc   9060
catcgatgag ctgatgcagt ctctgaatca taatggcgag actctgcgcc agaaacctcc   9120
tgtgggagaa gcagacccct acagagtgaa aatgaagctc tgcatcctgc ttcacgcctt   9180
cagcacccgc gtcgtgacca tcaacagggt gatgggctat ctgagctccg ccggttccgg   9240
tggcggatcc gaagcacaca agagtgagat cgccatcgg tataatgatt tgggagaaca    9300
acatttcaaa ggcctagtcc tgattgcctt ttcccagtat ctccagaaat gctcatacga   9360
tgagcatgcc aaattagtgc aggaagtaac agactttgca aagacgtgtg ttgccgatga   9420
gtctgccgcc aactgtgaca aatcccttca cactcttttt ggagataagt tgtgtgccat   9480
tccaaacctc cgtgaaaact atggtgaact ggctgactgc tgtacaaaac aagagcccga   9540
aagaaacgaa tgtttcctgc aacacaaaga tgacaacccc agcctgccac catttgaaag   9600
```

```
gccagaggct gaggccatgt gcacctcctt taaggaaaac ccaaccacct ttatgggaca     9660
ctatttgcat gaagttgcca gaagacatcc ttatttctat gccccagaac ttctttacta     9720
tgctgagcag tacaatgaga ttctgaccca gtgttgtgca gaggctgaca aggaaagctg     9780
cctgaccccg aagcttgatg gtgtgaagga gaaagcattg gtctcatctg tccgtcagag     9840
aatgaagtgc tccagtatgc agaagtttgg agagagagct tttaaagcat gggcagtagc     9900
tcgtctgagc cagacattcc ccaatgctga ctttgcagaa atcaccaaat tggcaacaga     9960
cctgaccaaa gtcaacaagg agtgctgcca tggtgacctg ctggaatgcg cagatgacag    10020
ggcggaactt gccaagtaca tgtgtgaaaa ccaggcgact atctccagca aactgcagac    10080
ttgctgcgat aaaccactgt tgaagaaagc ccactgtctt agtgaggtgg agcatgacac    10140
catgcctgct gatctgcctg ccattgctgc tgattttgtt gaggaccagg aagtgtgcaa    10200
gaactatgct gaggccaagg atgtcttcct gggcacgttc ttgtatgaat attcaagaag    10260
acaccctgat tactctgtat ccctgttgct gagacttgct aagaaatatg aagccactct    10320
ggaaaagtgc tgcgctgaag ccaatcctcc cgcatgctac ggcacagtgc ttgctgaatt    10380
tcagcctctt gtagaagagc ctaagaactt ggtcaaaacc aactgtgatc tttacgagaa    10440
gcttggagaa tatggattcc aaaatgccat tctagttcgc tacacccaga aagcacctca    10500
ggtgtcaacc ccaactctcg tggaggctgc aagaaaccta ggaagagtgg gcaccaagtg    10560
ttgtacactt cctgaagatc agagactgcc ttgtgtggaa gactatctgt ctgcaatcct    10620
gaaccgtgtg tgtctgctgc atgagaagac cccagtgagt gagcatgtta ccaagtgctg    10680
tagtggatcc ctggtggaaa ggcggccatg cttctctgct ctgacagttg atgaaacata    10740
tgtccccaaa gagtttaaag ctgagacctt caccttccac tctgatatct gcacacttcc    10800
agagaaggag aagcagatta agaaacaaac ggctcttgct gagctggtga agcacaagcc    10860
caaggctaca gcggagcaac tgaagactgt catggatgac tttgcacagt tcctggatac    10920
atgttgcaag gctgctgaca aggacacctg cttctcgact gagggtccaa accttgtcac    10980
tagatgcaaa gacgccttag cctgagcgat cgctaaatac agcagcaatt ggcaagctgc    11040
ttacatagaa ctcgcggcga ttggcatgcc gccttaaaat tttttatttta tttttctttt    11100 cttttccgaa tcggattttg ttttaatat ttcaaaaaaa aaaaaaaaa aaaaaaaac    11160 gcgtcgaggg gaattaattc ttgaagacga aagggccagg tggcactttt cgggaaatg    11220 tgcgcggaac ccctatttgt ttattttttct aaatacattc aaatatgtat ccgctcatga    11280
gacaataacc ctgataaatg cttcaataat attgaaaaag gaagagtatg agtattcaac    11340
atttccgtgt cgcccttatt cccttttttg cggcattttg ccttcctgtt tttgctcacc    11400
cagaaacgct ggtgaaagta aaagatgctg aagatcagtt gggtgcacga gtgggttaca    11460
tcgaactgga tctcaacagc ggtaagatcc ttgagagttt tcgccccgaa gaacgttttc    11520
caatgatgag cacttttaaa gttctgctat gtggcgcggt attatcccgt gttgacgccg    11580
ggcaagagca actcggtcgc cgcatacact attctcagaa tgacttggtt gagtactcac    11640
cagtcacaga aaagcatctt acggatggca tgacagtaag agaattatgc agtgctgcca    11700
taaccatgag tgataacact gcggccaact tacttctgac aacgatcgga ggaccgaagg    11760
agctaaccgc ttttttgcac aacatggggg atcatgtaac tcgccttgat cgttgggaac    11820
cggagctgaa tgaagccata ccaaacgacg agcgtgacac cacgatgcct gtagcaatgg    11880
caacaacgtt gcgcaaacta ttaactggcg aactacttac tctagcttcc cggcaacaat    11940
taatagactg gatggaggcg gataaagttg caggaccact tctgcgctcg gcccttccgg    12000
```

```
ctggctggtt tattgctgat aaatctggag ccggtgagcg tgggtctcgc ggtatcattg    12060
cagcactggg gccagatggt aagccctccc gtatcgtagt tatctacacg acggggagtc    12120
aggcaactat ggatgaacga aatagacaga tcgctgagat aggtgcctca ctgattaagc    12180
attggtaact gtcagaccaa gtttactcat atatacttta gattgattta aaacttcatt    12240
tttaatttaa aaggatctag gtgaagatcc ttttttgataa tctcatgacc aaaatccctt    12300
aacgtgagtt ttcgttccac tgagcgtcag acccgtaga aaagatcaaa ggatcttctt    12360
gagatccttt ttttctgcgc gtaatctgct gcttgcaaac aaaaaaacca ccgctaccag    12420
cggtggtttg tttgccggat caagagctac caactctttt tccgaaggta actggcttca    12480
gcagagcgca gataccaaat actgtccttc tagtgtagcc gtagttaggc caccacttca    12540
agaactctgt agcaccgcct acatacctcg ctctgctaat cctgttacca gtggctgctg    12600
ccagtggcga taagtcgtgt cttaccgggt tggactcaag acgatagtta ccggataagg    12660
cgcagcggtc gggctgaacg gggggttcgt gcacacagcc cagcttggag cgaacgacct    12720
acaccgaact gagatacccta cagcgtgagc attgagaaag cgccacgctt cccgaaggga    12780
gaaaggcgga caggtatccg gtaagcggca gggtcggaac aggagagcgc acgagggagc    12840 ttccagggg aaacgcctgg tatctttata gtcctgtcgg gtttcgccac ctctgacttg    12900
agcgtcgatt tttgtgatgc tcgtcagggg ggcggagcct atggaaaaac gccagcaacg    12960
cgagctctaa tacgactcac tatag                                         12985
```

<210> SEQ ID NO 5
<211> LENGTH: 13981
<212> TYPE: DNA
<213> ORGANISM: Artificial Sequence
<220> FEATURE:
<223> OTHER INFORMATION: Synthetic polynucleotide

<400> SEQUENCE: 5

```
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccatgagat     300 gtgcggaaga tccggacaga ttgtataagt atgcaactaa gctgaagaaa actgtaagg     360 aaataactga taaggaattg acaagaaaaa tgaaggagct ggccgccgtc atgagcgacc     420
ctgacctgga aactgagact atgtgcctcc acgacgacga gtcgtgtcgc tacgaagggc     480
aagtcgctgt ttaccaggat gtatacgcgg ttgacggacc gacaagtctc tatcaccaag     540
ccaataaggg agttagagtc gcctactgga taggctttga caccacccct tttatgttta     600
agaacttggc tggagcatat ccatcatact ctaccaactg ggccgacgaa accgtgttaa     660
cggctcgtaa cataggccta tgcagctctg acgttatgga gcggtcacgt agagggatgt     720
ccattcttag aaagaagtat ttgaaaccat ccaacaatgt tctattctct gttggctcga     780
ccatctacca cgagaagagg gacttactga ggagctggca cctgccgtct gtatttcact     840
tacgtggcaa gcaaaattac acatgtcggt gtgagactat agttagttgc gacgggtacg     900
tcgttaaaag aatagctatc agtccaggcc tgtatgggaa gccttcaggc tatgctgcta     960
cgatgcaccg cgagggattc ttgtgctgca aagtgacaga cacattgaac ggggagaggg    1020
```

-continued

```
tctcttttcc cgtgtgcacg tatgtgccag ctacattgtg tgaccaaatg actggcatac    1080
tggcaacaga tgtcagtgcg gacgacgcgc aaaaactgct ggttgggctc aaccagcgta    1140
tagtcgtcaa cggtcgcacc cagagaaaca ccaataccat gaaaaattac cttttgcccg    1200
tagtggccca ggcatttgct aggtgggcaa aggaatataa ggaagatcaa gaagatgaaa    1260
ggccactagg actacgagat agacagttag tcatggggtg ttgttgggct tttagaaggc    1320
acaagataac atctatttat aagcgcccgg atacccaaac catcatcaaa gtgaacagcg    1380
atttccactc attcgtgctg cccaggatag gcagtaacac attggagatc gggctgagaa    1440
caagaatcag gaaaatgtta gaggagcaca aggagccgtc acctctcatt accgccgagg    1500
acgtacaaga agctaagtgc gcagccgatg aggctaagga ggtgcgtgaa gccgaggagt    1560
tgcgcgcagc tctaccacct ttggcagctg atgttgagga gcccactctg gaagccgatg    1620
tcgacttgat gttacaagag gctggggccg gctcagtgga gacacctcgt ggcttgataa    1680
aggttaccag ctacgatggc gaggacaaga tcggctctta cgctgtgctt tctccgcagg    1740
ctgtactcaa gagtgaaaaa ttatcttgca tccaccctct cgctgaacaa gtcatagtga    1800
taacacactc tggccgaaaa gggcgttatg ccgtggaacc ataccatggt aaagtagtgg    1860
tgccagaggg acatgcaata cccgtccagg actttcaagc tctgagtgaa agtgccacca    1920
ttgtgtacaa cgaacgtgag ttcgtaaaca ggtacctgca ccatattgcc acacatggag    1980
gagcgctgaa cactgatgaa gaatattaca aaactgtcaa gcccagcgag cacgacggcg    2040
aatacctgta cgacatcgac aggaaacagt gcgtcaagaa agaactagtc actgggctag    2100
ggctcacagg cgagctggtg gatcctccct tccatgaatt cgcctacgag agtctgagaa    2160
cacgaccagc cgctccttac caagtaccaa cataggggt gtatggcgtg ccaggatcag    2220
gcaagtctgg catcattaaa agcgcagtca ccaaaaaaga tctagtggtg agcgccaaga    2280
aagaaaactg tgcagaaatt ataagggacg tcaagaaaat gaaagggctg acgtcaatg    2340
ccagaactgt ggactcagtg ctcttgaatg gatgcaaaca ccccgtagag accctgtata    2400
ttgacgaagc ttttgcttgt catgcaggta ctctcagagc gctcatagcc attataagac    2460
ctaaaaaggc agtgctctgc ggggatccca acagtgcgg ttttttaac atgatgtgcc    2520
tgaaagtgca ttttaaccac gagatttgca cacaagtctt ccacaaaagc atctctcgcc    2580
gttgcactaa atctgtgact tcggtcgtct caaccttgtt ttacgacaaa aaatgagaa    2640
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga ataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct ggagagaccc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
```

```
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggacccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattcggta cgatcgcaag gcccgtacgc    3960
acaattctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag acaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaacccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag ggctacagca    4620
caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaggc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tccttttccat    4920 tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
acgagactcc ggagccatcg gcagagaacc aatccacaga ggggacacct gaacaaccac    5100
cacttataac cgaggatgag accaggacta gaacgcctga ccgatcatc atcgaagagg    5160 aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttacccccg tcacgcactc    5580 ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca acaaaaatca gtaaggcaaa    5760
```

```
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct cttttttgcga agacacataa tttgaatatg ttgcaggaca   6540
taccaatgga caggttttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
ggccccctat aactctctac ggctaacctg aatggactac gacatagtct agtccgccaa   7560
gtctagcata tgggcgcgcc ctcagcatcg atttgaattg ccaccatgga gggtccccgc   7620
tcagctcctg ggctcctgc tgctctggct cccaggtgca cgatgtgcca gtgggagct   7680
ggagaaagac gtttatgttg tagaggtgga ctggactccc gatgcccctg agaaacagt   7740
gaacctcacc tgtgacacgc ctgaagaaga tgacatcacc tggaccctcag accagagaca   7800
tggagtcata ggctctggaa agaccctgac catcactgtc aaagagtttc tagatgctgg   7860
ccagtacacc tgccacaaag gaggcgagac tctgagccac tcacatctgc tgctccacaa   7920
gaaggaaaat ggaatttggt ccactgaaat tttaaaaaat ttcaaaaaca agactttcct   7980
gaagtgtgaa gcaccaaatt actccggacg gttcacgtgc tcatggctgg tgcaaagaaa   8040
catggacttg aagttcaaca tcaagagcag tagcagttcc cctgactctc gggcagtgac   8100
atgtggaatg gcgtctctgt ctgcagagaa ggtcacactg gaccaaaggg actatgagaa   8160
```

```
gtattcagtg tcctgccagg aggatgtcac ctgcccaact gccgaggaga ccctgcccat    8220
tgaactggcg ttggaagcac ggcagcagaa taaatatgag aactacagca ccagcttctt    8280
catcagggac atcatcaaac cagacccgcc caagaacttg cagatgaagc ctttgaagaa    8340
ctcacaggtg gaggtcagct gggagtaccc tgactcctgg agcactcccc attcctactt    8400
ctccctcaag ttctttgttc gaatccagcg caagaaagaa aagatgaagg agacagagga    8460
ggggtgtaac cagaaaggtg cgttcctcgt agagaagaca tctaccgaag tccaatgcaa    8520
aggcgggaat gtctgcgtgc aagctcagga tcgctattac aattcctcat gcagcaagtg    8580
ggcatgtgtt ccctgcaggg tccgatccgg aggttccggt ggtggatccg gaggtggctc    8640
cggcggcgga tccagggtca ttccagtctc tggacctgcc aggtgtctta gccagtcccg    8700
aaacctgctg aagaccacag atgacatggt gaagacggcc agagaaaaac tgaaacatta    8760
ttcctgcact gctgaagaca tcgatcatga agacatcaca cgggaccaaa ccagcacatt    8820
gaagacctgt ttaccactgg aactacacaa gaacgagagt tgcctggcta ctagagagac    8880
ttcttccaca acaagaggga gctgcctgcc cccacagaag acgtctttga tgatgaccct    8940
gtgccttggt agcatctatg aggacttgaa gatgtaccag acagagttcc aggccatcaa    9000
cgcagcactt cagaatcaca accatcagca gatcattcta gacaagggca tgctggtggc    9060
catcgatgag ctgatgcagt ctctgaatca taatggcgag actctgcgcc agaaacctcc    9120
tgtgggagaa gcagacccctt acagagtgaa aatgaagctc tgcatcctgc ttcacgcctt    9180
cagcacccgc gtcgtgacca tcaacagggt gatgggctat ctgagctccg ccggttccgg    9240
tggcggatcc gaagcacaca agagtgagat cgcccatcgg tataatgatt gggagaaca    9300 acatttcaaa ggcctagtcc tgattgcctt ttcccagtat ctccagaaat gctcatacga    9360
tgagcatgcc aaattagtgc aggaagtaac agactttgca aagacgtgtg ttgccgatga    9420
gtctgccgcc aactgtgaca aatcccttca cactcttttt ggagataagt tgtgtgccat    9480
tccaaacctc cgtgaaaact atggtgaact ggctgactgc tgtacaaaac aagagcccga    9540
aagaaacgaa tgtttcctgc aacacaaaga tgacaacccc agcctgccac catttgaaag    9600
gccagaggct gaggccatgt gcacctcctt taaggaaaac ccaaccacct ttatgggaca    9660
ctatttgcat gaagttgcca gaagacatcc ttatttctat gccccagaac ttctttacta    9720
tgctgagcag tacaatgaga ttctgaccca gtgttgtgca gaggctgaca ggaaagctg    9780 cctgaccccg aagcttgatg gtgtgaagga gaaagcattg gtctcatctg tccgtcagag    9840
aatgaagtgc tccagtatgc agaagtttgg agagagagct tttaaagcat gggcagtagc    9900
tcgtctgagc cagacattcc ccaatgctga ctttgcagaa atcaccaaat tggcaacaga    9960
cctgaccaaa gtcaacaagg agtgctgcca tggtgacctg ctggaatgcg cagatgacag   10020
ggcggaactt gccaagtaca tgtgtgaaaa ccaggcgact atctccagca aactgcagac   10080
ttgctgcgat aaaccactgt gaagaaagc ccactgtctt agtgaggtgg agcatgcac    10140 catgcctgct gatctgcctg ccattgctgc tgattttgtt gaggaccagg aagtgtgcaa   10200
gaactatgct gaggccaagg atgtcttcct gggcacgttc ttgtatgaat attcaagaag   10260
acaccctgat tactctgtat ccctgttgct gagacttgct aagaaatatg aagccactct   10320
ggaaaagtgc tgcgctgaag ccaatcctcc cgcatgctac ggcacagtgc ttgctgaatt   10380
tcagcctctt gtagaagagc ctaagaactt ggtcaaaacc aactgtgatc tttacgaaa    10440 gcttggagaa tatggattcc aaaatgccat tctagttcgc tacacccaga agcacctca    10500
```

```
ggtgtcaacc ccaactctcg tggaggctgc aagaaaccta ggaagagtgg gcaccaagtg   10560
ttgtacactt cctgaagatc agagactgcc ttgtgtggaa gactatctgt ctgcaatcct   10620
gaaccgtgtg tgtctgctgc atgagaagac cccagtgagt gagcatgtta ccaagtgctg   10680
tagtggatcc ctggtggaaa ggcggccatg cttctctgct ctgacagttg atgaaacata   10740
tgtccccaaa gagtttaaag ctgagacctt caccttccac tctgatatct gcacacttcc   10800
agagaaggag aagcagatta agaaacaaac ggctcttgct gagctggtga agcacaagcc   10860
caaggctaca gcggagcaac tgaagactgt catggatgac tttgcacagt tcctggatac   10920
atgttgcaag gctgctgaca aggacacctg cttctcgact gagggtccaa accttgtcac   10980
tagatgcaaa gacgccttag ccggcggagg ttccggtggc ggatcccaat actatgacta   11040
cgatataccc ctgttcatgt acgggcaaat atctccaaac tgtgcaccag aatgtaactg   11100
ccctcactca taccccactg caatgtactg tgacgacctg aagttgaaat ccgtgccaat   11160
ggtgcctcct gggattaagt acctgtacct ccgcaacaat cagatcgacc atattgacga   11220
gaaggctttt gaaaacgtca cagacctcca gtggcttatc ctggaccata acctgcttga   11280
aaatagtaag ataaagggca agtatttttc caaacttaaa cagcttaaaa aactccacat   11340
caactacaat aaccttactg aatccgtggg accattgcca aaatctctcc aagatttgca   11400
gttgactaac aacaagatat ccaaactcgg ctccttcgat gggctggtta atctgacttt   11460
catctacttg caacacaacc aattgaagga ggatgcagtt tcagctagtc ttaaaggtct   11520
gaaaagcctt gagtatcttg atctgtcatt taatcaaatg tccaagctcc ctgctgggct   11580
cccaacaagt ctgctgacac tctatctcga caataacaag ataagtaaca ttcccgatga   11640
gtactttaaa agatttaccg gcctccaata cttgcggctt tctcacaacg agttggcaga   11700
ctctggtgta cccggcaact cctttaatat aagttctctt ctcgagcttg atttgtccta   11760
taacaaactg aagagtatcc ctactgtcaa tgaaaatttg gagaattact acctcgaagt   11820
caatgagctt gagaagttcg atgttaagtc tttctgtaag atactgggtc cattgtcata   11880
cagcaagatt aaacatcttc gcttggatgg gaatcccttg actcaaagct cacttccccc   11940
cgacatgtac gaatgcctga gggtagccaa cgaaatcaca gtaaacggag gtggctcctg   12000
agcgatcgct aaatacagca gcaattggca agctgcttac atagaactcg cggcgattgg   12060
catgccgcct taaaattttt attttatttt tcttttcttt tccgaatcgg attttgtttt   12120
taatatttca aaaaaaaaaa aaaaaaaaaa aaaaacgcgt cgagggggaat taattcttga   12180 agacgaaagg gccaggtggc acttttcggg gaaatgtgcg cggaacccct atttgtttat   12240
ttttctaaat acattcaaat atgtatccgc tcatgagaca ataaccctga taaatgcttc   12300
aataatattg aaaaggaag agtatgagta ttcaacattt ccgtgtcgcc cttattccct   12360
tttttgcggc attttgcctt cctgtttttg ctcacccaga aacgctggtg aaagtaaaag   12420
atgctgaaga tcagttgggt gcacgagtgg gttacatcga actggatctc aacagcggta   12480
agatccttga gagttttcgc cccgaagaac gttttccaat gatgagcact tttaaagttc   12540
tgctatgtgg cgcggtatta tcccgtgttg acgccgggca agagcaactc ggtcgccgca   12600
tacactattc tcagaatgac ttggttgagt actcaccagt cacagaaaag catcttacgg   12660
atggcatgac agtaagagaa ttatgcagtg ctgccataac catgagtgat aacactgcgg   12720
ccaacttact tctgacaacg atcggaggac cgaaggagct aaccgctttt ttgcacaaca   12780
tgggggatca tgtaactcgc cttgatcgtt gggaaccgga gctgaatgaa gccataccaa   12840
acgacgagcg tgacaccacg atgcctgtag caatggcaac aacgttgcgc aaactattaa   12900
```

```
ctggcgaact acttactcta gcttcccggc aacaattaat agactggatg gaggcggata   12960
aagttgcagg accacttctg cgctcggccc ttccggctgg ctggtttatt gctgataaat   13020
ctggagccgg tgagcgtggg tctcgcggta tcattgcagc actggggcca gatggtaagc   13080
cctcccgtat cgtagttatc tacacgacgg ggagtcaggc aactatggat gaacgaaata   13140
gacagatcgc tgagataggt gcctcactga ttaagcattg gtaactgtca gaccaagttt   13200
actcatatat actttagatt gatttaaaac ttcatttta atttaaaagg atctaggtga    13260 agatccttt tgataatctc atgaccaaaa tcccttaacg tgagttttcg ttccactgag    13320
cgtcagaccc cgtagaaaag atcaaaggat cttcttgaga tccttttttt ctgcgcgtaa   13380
tctgctgctt gcaaacaaaa aaaccaccgc taccagcggt ggtttgtttg ccggatcaag   13440
agctaccaac tctttttccg aaggtaactg gcttcagcag agcgcagata ccaaatactg   13500
tccttctagt gtagccgtag ttaggccacc acttcaagaa ctctgtagca ccgcctacat   13560
acctcgctct gctaatcctg ttaccagtgg ctgctgccag tggcgataag tcgtgtctta   13620
ccgggttgga ctcaagacga tagttaccgg ataaggcgca gcggtcgggc tgaacggggg   13680
gttcgtgcac acagcccagc ttggagcgaa cgacctacac cgaactgaga tacctacagc   13740
gtgagcattg agaaagcgcc acgcttcccg aagggagaaa ggcggacagg tatccggtaa   13800
gcggcagggt cggaacagga gagcgcacga gggagcttcc agggggaaac gcctggtatc   13860
tttatagtcc tgtcgggttt cgccacctct gacttgagcg tcgattttg tgatgctcgt    13920 caggggggcg gagcctatgg aaaaacgcca gcaacgcgag ctctaatacg actcactata   13980
g                                                                  13981
```